US008288311B2

(12) United States Patent
Dhingra et al.

(10) Patent No.: US 8,288,311 B2
(45) Date of Patent: Oct. 16, 2012

(54) HYDRO-OXIDATION PROCESS USING A CATALYST PREPARED FROM A GOLD CLUSTER COMPLEX

(75) Inventors: Sandeep S. Dhingra, Midland, MI (US); Rick C. Schroden, Sanford, MI (US); Keith J. Watson, Midland, MI (US); David G. Barton, Midland, MI (US); Robert G. Bowman, Midland, MI (US); Larry N. Ito, Midland, MI (US); David L. Trent, Lake Jackson, TX (US); Heiko Weiner, Sanford, MI (US)

(73) Assignee: Dow Global Technologies LLC

( * ) Notice: Subject to any disclaimer, the term of this patent is extended or adjusted under 35 U.S.C. 154(b) by 522 days.

(21) Appl. No.: 12/445,547

(22) PCT Filed: Nov. 7, 2007

(86) PCT No.: PCT/US2007/083859
§ 371 (c)(1),
(2), (4) Date: Apr. 14, 2009

(87) PCT Pub. No.: WO2008/063880
PCT Pub. Date: May 29, 2008

(65) Prior Publication Data
US 2010/0076208 A1     Mar. 25, 2010

Related U.S. Application Data

(60) Provisional application No. 60/859,738, filed on Nov. 17, 2006.

(51) Int. Cl.
*B01J 29/90* (2006.01)
*B01J 21/16* (2006.01)
*B01J 23/52* (2006.01)
*B01J 23/48* (2006.01)

(52) U.S. Cl. .............. 502/344; 502/64; 502/66; 502/87; 502/243; 502/245; 502/506; 977/779; 977/781

(58) Field of Classification Search .................. 502/242, 502/243, 344, 439, 506, 60–87, 508–511; 977/779, 781
See application file for complete search history.

(56) References Cited

U.S. PATENT DOCUMENTS
5,859,265 A    1/1999  Muller et al.
(Continued)

FOREIGN PATENT DOCUMENTS
DE    19600708    7/1997
(Continued)

OTHER PUBLICATIONS

A. Zwijnenburg, M. Saleh, M. Makkee, and J.A. Moulijn, "Direct gas-phase epoxidation of propene over bimetallic Au catalysts," Catalysis Today 72 (2002), pp. 59-62.*

(Continued)

*Primary Examiner* — Stanley Silverman
*Assistant Examiner* — Diana J Liao

(57) ABSTRACT

A process and catalyst for the hydro-oxidation of an olefin having three or more carbon atoms, such as propylene, to form an olefin oxide, such as propylene oxide. The process involves contacting the olefin with oxygen in the presence of hydrogen and a hydro-oxidation catalyst under reaction conditions; the catalyst comprising gold nanoparticles deposited on a nanoporous titanium-containing support, prepared by depositing a gold-ligand cluster complex onto the support to form a catalyst precursor, and then heating and/or chemically treating the catalyst precursor to form the hydro-oxidation catalyst composition. The hydro-oxidation catalyst exhibits stabilized catalyst activity, enhanced lifetime, and improved hydrogen efficiency.

20 Claims, 19 Drawing Sheets

U.S. PATENT DOCUMENTS

Figure 1:
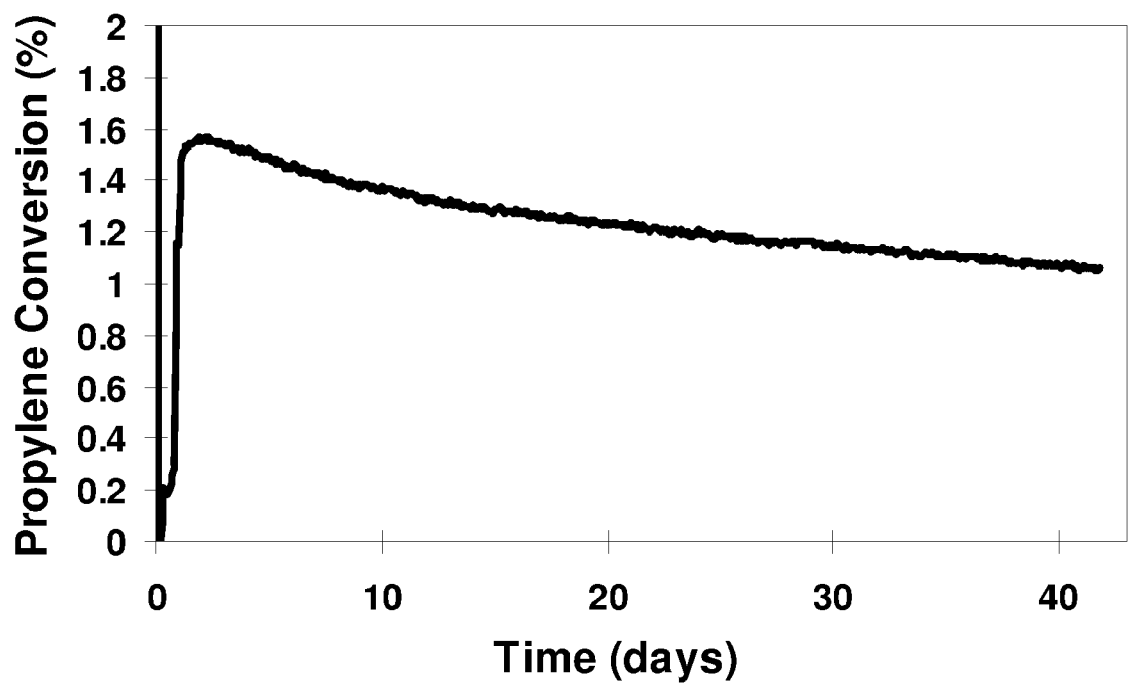
Figure 1:
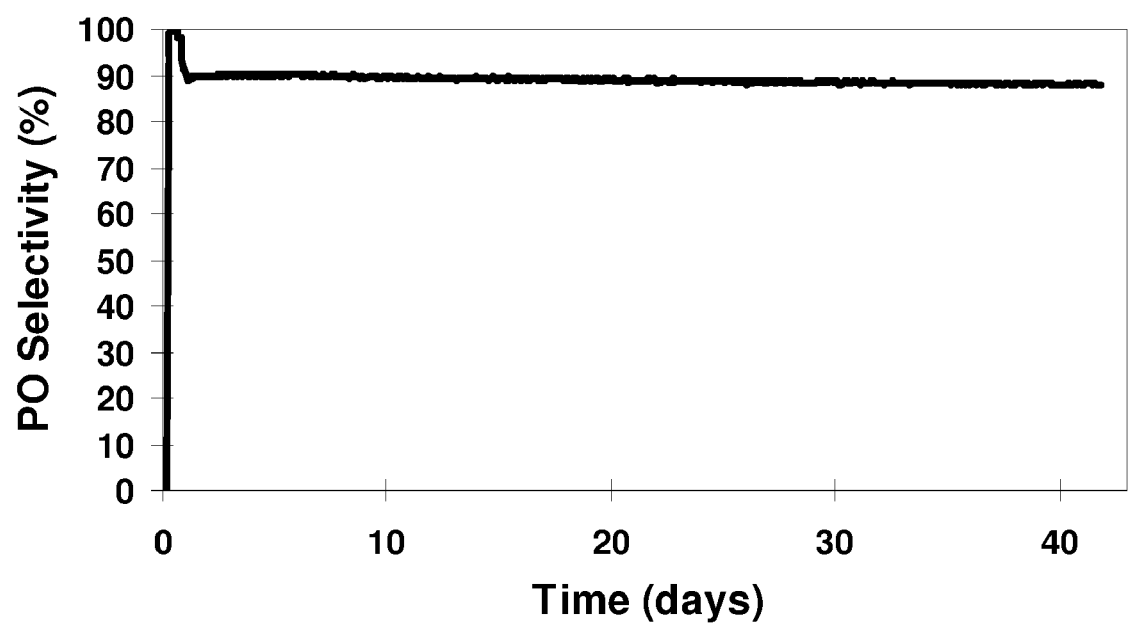

| | | | |
|---|---|---|---|
| 5,965,754 | A | 10/1999 | Clark et al. |
| 6,008,389 | A | 12/1999 | Grosch et al. |
| 6,031,116 | A | 2/2000 | Bowman et al. |
| 6,255,499 | B1 | 7/2001 | Kuperman et al. |
| 6,309,998 | B1 | 10/2001 | Bowman et al. |
| 6,323,351 | B1 | 11/2001 | Bowman et al. |
| 6,362,349 | B1 | 3/2002 | Kuperman et al. |
| 6,524,991 | B2 | 2/2003 | Bowman et al. |
| 6,562,986 | B2 | 5/2003 | Bowman et al. |
| 6,646,142 | B1 | 11/2003 | Meima et al. |
| 6,670,491 | B2 | 12/2003 | Bowman et al. |
| 6,821,923 | B1 | 11/2004 | Kuperman et al. |
| 2004/0176620 | A1* | 9/2004 | Kuperman et al. .......... 549/533 |
| 2004/0180787 | A1 | 9/2004 | Rolison et al. |
| 2005/0095189 | A1 | 5/2005 | Brey et al. |
| 2007/0093669 | A1* | 4/2007 | Le-Khac et al. ............. 549/536 |

FOREIGN PATENT DOCUMENTS

| | | |
|---|---|---|
| DE | 19609301 | 11/1997 |
| EP | 0709360 | 12/1998 |
| WO | 9800413 | 1/1998 |
| WO | 9800414 | 1/1998 |
| WO | 9800415 | 1/1998 |
| WO | 03062196 | 7/2003 |
| WO | 2006003450 | 1/2006 |

OTHER PUBLICATIONS

B.D. Chandler, L.I. Rubinstein, L.H. Pignolet, "Alkane dehydrogenation with silica supported platinum and platinum-gold catalyst derived from phosphine ligated precursor," Journal of Molecular Catalysis A: Chemical 33 (1998), pp. 267-282.*

Al. Kozlov, A.P. Kozlova, H. Liu, Y. Iwasawa, "A new approach to active supported Au catalysts," Applied Catalysis A: General 182 (1999), pp. 9-28.*

A.K. Sinha, S. Seelan, S. Tsubota, and M. Haruta, "Catalysis by gold nanoparticles: epoxidation of propene," Topics in Catalysis vol. 29 No. 3-4 (Jun. 2004), pp. 95-102.*

Haruta, M., "Gold as a Novel Catalyst in the 21$^{st}$ Century: Preparation, Working Mechanism and Applications," Gold Bulletin 37/1-2 (2004), pp. 27-36.*

Choudhary, T.V., et al. "CO Oxidation on Supported Nano-Au Catalysts Synthesized from a [Au6 (PPH3)] (BF4)2 Complex" Journal of Catalysis. 2002. 247-255, vol. 207.

Nijhuis, T.A. et al. "Direct Epoxidation of Propene Using Gold Dispersed on TS-1 and Other Titanium-Containing Supports." Industrial Engineering and Chemical Research. 1999, p. 884-891 vol. 38.

Cumaranatunge, L. et al. "Enhancement of Au capture efficiency and activity of Au/TS-1 catalysts for propylene epoxidation." Journal of Catalysis. 2005. p. 38-42, vol. 232.

Menard, L. et al. "Preparation of TiO2-supported Au Nanoparticle catalysts from a Au13 cluster precursor: Ligand removal using ozone exposure versus a rapid thermal treatment." Journal of Catalysis. 2006. p. 64-73 vol. 243.

Santra, A.K., et al. "The growth of AG-Au bimetallic nanoparticles on TiO2(1 1 0)" Surface Science. 2004. p. 324-332 vol. 548.

Meier, D., et al. "The Influence of Metal Cluster Size on Adsorption Energies: CO Adsorbed on Au Clusters Supported on TiO2." Journal of American Chemical Society. 2004. 1982-1899. vol. 126.

Valden, et al. "Onset of Catalytic Activity of Gold Clusters on Titania with the Appearance of Nonmetallic Properties." Science, 1998. p. 1647-1650 vol. 281.

Chusuei, C.C., et al. "A Nanoscale Model Catalyst Preparation: Solution Deposition of Phosphine-Stabilized Gold Clusters onto a Planar TiO2(110) Support." American Chemical Society. 2001. 4113-4117. vol. 17.

Kolmakov, A., et al. "Imaging gold clusters on TiO2(110) at elevated pressures and temperatures." Catalysis Letters 2000. p. 93-97. vol. 70.

* cited by examiner

HYDRO-OXIDATION PROCESS USING A CATALYST PREPARED FROM A GOLD CLUSTER COMPLEX

CROSS REFERENCE TO RELATED APPLICATIONS

This application is a 371 of PCT/US2007/083859 filed Nov. 7, 2007, which claims the benefit of U.S. Provisional Application Ser. No. 60/859,738, filed Nov. 17, 2006.

BACKGROUND OF THE INVENTION

This invention pertains to an improved process and catalyst for the hydro-oxidation of olefins, such as propylene, by oxygen in the presence of hydrogen to form olefin oxides, such as propylene oxide.

Olefin oxides, such as propylene oxide, are used to alkoxylate alcohols to form polyether polyols, which find widespread utility in the manufacture of polyurethanes and synthetic elastomers. Olefin oxides are also important intermediates in the manufacture of alkylene glycols, such as propylene glycol, and alkanolamines, such as isopropanolamine, which are useful as solvents and surfactants.

The direct oxidation of olefins having three or more carbon atoms (C3+ olefins) with oxygen has been the subject of intense industrial interest for several decades. Much effort has focused on the direct oxidation of propylene by oxygen to propylene oxide. Such a process is sought for replacement of indirect multi-step manufacturing processes currently in practice, including the well-known chlorohydrin and organic hydroperoxide routes to propylene oxide. It is known that silver catalysts can catalyze the direct oxidation of propylene with oxygen to propylene oxide in a selectivity of not more than about 70 mole percent. Disadvantageously, the process produces significant quantities of partial oxidation by-products, including acrolein, acetone, and propionaldehyde, as well as deep oxidation by-products, namely, carbon monoxide and carbon dioxide.

Over the past ten years many patents have disclosed direct hydro-oxidation of olefins having three or more carbon atoms with oxygen in the presence of hydrogen to form olefin oxides. Catalysts for the hydro-oxidation are disclosed to comprise gold, silver, and noble metals, such as palladium and platinum, and optionally one or more promoters, such as alkali, alkaline earths, and rare earths, deposited on a titanium-containing support, such as, titania or a titanosilicate zeolite. In particular, gold or gold in combination with silver and/or a noble metal (e.g., bimetallic catalyst with palladium) has been the subject of considerable patent activity, with some patents disclosing oxidized gold as a catalytically-active species and other patents disclosing metallic gold of a particle size greater than 1 nanometer (nm) and less than about 100 nm as the catalytically-active species. A representative group of patents drawn towards the hydro-oxidation of C3+ olefins using catalysts comprising gold, silver, and/or a noble metal deposited on a titanium-containing support include the following: EP-A1-0,709,360, WO 98/00413, WO 98/00414, WO 98/00415, U.S. Pat. No. 6,255,499, WO 03/062196, WO 96/02323, WO 97/25143, and WO 97/47386. In the aforementioned prior art, the catalysts are prepared by impregnation of or precipitation from one or more solutions of soluble salts of gold, silver, and/or one or more noble metals and soluble salts of one or more promoters. The aforementioned prior art disclose for such hydro-oxidation processes a high selectivity to C3+ olefin oxides, most particularly, propylene oxide. A propylene oxide selectivity greater than about 90 mole percent is achievable; and selectivities to propylene oxide in excess of 95 mole percent have also been reported.

Despite such advances, several problems of the prior art need to be addressed before the hydro-oxidation route can replace current manufacturing processes for preparing olefin oxides. First, hydrogen efficiency needs to be improved. Hydrogen is a necessary reactant in producing the olefin oxide. For every mole of olefin oxide produced, the olefin hydro-oxidation produces a stoichiometric equivalent of water. Additional water can also be formed through one or more undesirable side-reactions, for example, by the direct oxidation of hydrogen with oxygen. Hydrogen efficiency can be ascertained by measuring a molar ratio of water to olefin oxide in the product stream, e.g., water to propylene oxide ($H_2O$/PO). Desirably, the ratio is 1/1; but in practice, at any specific time during process operation, a higher ratio is usually observed. Moreover, with current prior art catalysts, the formation of water and the water/olefin oxide molar ratio increase unacceptably with time. While it is informative to track the water/olefin oxide molar ratio at intervals throughout a process, a cumulative water/olefin oxide molar ratio may be more indicative of overall hydrogen efficiency. For the purposes of this invention, the term "cumulative water/olefin oxide molar ratio" means the average water/olefin oxide molar ratio over the total run time, preferably, averaged from measurements of the water and olefin oxide concentrations in the product stream taken at least every three hours, preferably, at least every two hours, and more preferably, every hour. In prior art processes over time, the cumulative water/olefin oxide molar ratio increases and often exceeds greater than about 10/1, which is unacceptably high.

Second, prior art processes operate at a temperature typically between about 70° C. and about 170° C. Beyond this temperature range, and often within this range depending upon the catalyst, prior art processes exhibit decreased selectivity to olefin oxides and increased selectivities to undesirable partial oxidation products (e.g., propionaldehyde, acetone, acrolein), deep oxidation products (namely, carbon monoxide and carbon dioxide), hydrogenation products (e.g., propane), and water. Moreover, prior art catalysts tend to deactivate quickly with increasing temperature. Operating at higher temperatures, for example, at 160° C. or higher, with stable activity and selectivity is desirable, because a hotter water co-product (steam) can be utilized, if desired, in downstream plant operations. Heat integration resulting therefrom can be beneficial to overall plant economics and management.

Third, in determinations of the overall economics of hydro-oxidation processes, the quantity of gold, silver, and noble metal in the catalyst should be taken into consideration. Gold, silver, and noble metals are notoriously expensive; therefore, any decrease in the quantities thereof required for the hydro-oxidation catalyst would provide added value.

Fourth and most importantly, prior art hydro-oxidation catalysts exhibit decreasing activity over time and reach a reduced level of activity after several days. At such time, the hydro-oxidation process must be shut down, and the catalyst must be regenerated. A need exists in the art to stabilize the activity of the catalyst over a longer run-time, so as to increase the intervals between catalyst regenerations and to increase overall catalyst lifetime. The term "catalyst lifetime" as used herein refers to the time measured from the start of the hydro-oxidation process to a point at which the catalyst, after one or more regenerations, has lost sufficient activity so as to render the catalyst unacceptable, particularly, from a commercial point of view.

We note that T. Alexander Nijhuis, et al. in *Industrial Engineering and Chemical Research*, 38 (1999), 884-891, discloses a catalyst containing gold particles on the exterior surface of a titanosilicate support for the hydro-oxidation of propylene with oxygen in the presence of hydrogen to form propylene oxide. The catalyst is prepared by conventional deposition-precipitation from an aqueous solution of gold (III) chloride.

Further, several references, as illustrated by T. V. Choudhary, et al., *Journal of Catalysis*, 207, 247-255 (2002), disclose nano-gold catalysts supported on titania prepared from gold-phosphine ligand cluster complexes. WO 2005/030382 discloses a heterogeneous catalyst comprising gold particles on a support medium, such as titanium oxide-coated alumina, wherein the gold particles are physically vapor deposited at a Penetration Depth Ratio in a range from about $1 \times 10^{-9}$ to about 0.1. These references are silent with respect to hydro-oxidation processes.

SUMMARY OF THE INVENTION

This invention provides for a hydro-oxidation process of preparing an olefin oxide directly from an olefin and oxygen in the presence of hydrogen. The process comprises contacting an olefin having three or more carbon atoms with oxygen in the presence of hydrogen and in the presence of a hydro-oxidation catalyst under process conditions sufficient to produce the corresponding olefin oxide. The hydro-oxidation catalyst employed in the process of this invention comprises gold nanoparticles deposited on particles of a nanoporous titanium-containing support, the catalyst being prepared by a process comprising depositing a gold-ligand cluster complex onto a nanoporous titanium-containing support under conditions sufficient to form a catalyst precursor, and then heating and/or chemically treating the catalyst precursor under conditions sufficient to form the hydro-oxidation catalyst.

The novel process of this invention is useful for producing an olefin oxide directly from an olefin having three or more carbon atoms and oxygen in the presence of hydrogen. The advantages of the process of this invention are discussed hereinafter; but such a discussion should not impose any limitations on the process as claimed herein. As a first advantage, the process of this invention typically achieves stable catalyst activity over an extended run time of greater than about 25 days, and preferably, greater than about 30 days. The extended run time beneficially increases the intervals between catalyst regenerations and thereby increases catalyst lifetime. Moreover, in preferred embodiments, the process of this invention beneficially produces the olefin oxide in a selectivity greater than about 90 mole percent, and preferably, greater than about 93 mole percent, over the sustained run time. Other oxidation products may include carbon dioxide, acrolein, acetone, acetaldehyde, and propionaldehyde, which as noted hereinafter are produced in acceptable quantities, if at all. As compared with prior art processes, the process of this invention can be operated at higher temperatures with essentially no decrease in olefin oxide selectivity and increase in partial oxidation by-products. Whereas in practice, prior art processes typically operate at a temperature from about 70° C. to about 170° C., the process of this invention, in practice, operates at a temperature from about 160° C. to about 300° C., thereby providing improved temperature flexibility. Since water is a co-product of the process invention, operation at higher temperatures, if desired, can provide a greater number of steam credits. Accordingly, the process of this invention can be integrated into a total plant design wherein heat derived from the steam is used to drive additional processes, for example, the separation of the olefin oxide from the co-product water. As compared with prior art processes, the process of this invention exhibits improved hydrogen efficiency, as measured by the cumulative water/olefin oxide molar ratio. In the subject invention, a cumulative water/olefin oxide molar ratio of less than about 8/1, and preferably, less than about 6/1, can be achieved over the total run time. The process of this invention can be conducted advantageously at a lower gold loading on the titanium-containing support without loss of catalyst activity, as compared with prior art processes. A gold loading from about 10 parts per million (ppm) to about 20,000 ppm, and preferably, from about 50 ppm to about 1,000 ppm, can be employed to economic advantage.

In a second aspect, this invention provides for a novel catalyst composition comprising gold nanoparticles deposited on particles of a nanoporous titanium-containing support, the catalyst being prepared by a process comprising depositing a gold-ligand cluster complex onto a nanoporous titanium-containing support under conditions sufficient to form a catalyst precursor, and then heating and/or chemically treating the catalyst precursor under conditions sufficient to form the catalyst composition.

In a third aspect, this invention provides for a method of preparing the aforementioned catalyst composition of this invention, the method comprising depositing a gold-ligand cluster complex onto a nanoporous titanium-containing support under conditions sufficient to form a catalyst precursor composition, and then heating and/or chemically treating the catalyst precursor composition under conditions sufficient to form a catalyst composition comprising gold nanoparticles deposited on particles of a nanoporous titanium-containing support.

In a fourth aspect, this invention provides for a catalyst precursor composition comprising a gold-ligand cluster complex deposited on particles of a nanoporous titanosilicate support.

The catalyst precursor composition of this invention is beneficially employed to prepare the catalyst composition of this invention, which itself can be effectively employed in the aforementioned hydro-oxidation process wherein an olefin having three or more carbon atoms is converted directly and selectively with oxygen in the presence of hydrogen to the corresponding olefin oxide.

DRAWINGS

FIG. 1 provides a graph of propylene conversion versus time and a graph of selectivity to propylene oxide versus time in a process of this invention illustrated in Example 1, wherein propylene is oxidized by oxygen in the presence of hydrogen and in the presence of a catalyst embodiment of this invention prepared from a $Au_9$-ligand cluster compound.

Figure 2:
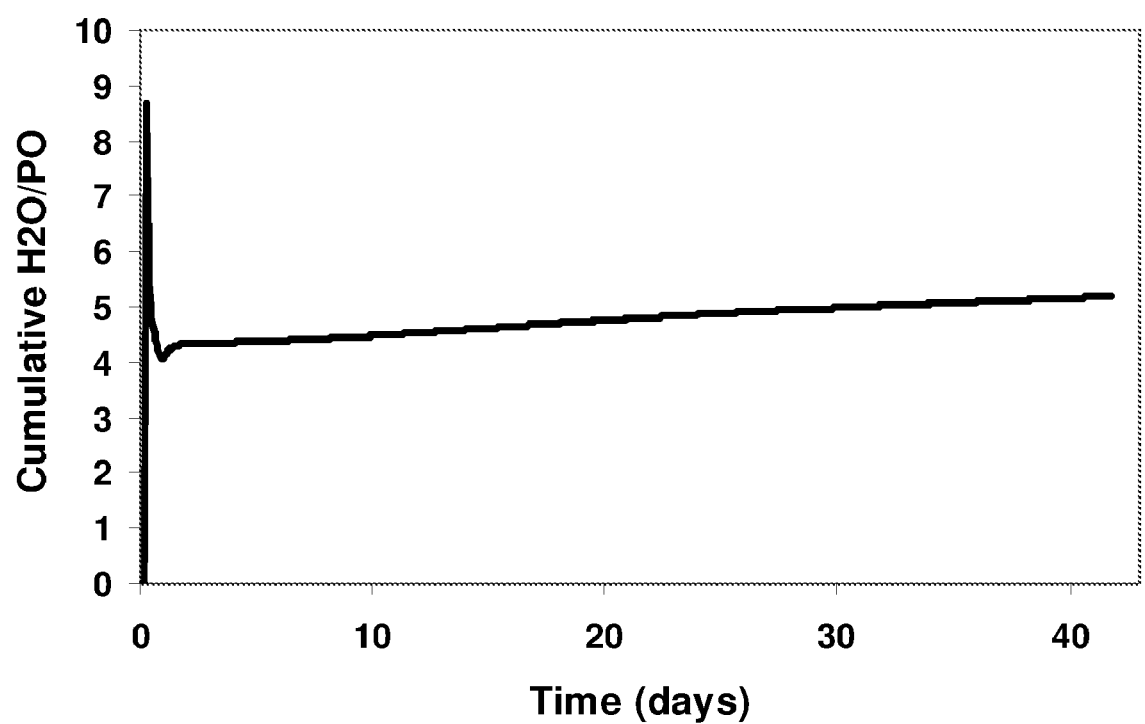

FIG. 2 provides a graph of cumulative molar ratio of water to propylene oxide versus time for the process embodiment illustrated in Example 1.

Figure 3:
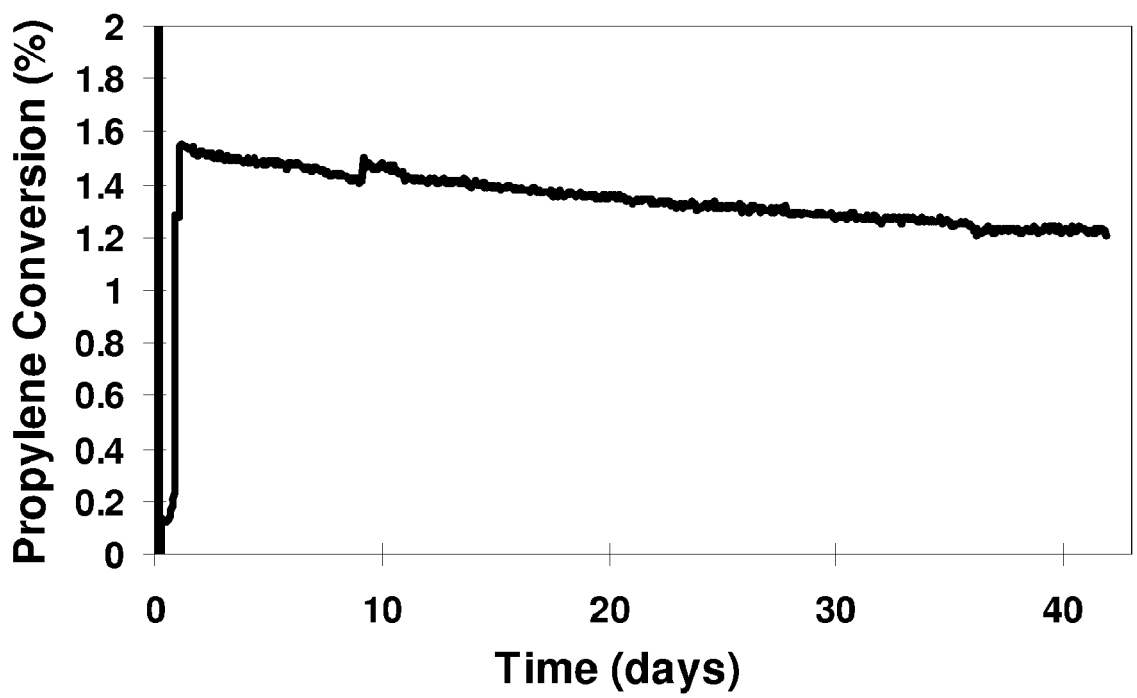
Figure 3:
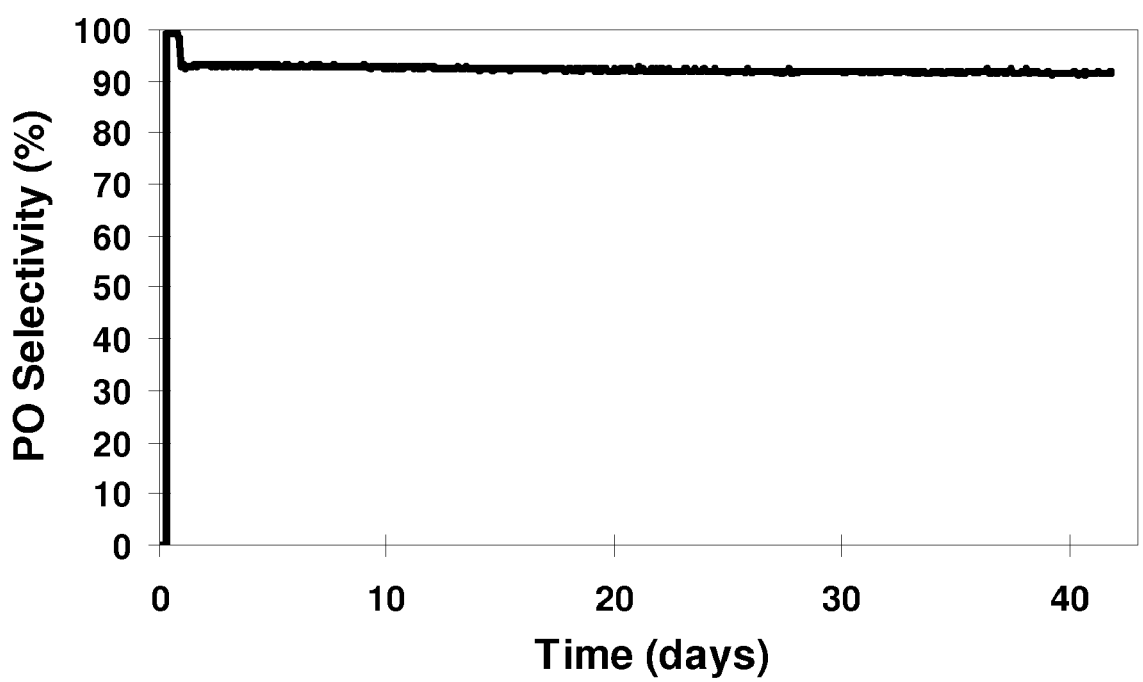

FIG. 3 provides a graph of propylene conversion versus time and a graph of selectivity to propylene oxide versus time in a process of this invention illustrated in Example 2 using a catalyst embodiment of this invention prepared from a $Au_9$-ligand cluster compound.

Figure 4:
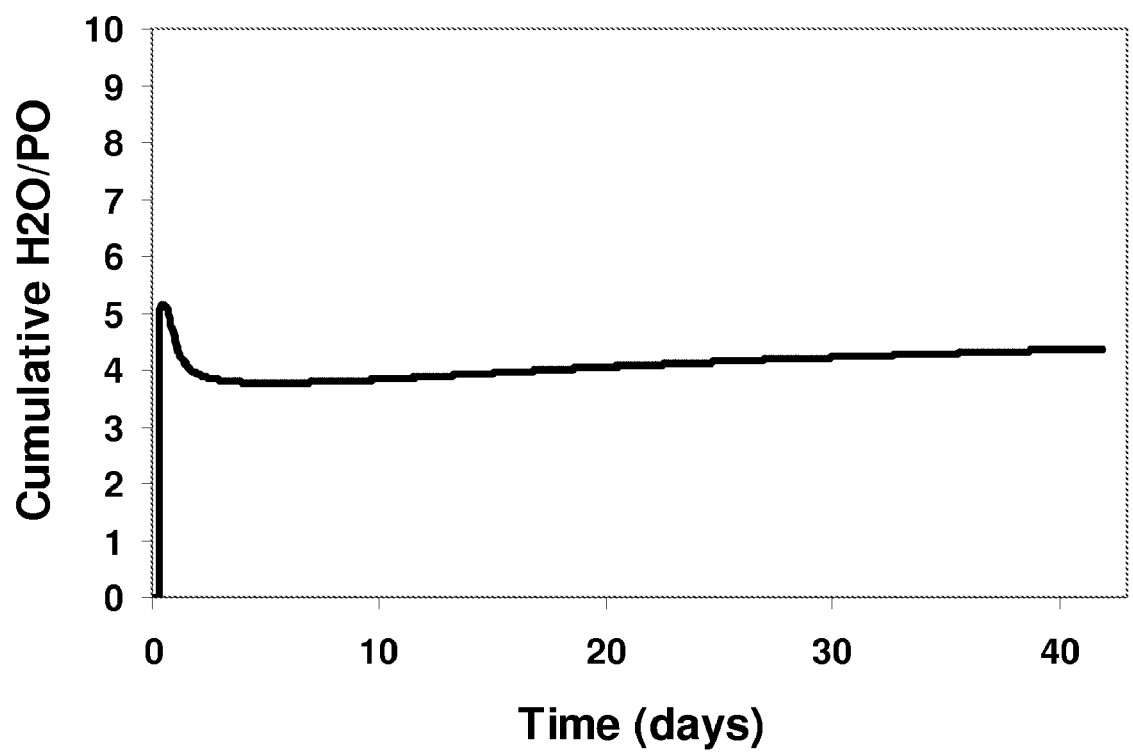

FIG. 4 provides a graph of cumulative molar ratio of water to propylene oxide versus time in the process embodiment illustrated in Example 2.

Figure 5:
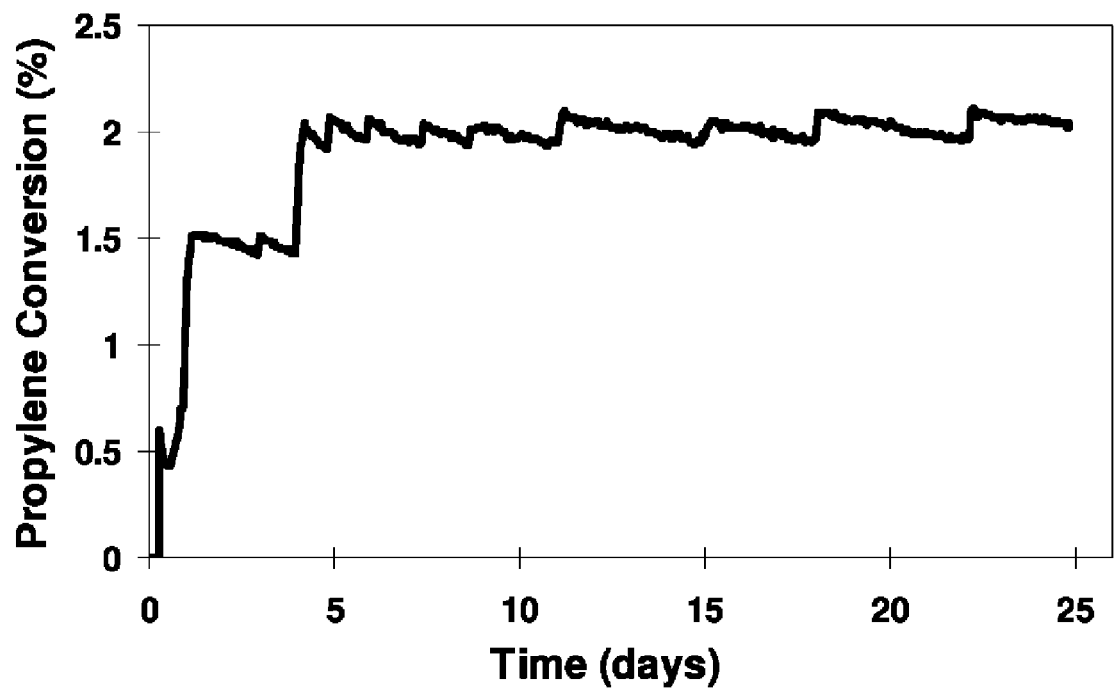
Figure 5:
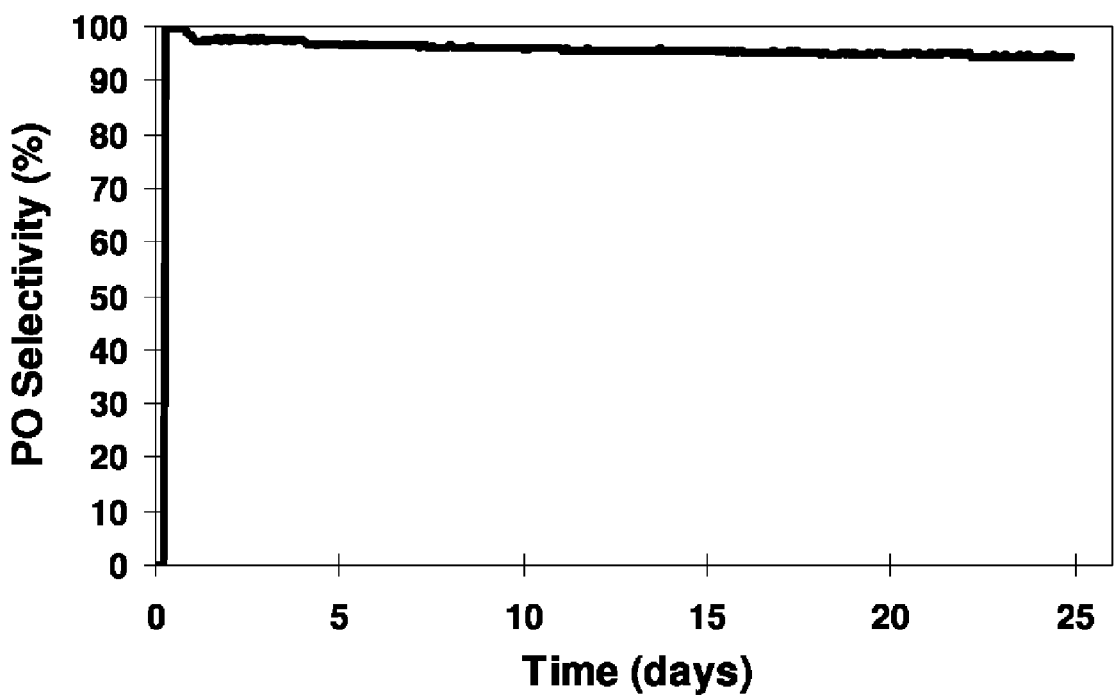

FIG. 5 provides a graph of propylene conversion versus time and a graph of selectivity to propylene oxide versus time in a process of this invention illustrated in Example 3 using a catalyst embodiment of this invention prepared from a Nanogold® brand Au-ligand cluster complex.

Figure 6:
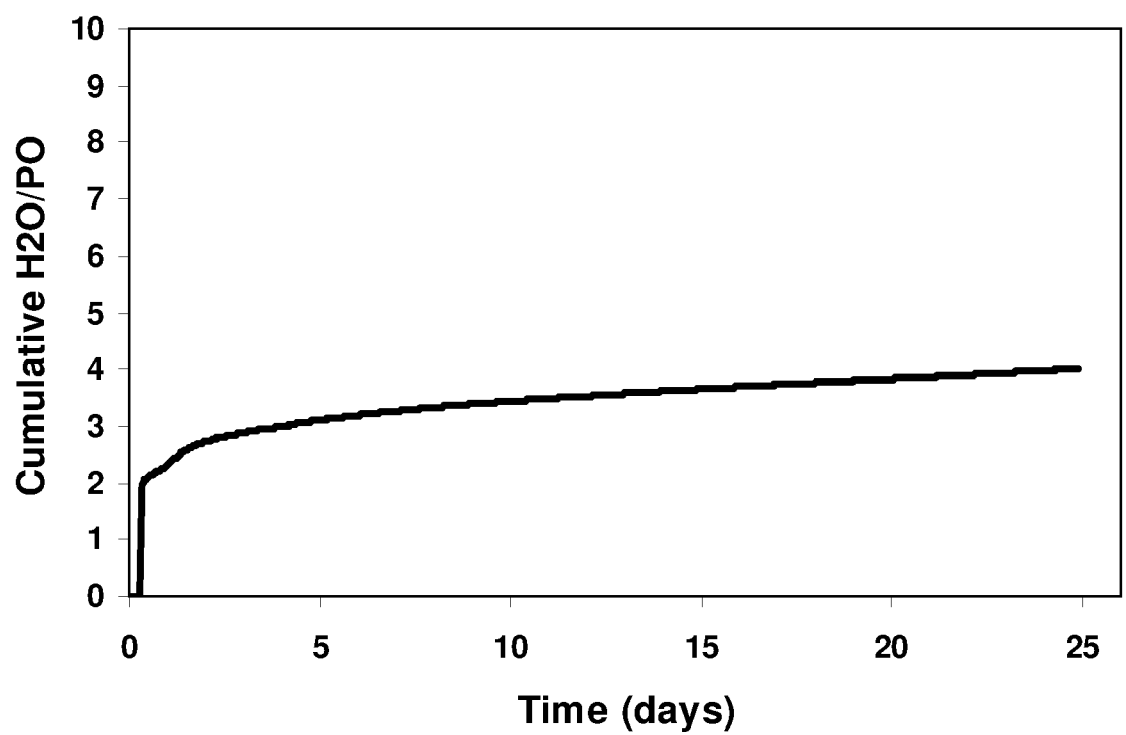

FIG. 6 provides a graph of cumulative molar ratio of water to propylene oxide versus time in the process embodiment illustrated in Example 3.

Figure 7:
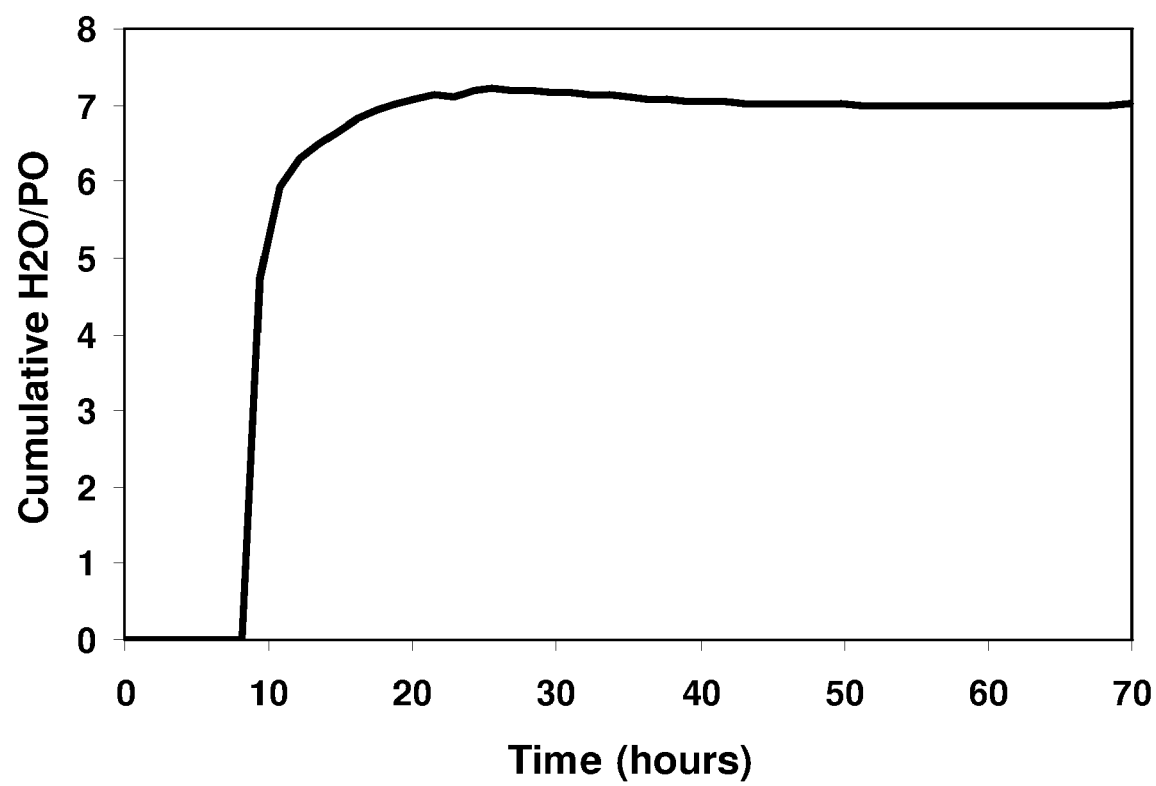

FIG. 7 provides a graph of cumulative molar ratio of water to propylene oxide versus time in a process embodiment illustrated in Example 4, wherein propylene is reacted with oxygen in the presence of hydrogen and a catalyst prepared from a mixed Pt—$Au_6$ cluster complex.

Figure 8:
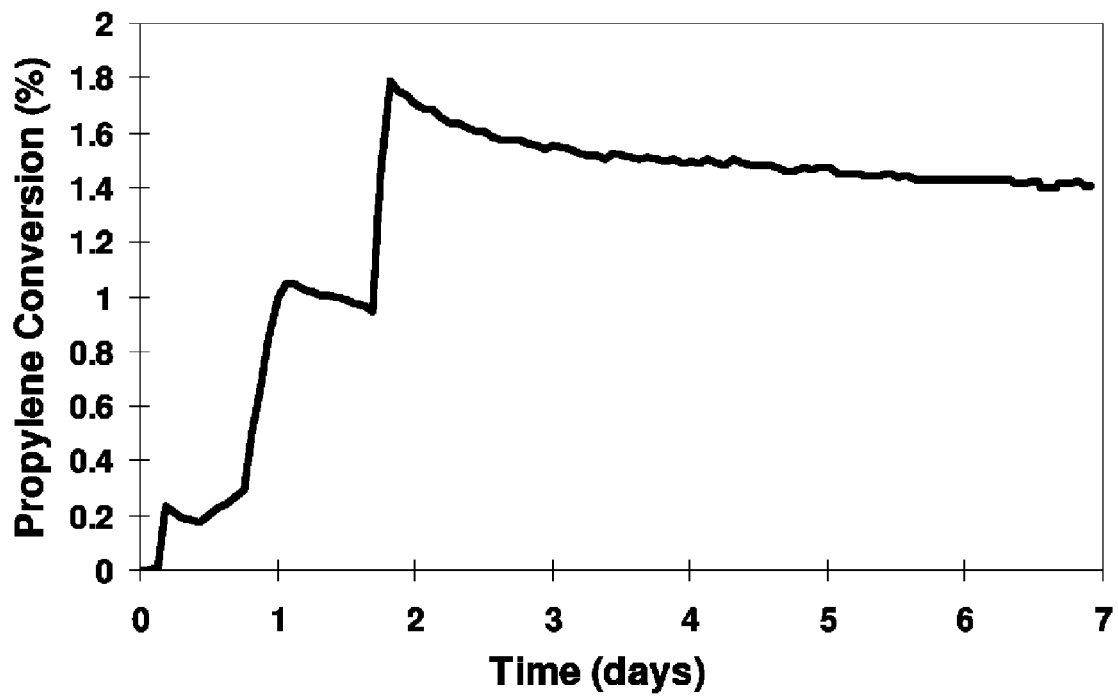
Figure 8:
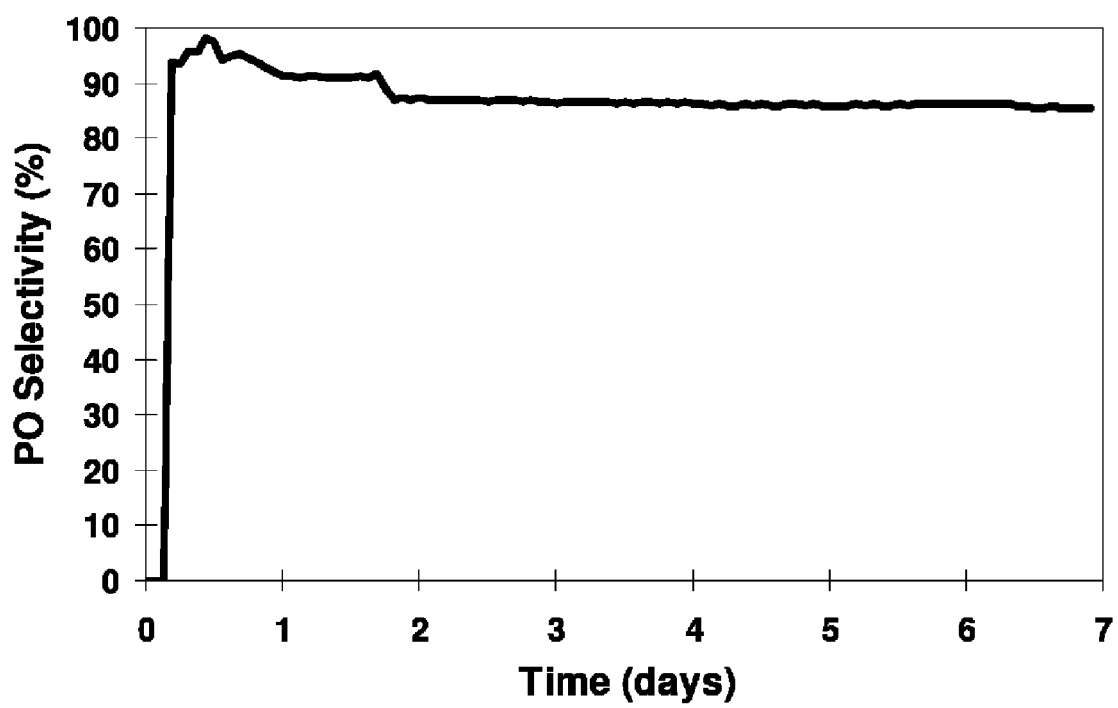

FIG. 8 provides a graph of propylene conversion versus time and a graph of selectivity to propylene oxide versus time in a process of this invention illustrated in Example 5 using a catalyst embodiment of this invention prepared from Positively Charged Nanoprobes brand Au-ligand cluster complex.

Figure 9:
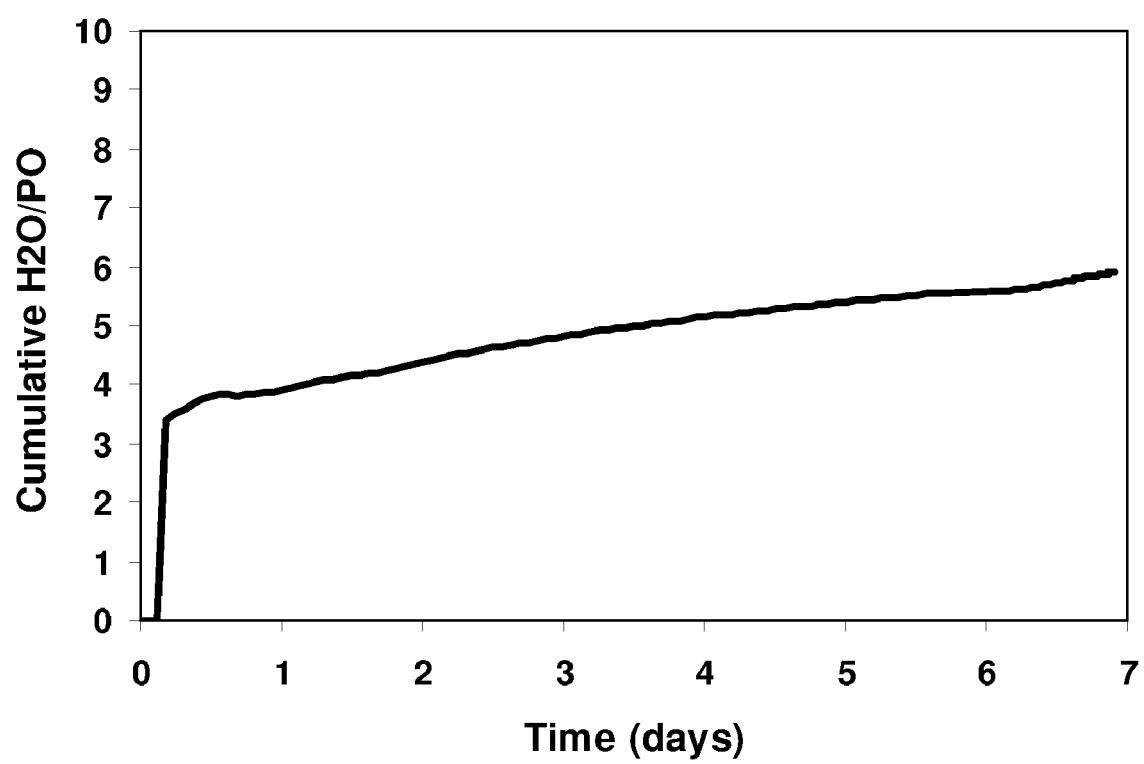

FIG. 9 provides a graph of cumulative molar ratio of water to propylene oxide versus time in the process embodiment illustrated in Example 5.

Figure 10:
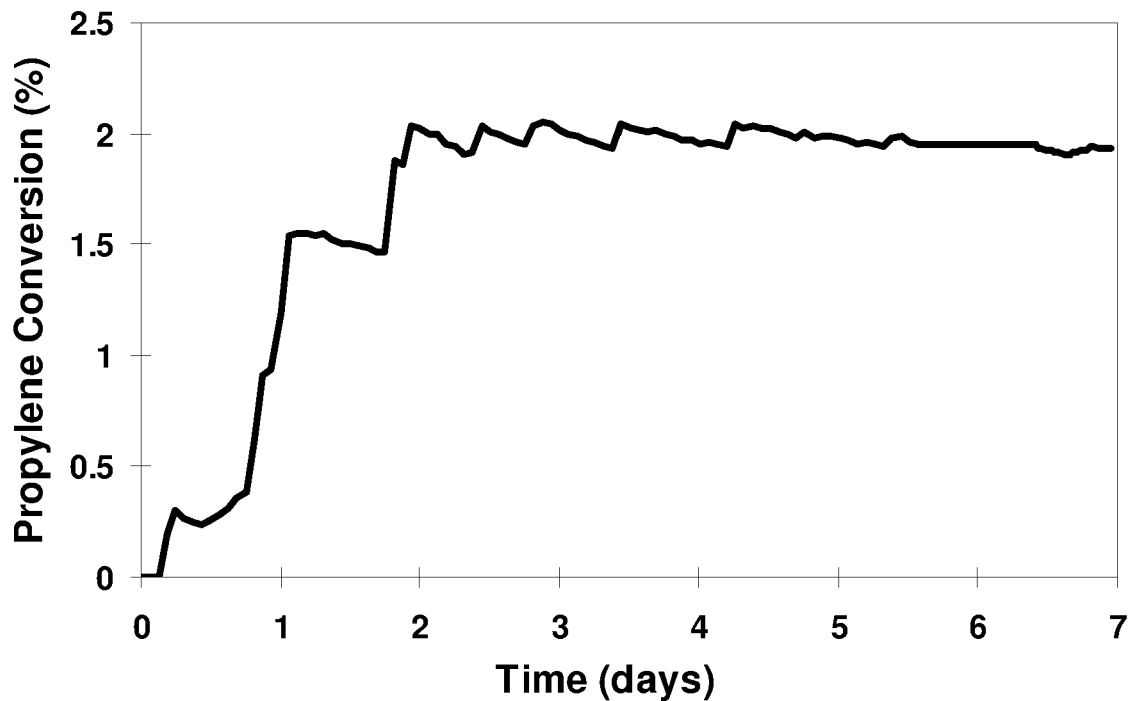
Figure 10:
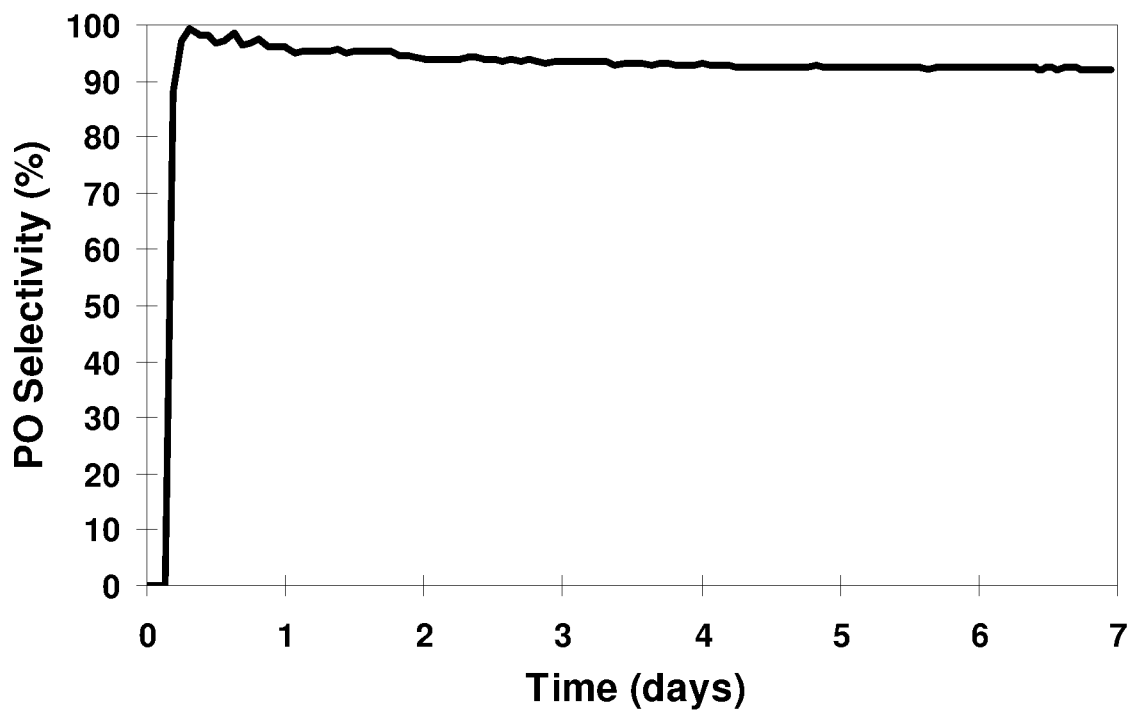

FIG. 10 provides a graph of propylene conversion versus time and a graph of selectivity to propylene oxide versus time in a process of this invention illustrated in Example 6 using a catalyst embodiment of this invention prepared from Negatively Charged Nanoprobes brand Au-ligand cluster complex.

Figure 11:
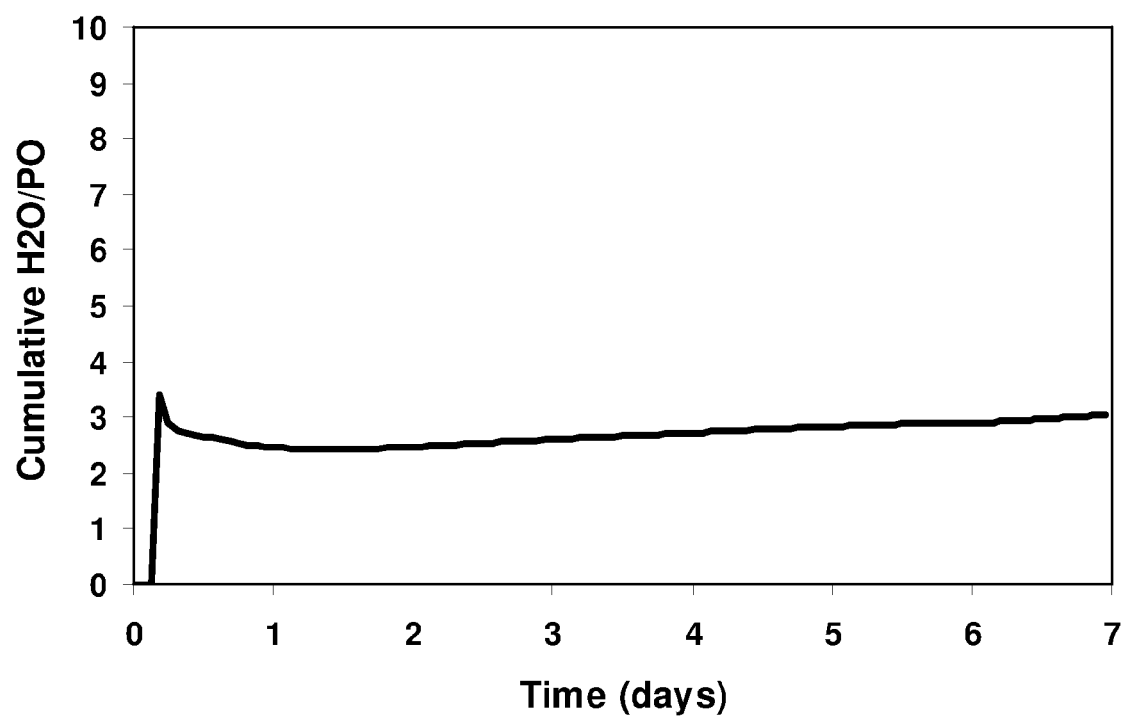

FIG. 11 provides a graph of cumulative molar ratio of water to propylene oxide versus time in the process embodiment illustrated in Example 6.

Figure 12:
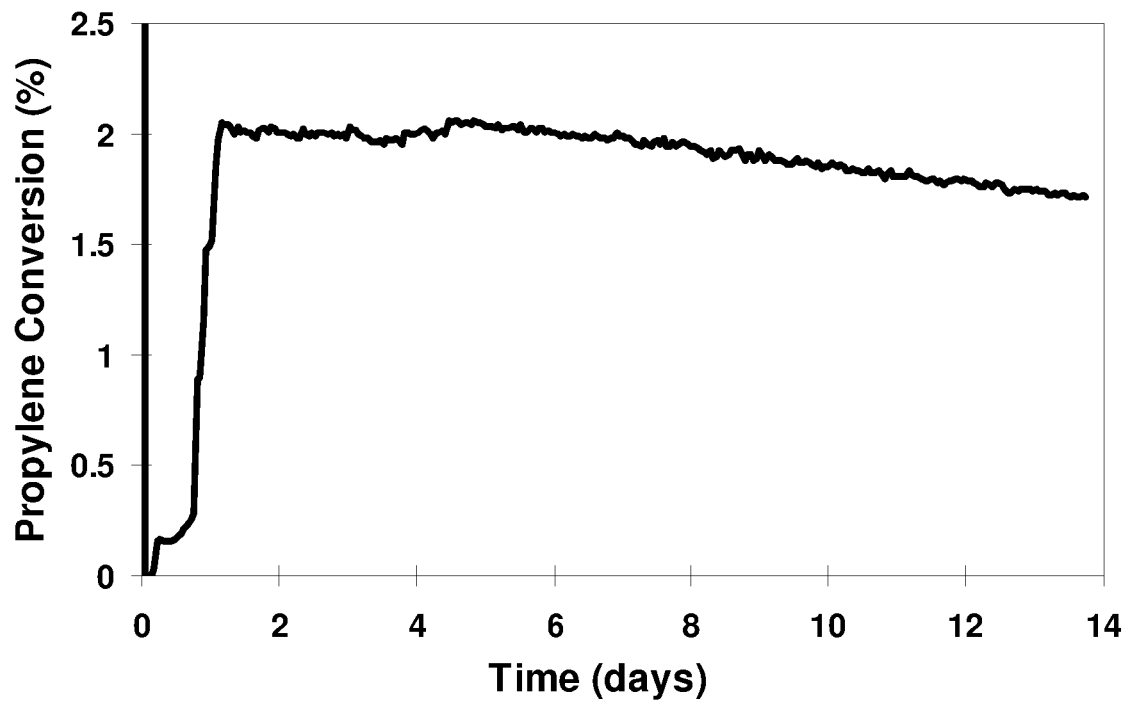
Figure 12:
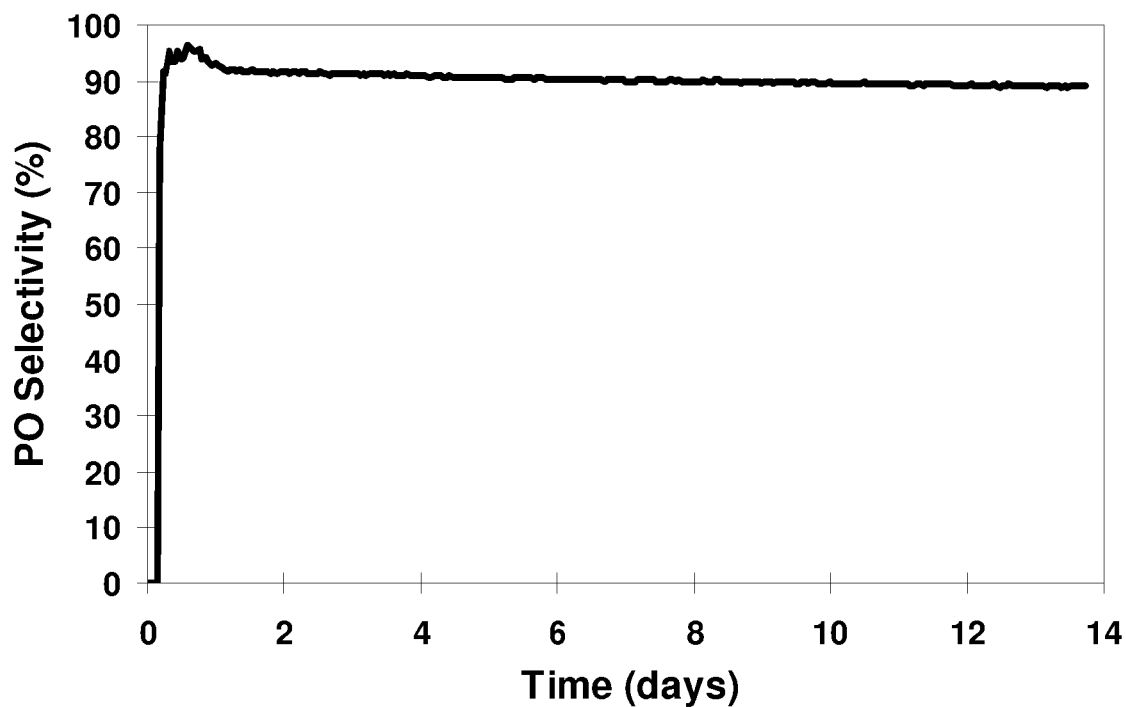

FIG. 12 provides a graph of propylene conversion versus time and a graph of selectivity to propylene oxide versus time in a process of this invention illustrated in Example 7 using a catalyst embodiment of this invention prepared from a $Au_{55}$-ligand cluster complex.

Figure 13:
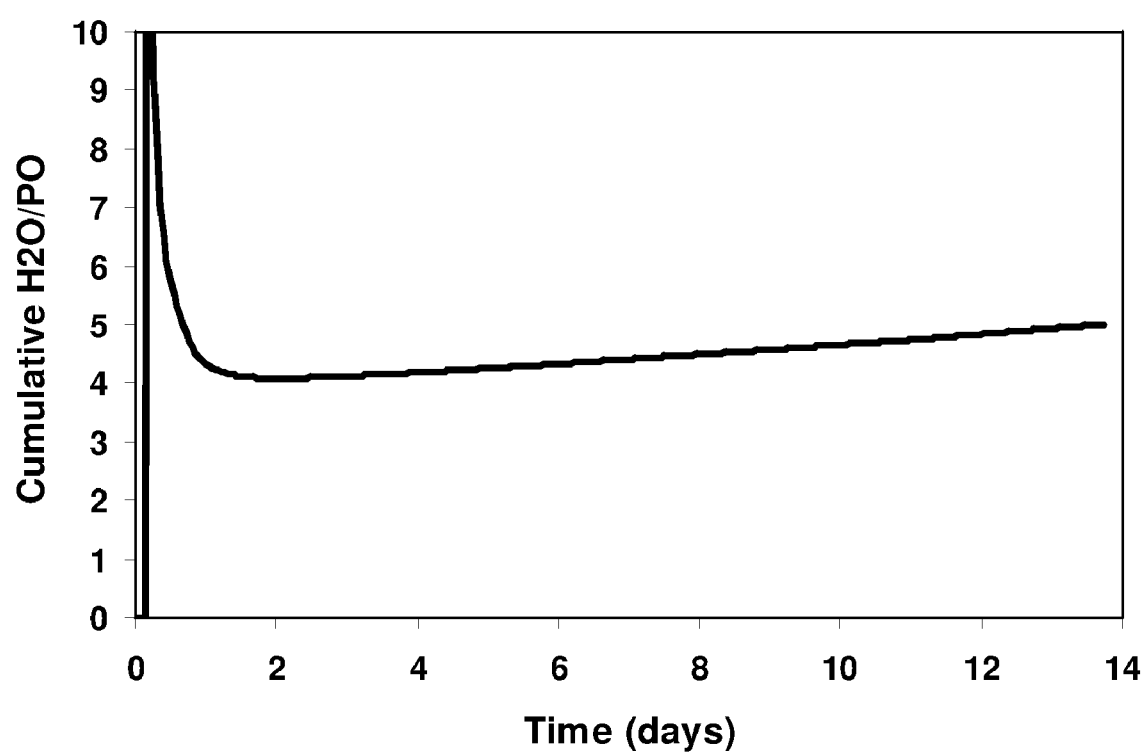

FIG. 13 provides a graph of cumulative molar ratio of water to propylene oxide versus time in the process embodiment illustrated in Example 7.

Figure 14:
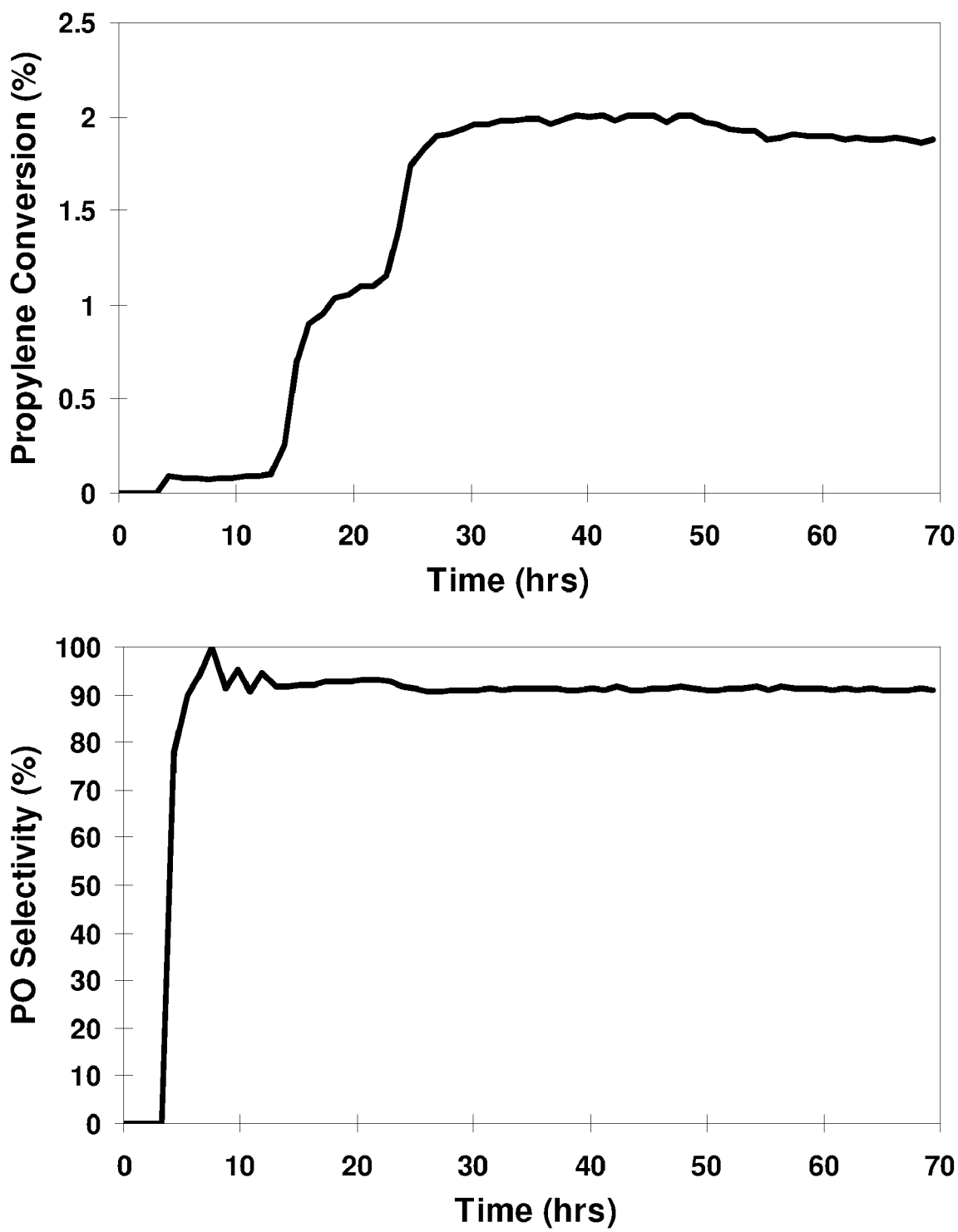

FIG. 14 provides a graph of propylene conversion versus time and a graph of selectivity to propylene oxide versus time in a process of this invention illustrated in Example 8 using a catalyst embodiment of this invention prepared from a Nanogold® brand Au-ligand cluster complex.

Figure 15:
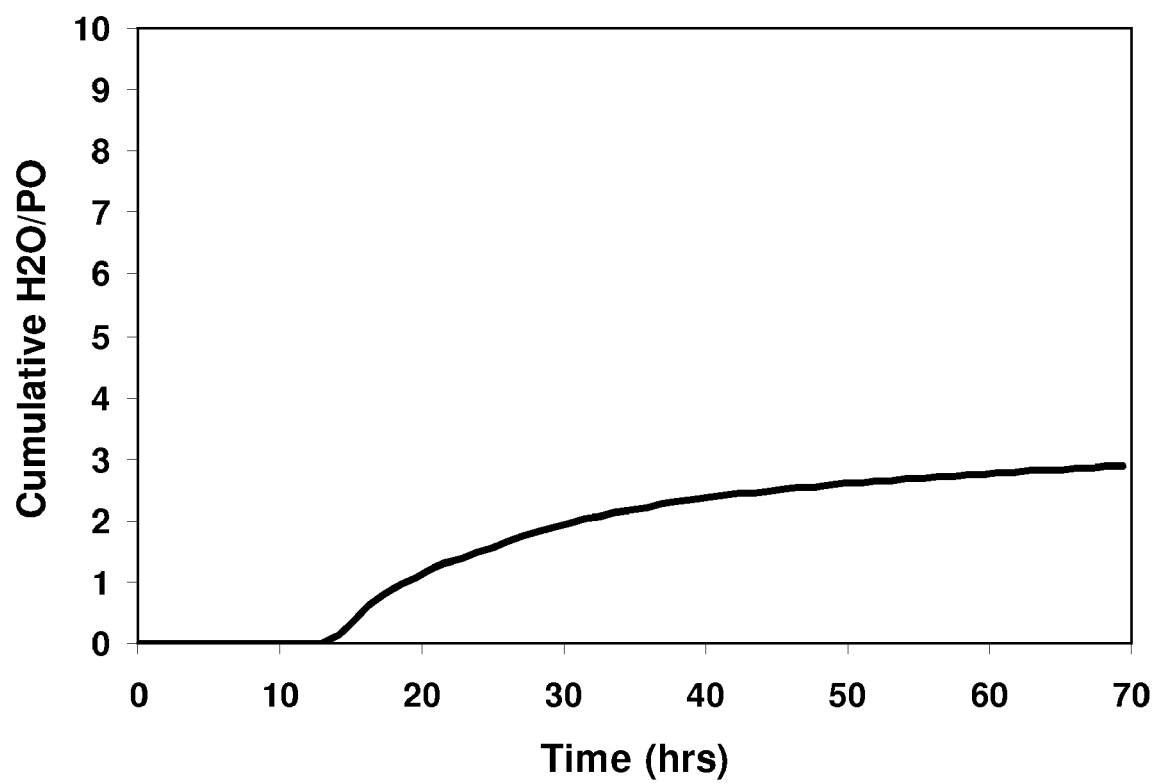

FIG. 15 provides a graph of cumulative molar ratio of water to propylene oxide versus time in the process embodiment illustrated in Example 8.

Figure 16:
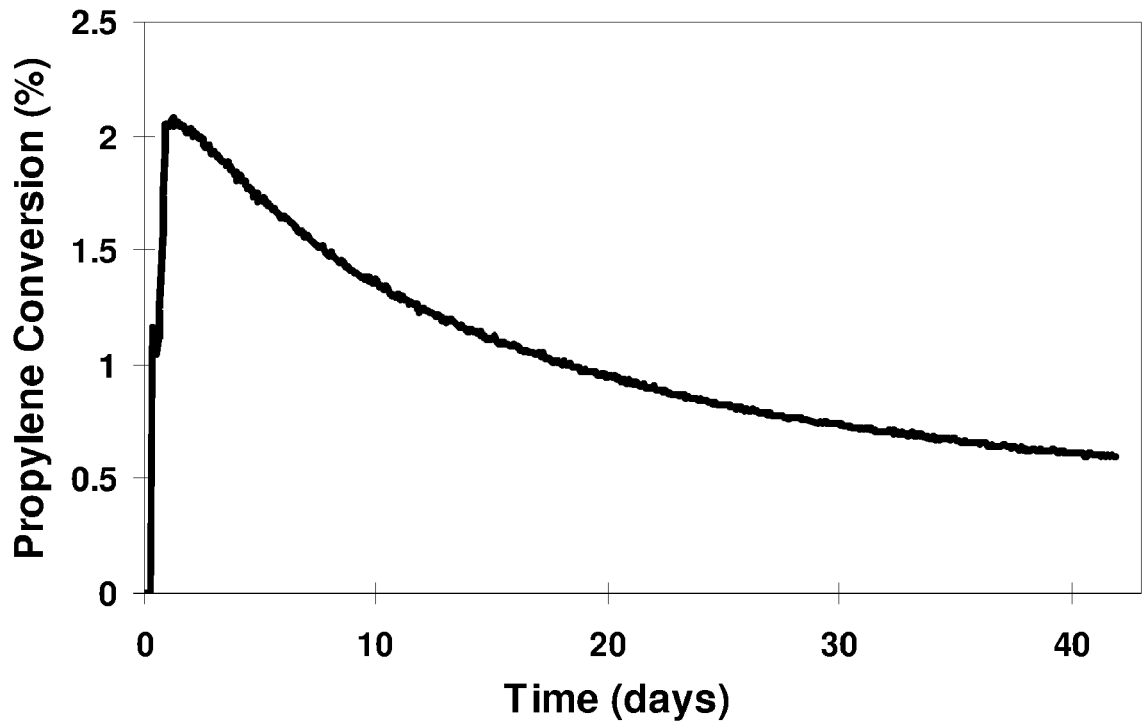
Figure 16:
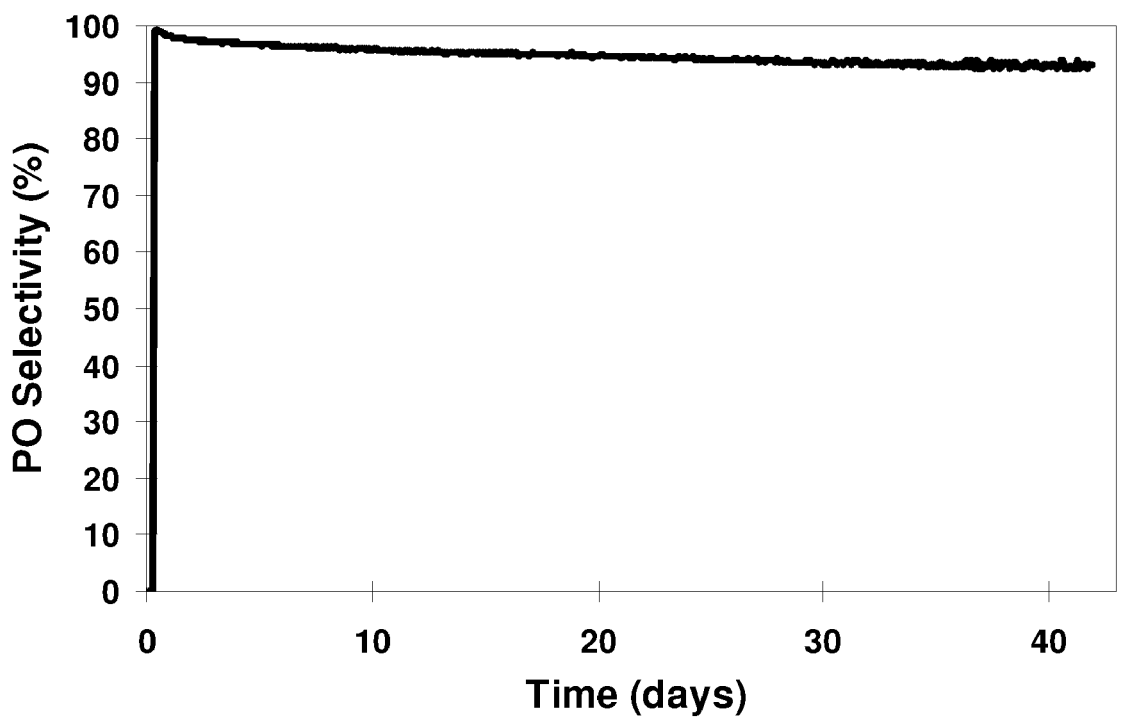

FIG. 16 provides a graph of propylene conversion versus time and a graph of selectivity to propylene oxide versus time in a comparative process using a catalyst containing chloroauric acid, as described in Comparative Experiment 1.

Figure 17:
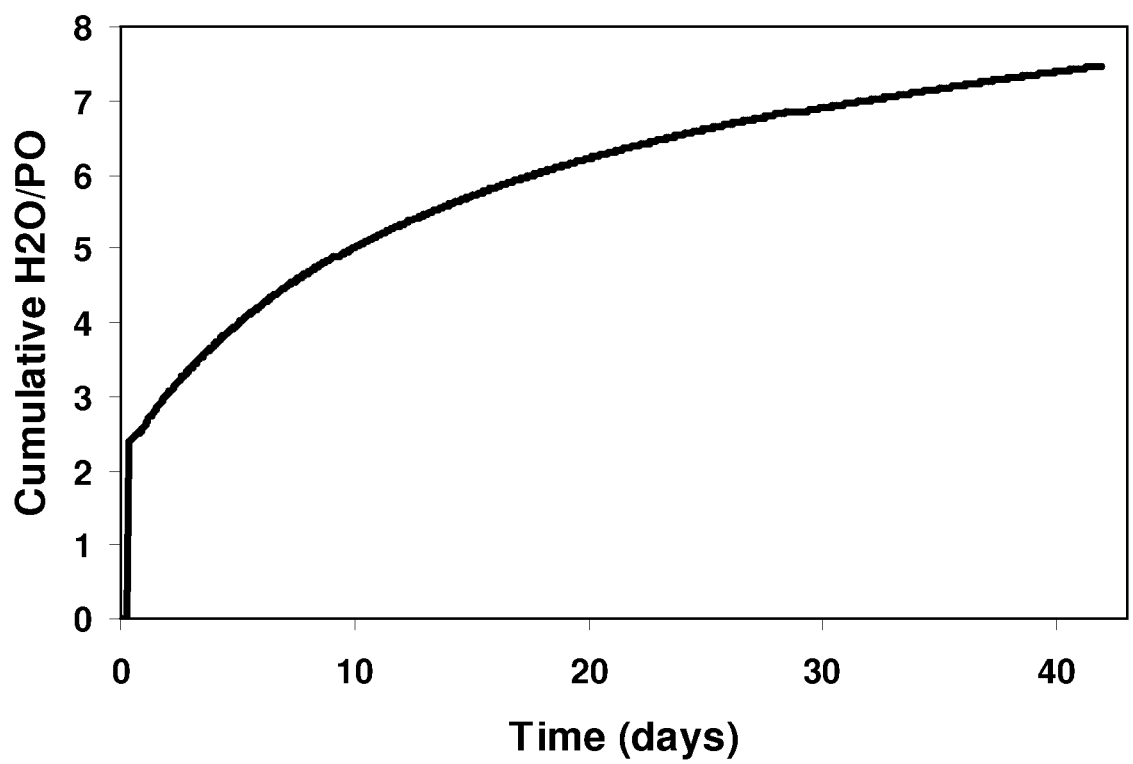

FIG. 17 provides a graph of cumulative molar ratio of water to propylene oxide versus time in the comparative process illustrated in Comparative Experiment 1.

Figure 18:
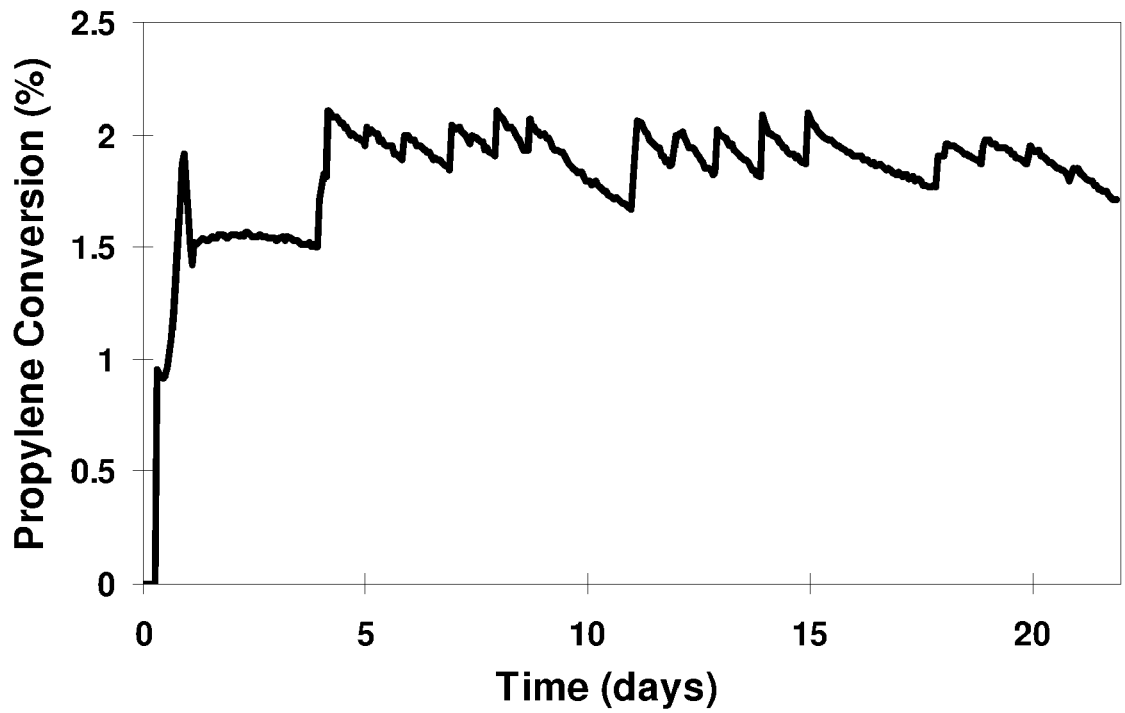
Figure 18:
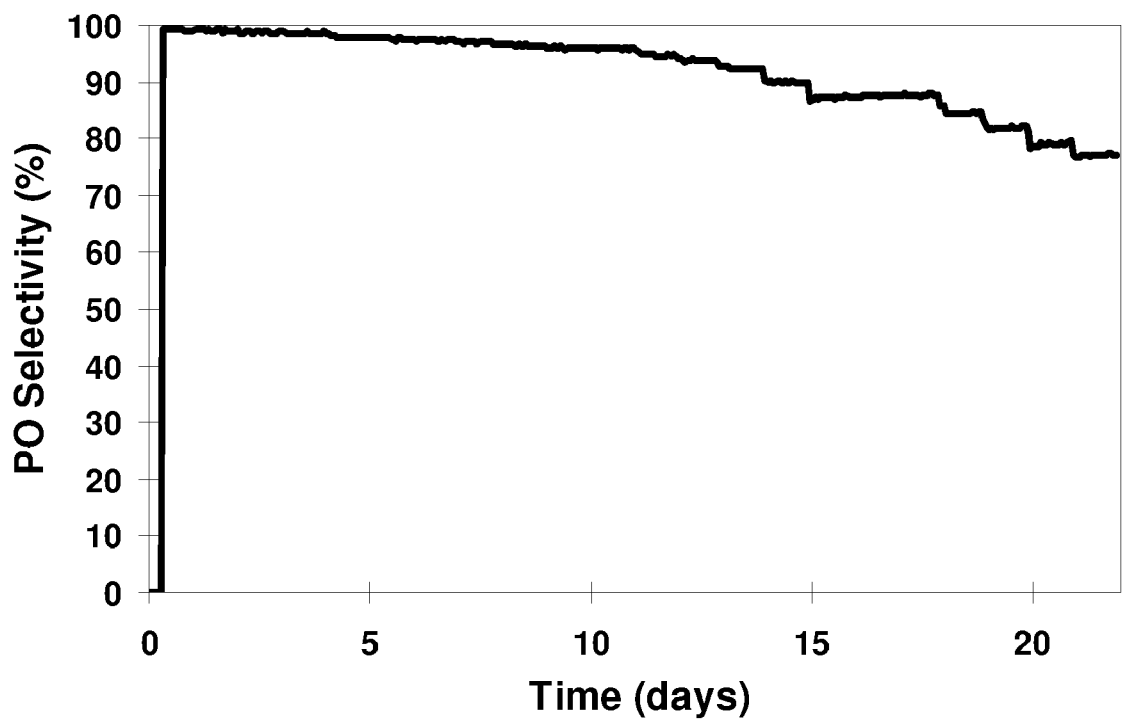

FIG. 18 provides a graph of propylene conversion versus time and a graph of selectivity to propylene oxide versus time in a comparative process using a catalyst containing chloroauric acid, as described in Comparative Experiment 2.

Figure 19:
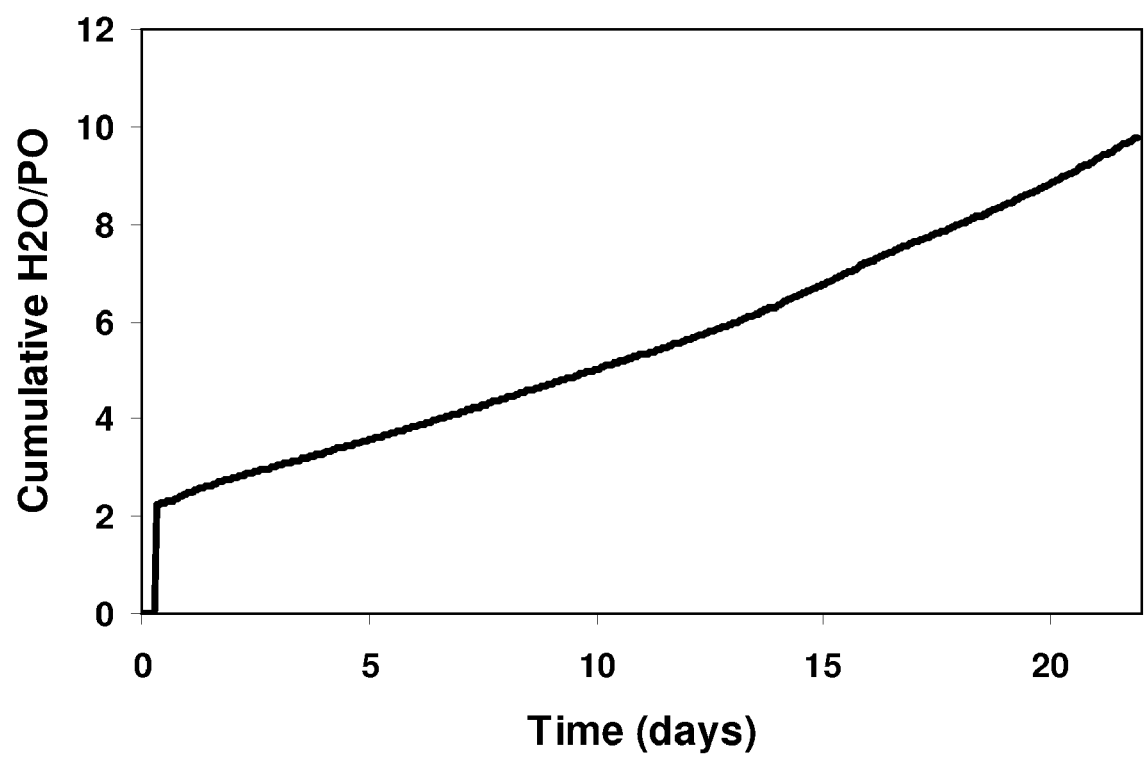

FIG. 19 provides a graph of cumulative molar ratio of water to propylene oxide versus time in the comparative process illustrated in Comparative Experiment 2.

DETAILED DESCRIPTION OF THE INVENTION

The novel hydro-oxidation process of this invention comprises contacting an olefin having three or more carbon atoms with oxygen in the presence of hydrogen and a hydro-oxidation catalyst under process conditions sufficient to prepare the corresponding olefin oxide. Optionally, the reactants comprising the olefin, oxygen, and hydrogen may be fed with one or more diluents, as described hereinbelow. The relative molar quantities of olefin, oxygen, hydrogen, and optional diluent can be any that are sufficient to prepare the desired olefin oxide. In a preferred embodiment of this invention, the olefin is a $C_{3-12}$ olefin, and it is converted to the corresponding $C_{3-12}$ olefin oxide. In a more preferred embodiment, the olefin is a $C_{3-8}$ olefin, and it is converted to the corresponding $C_{3-8}$ olefin oxide. In a most preferred embodiment, the olefin is propylene, and the olefin oxide is propylene oxide.

The hydro-oxidation catalyst employed in the process of this invention comprises gold nanoparticles deposited on particles of a nanoporous titanium-containing support, the catalyst being prepared by a process comprising depositing a gold-ligand cluster complex onto a nanoporous titanium-containing support under conditions sufficient to form a catalyst precursor, and then heating and/or chemically treating the catalyst precursor under conditions sufficient to form the catalyst.

For the purposes of this invention, the term "gold nanoparticles" broadly refers to gold particles having a diameter (or largest dimension in case of non-spherical particles) ranging from greater than about 0.6 nm to less than about 50 nm, preferably, from greater than about 0.7 nm to less than about 10 nm.

For the purposes of this invention, the words "titanium-containing support" refer to any solid wherein titanium is an integral component of the solid's framework structure, or wherein titanium is grafted onto a solid framework structure, or wherein a combination of framework and grafted titanium is present. The word "nanoporous" as it refers to the titanium-containing support refers to the presence of channels, pores and/or cavities within the support's framework structure; said channels, pores or cavities having a diameter (or largest dimension) from about 0.2 nm to about 50 nm. No limit is made on the distribution of the channels, pores, and/or cavities, which may be regularly or irregularly distributed throughout the solid framework. The channels themselves may be one, two, or three dimensional.

As used herein, the term "ligand" refers to any organic or inorganic, neutral molecule or charged ion that is bonded to one or more metal atoms, in this case, gold or any other metal in the catalyst, such as silver or noble metals, such as palladium or platinum. As used herein, the word "ligand" includes singular and plural, and thus may include a cluster complex containing only one ligand or a cluster complex containing two or more ligands, which may be the same or different.

The term "complex" as used herein means a coordination compound formed by the union of one or more electronically rich molecules and/or ions (ligand) with one or more electronically poor atoms or ions (e.g., metal). In this case, the electronically poor atom(s) or ion(s) is/are gold, or a combination of gold and silver, or a combination of gold and a noble metal, or a combination of gold, silver, and a noble metal, as explained hereinafter. This statement does not imply that all of the gold or other metal atoms in the cluster complex are electronically poor. Some of the gold and/or other metal atoms may be electronically poor and bound to one or more ligands, while other gold and/or metal atoms may not be electronically poor and may be bound to other metal atoms but not to ligands.

As used herein, the term "cluster" refers to a collection or group of gold atoms comprising a plurality of two or more gold atoms.

In one preferred embodiment, the gold-ligand cluster complex has a diameter (or largest dimension) larger than the pore size of the nanoporous titanium-containing support. Such a preferred embodiment substantially ensures that the gold-ligand cluster complex and, consequently, the gold nanoparticles cannot enter the pores or channels or cavities of the nanoporous titanium-containing support and, therefore, remain substantially on the exterior surface of the support.

In another preferred embodiment, the gold-ligand cluster complex comprises a gold-ligand cluster complex having one or more ligands selected from the group consisting of amines, imines, amides, imides, phosphines, thiols, thiolates, and mixtures thereof. In another preferred embodiment, the gold-ligand cluster complex comprises a gold-organophosphorus ligand cluster complex, more preferably, a gold-organophosphine ligand cluster complex.

In another preferred embodiment, the titanium-containing support comprises a nanoporous titanosilicate, more preferably, a nanoporous titanosilicate of the MFI crystallographic structure. The titanosilicate of MFI structure has a maximum pore size of about 0.54 nm +/−0.04 nm. In a more preferred embodiment wherein the nanoporous titanosilicate has an MFI structure, the gold-ligand cluster complex preferably has a diameter (or largest dimension) greater than about 0.54 nm (5.4 Angstroms).

In yet another preferred embodiment, the hydro-oxidation catalyst further comprises a promoter, defined as any elemental metal or metallic ion that enhances the performance of the catalyst, as detailed hereinafter. More preferably, the promoter is selected from silver, Group 1, Group 2, the lanthanide rare earth and actinide elements of the Periodic Table, their salts, and/or other compounds thereof, as well as mixtures thereof, as referenced in the *CRC Handbook of Chemistry and Physics*, 75$^{th}$ ed., CRC Press, 1994.

In another aspect, this invention provides for a catalyst precursor composition comprising a gold-ligand cluster complex deposited on particles of a nanoporous titanosilicate support.

Any olefin containing three or more carbon atoms or mixture of such olefins can be employed in the process of this invention. Monoolefins are suitable, as are compounds containing two or more olefinic bonds, such as dienes. The olefin can be a simple hydrocarbon containing only carbon and hydrogen atoms; or alternatively, the olefin can be substituted at any of the carbon atoms with an inert substituent. The term "inert", as used herein, requires the substituent to be substantially non-reactive in the process of this invention. Suitable inert substituents include, but are not limited to, halides, ether, ester, alcohol, and aromatic moieties; preferably, chloro, $C_{1-12}$ ether, $C_{1-12}$ ester, and $C_{1-12}$ alcohol moieties, and $C_{6-12}$ aromatic moieties. Non-limiting examples of olefins which are suitable for the process of this invention include propylene, 1-butene, 2-butene, 2-methylpropene, 1-pentene, 2-pentene, 2-methyl-1-butene, 2-methyl-2-butene, 1-hexene, 2-hexene, 3-hexene, and analogously, the various isomers of methylpentene, ethylbutene, heptene, methylhexene, ethylpentene, propylbutene, the octenes, including preferably 1-octene, and other higher analogues of these; as well as butadiene, cyclopentadiene, dicyclopentadiene, styrene, α-methylstyrene, divinylbenzene, allyl alcohol, allyl ether, allyl ethyl ether, allyl butyrate, allyl acetate, allyl benzene, allyl phenyl ether, allyl propyl ether, and allyl anisole. Preferably, the olefin is an unsubstituted or substituted $C_{3-12}$ olefin, more preferably, an unsubstituted or substituted $C_{3-8}$ olefin. Most preferably, the olefin is propylene. Many of the aforementioned olefins are available commercially; others can be prepared by chemical processes known to those skilled in the art.

The quantity of olefin employed can vary over a wide range provided that the corresponding olefin oxide is produced in the process. Generally, the quantity of olefin depends upon the specific process features, including for example, the design of the reactor, the specific olefin, and economic and safety considerations. Those skilled in the art will know how to determine a suitable range of olefin concentrations for the specific process features. In light of the disclosure herein, the quantity of olefin is typically greater than about 1, preferably, greater than about 5, and more preferably, greater than about 10 mole percent, based on the total moles of olefin, oxygen, hydrogen, and optional diluent. Typically, the quantity of olefin is less than about 99, and preferably, less than about 80, and more preferably, less than about 60 mole percent, based on the total moles of olefin, oxygen, hydrogen, and optional diluent.

Oxygen is also required for the process of this invention. Any source of oxygen is acceptable, including air or essentially pure molecular oxygen. Other sources of oxygen may be suitable, including ozone and nitrogen oxides, such as nitrous oxide. Molecular oxygen is preferred. The quantity of oxygen employed can vary over a wide range provided that the quantity is sufficient for producing the desired olefin oxide. Preferably, the quantity of oxygen is greater than about 0.01, more preferably, greater than about 1, and most preferably greater than about 5 mole percent, based on the total moles of olefin, hydrogen, oxygen, and optional diluent. Preferably, the quantity of oxygen is less than about 30, more preferably, less than about 25, and most preferably less than about 20 mole percent, based on the total moles of olefin, hydrogen, oxygen, and optional diluent. Above about 20 mole percent, the concentration of oxygen may fall within the flammable range for olefin-hydrogen-oxygen mixtures.

Hydrogen is also required for the process of this invention. In the absence of hydrogen, the activity of the catalyst is significantly decreased. Any source of hydrogen can be fed to the process of this invention, including for example, molecular hydrogen obtained from the dehydrogenation of hydrocarbons and alcohols. In an alternative embodiment of this invention, the hydrogen may be generated in situ in the olefin oxidation reactor, for example, by dehydrogenating alkanes, such as propane or isobutane, or alcohols, such as isobutanol. Alternatively, hydrogen may be used to generate a catalyst-hydride complex or a catalyst-hydrogen complex which can provide the necessary hydrogen to the process. The trace quantity of hydrogen in air is too negligible to provide the necessary quantity of hydrogen to the process of this invention. A source of additional hydrogen must be fed to the process or generated in situ in the process.

Any quantity of hydrogen can be employed in the process provided that the amount is sufficient to produce the olefin oxide. Suitable quantities of hydrogen are typically greater than about 0.01, preferably, greater than about 0.1, and more preferably, greater than about 3 mole percent, based on the total moles of olefin, hydrogen, oxygen, and optional diluent. Suitable quantities of hydrogen are typically less than about 50, preferably, less than about 30, and more preferably, less than about 20 mole percent, based on the total moles of olefin, hydrogen, oxygen, and optional diluent.

In addition to the above reactants, it may be desirable to employ a diluent, although the use thereof is optional. Since the process of this invention is exothermic, a diluent beneficially provides a means of removing and dissipating the heat produced. In addition, the diluent provides an expanded concentration regime in which the reactants are non-flammable. The diluent can be any gas or liquid that does not inhibit the process of this invention. The specific diluent chosen will depend upon the manner in which the process is conducted. For example, if the process is conducted in a gas phase, then suitable gaseous diluents include, but are not limited to, helium, nitrogen, argon, methane, carbon dioxide, steam, and mixtures thereof. If the process is conducted in a liquid phase, then the diluent can be any oxidation stable and thermally stable liquid. Examples of suitable liquid diluents include aliphatic alcohols, preferably $C_{1-10}$ aliphatic alcohols, such as methanol and t-butanol; chlorinated aliphatic alcohols, preferably $C_{1-10}$ chlorinated alkanols, such as chloropropanol; chlorinated hydrocarbons, preferably $C_{1-10}$ chlorinated hydrocarbons, such as dichloroethane and chlorinated benzenes, including chlorobenzene and dichlorobenzene; aromatic hydrocarbons, preferably, $C_{6-15}$ aromatic hydrocarbons, such as benzene, toluene, and xylenes; ethers, preferably, $C_{2-20}$ ethers, including tetrahydrofuran and dioxane; as well as liquid polyethers, polyesters, and polyalcohols.

If a diluent is used in the gas phase, the amount of diluent is typically greater than about 0, preferably greater than about 0.1, and more preferably, greater than about 15 mole percent, based on the total moles of olefin, oxygen, hydrogen, and diluent. If a diluent is used in the gas phase, the amount of diluent is typically less than about 90, preferably, less than about 80, and more preferably, less than about 70 mole percent, based on the total moles of olefin, oxygen, hydrogen, and diluent. If a liquid diluent (or solvent) is used in the liquid phase, the amount of liquid diluent (or solvent) is typically greater than about 0, and preferably, greater than about 5 weight percent, based on the total weight of the olefin and diluent. If a liquid diluent is used in the liquid phase, the amount of liquid diluent is typically less than about 99, and preferably, less than about 95 weight percent, based on the total moles of olefin and diluent.

The concentrations of olefin, oxygen, hydrogen, and diluent disclosed hereinabove are suitably based on the reactor designs and process parameters disclosed herein. Those skilled in the art will recognize that concentrations other than those disclosed herein may be suitably employed in other various engineering realizations of the process.

The catalyst that is beneficially employed in the hydro-oxidation process of this invention comprises gold nanoparticles deposited on particles of a nanoporous titanium-containing support. The gold is present predominantly as metallic gold (elemental or zerovalent gold). In this context, the word "predominantly" means greater than about 80 percent, preferably, greater than about 85 percent, and more preferably, greater than about 90 percent metallic gold, by weight. Oxidized gold may be present in any oxidation state from greater than 0 to +3, either as a transient species during the catalytic hydro-oxidation cycle or in some stabilized form. Any analytical technique that is capable of measuring oxidation states and/or their relative amounts can be employed to determine the oxidation state(s) of the gold including, for example, X-ray photoelectron spectroscopy (XPS) or Mie scattering measured on an ultraviolet-visible diffuse reflectance spectrometer (UV-VIS DRS). XPS may be preferred and can be collected on a Kratos Axis 165×PS instrument or a PHI 5400 XPS instrument, or any equivalent thereof.

High resolution transmission electron spectroscopy (HR-TEM) can be beneficially employed to visualize gold particles on the catalyst composition in its fresh or used form as well as on the catalyst precursor composition. Any high resolution transmission electron microscope having a point to point resolution of 2 Å, or greater resolution, can be employed for this purpose. TEM counting statistics are typically employed to determine the average or median particle size, depending upon one's preference. (The "average particle size" is calculated by dividing the sum of the sizes of all particles in the sample by the number of particles in the sample. The "median particle size" is that size about which 50 percent of the particles are smaller and 50 percent of the particles are larger in size.) For a reference discussing TEM counting statistics, see A. K. Dayte, et al., *Catalysis Today,* 111 (2000), 59-67, incorporated herein by reference. Typically, the catalyst composition of this invention comprises a distribution of gold nanoparticles ranging in diameter (or largest dimension in the case of non-spherical particles) from greater than about 0.6 nm, and preferably, greater than about 0.7 nm to typically less than about 50 nm, preferably, less than about 20 nm, more preferably less than about 10 nm, even more preferably, less than about 8 nm, as measured by HRTEM. In one most preferred embodiment, the median gold particle size of the fresh catalyst ranges from about 0.8 nm to less than about 8.0 nm, as measured by HRTEM. The gold nanoparticles are not limited to any specific morphology. Any shape may be found including, for example, bilayers, rafts, hemispheres, spheres, oblate forms (e.g., flattened spheres), cubooctahedra, and truncated variations thereof.

Additionally, X-ray absorption fine structure spectroscopy (XAFS) can be obtained on a synchrotron X-ray light source (e.g., Advanced Photon Source, Argonne National Laboratory or National Synchrotron Light Source, Brookhaven National Laboratory, USA) to provide information on the average or median gold particle size in any form of the catalyst (fresh or used) or the catalyst precursor. The technique depends upon the measurement of coordination number (or number of neighboring gold atoms), which is then correlated with gold particle size. XAFS's can also provide information on the average oxidation state of the gold.

In preferred embodiments of the catalyst of this invention wherein the support has a pore size between 0.2 nm and 1 nm, the gold nanoparticles are located substantially on the exterior or external surface of the particles of the nanoporous titanium-containing support. For the purposes of this invention, the "exterior surface" of the nanoporous titanium-containing support comprises the external surface or envelope surrounding the particles or agglomerates of the support. The exterior surface includes all prominences and also the surface of cracks that are wider than they are deep. In contrast, the "interior or internal surface" comprises the walls of all pores, channels, cavities, and cracks that are deeper than they are wide. With reference to the gold nanoparticles being substantially located on the exterior surface of the support in preferred embodiments of this invention, the term "substantially" means that greater than about 90 percent, and preferably, greater than about 95 percent of the gold nanoparticles are located on the exterior surface of the support. Accordingly, less than about 10 percent, and preferably, less than about 5 percent, of the gold nanoparticles are present on the interior surface of the titanium-containing support.

The size and location of the gold nanoparticles can be observed by transmission electron microscopy (TEM) or scanning transmission electron microscopy (STEM), preferably, by transmission electron microscopy tomography (TEM tomography). TEM tomography provides a three-dimensional structure determination by electron microscopy. The sample is viewed by TEM at different angles of rotation, for example 0°, 15°, 20°, 40°, etc.; and from the resulting compilation of pictures the skilled artisan can determine whether a particle of gold is located on an exterior surface or an interior wall. TEM tomography can be performed using an FEI Tecnai-12 TEM (FEI COMPANY™, Serial #D250) operated at 120 kV. The microscope is typically equipped with a CAMPUS© stage that is fully computer controlled. An FEI brand tomography software package can be used to control the imaging and titling conditions during the acquisition of the tilt series. The alignment of the tilt series and reconstruction of the 3-D volume can be accomplished with Inspect3D© software (FEI Company™). Amira© Software (version 3.1.1, FEI Company™) can be used for visualization and manipulation of the 3-D volume.

The following publications are provided for enablement of TEM and TEM tomography measurements, all publications incorporated herein by reference: Willams, D. B. and Carter, C. B., *Transmission Electron Microcopy I—Basics, Chapter 1*, Plenum Press, New York, 1996; FEI company, *Advanced Tecnai TEM software for easy acquisition, reconstruction and visualization*; Flannery, B. P., Deckmean, H. W., Robergy, W. G., and D'Amico, K. L., *Science* 1987, 237, 1439; Hoppe, W. and Hegerl, R., *Three-dimensional structure determination by electron microscopy (nonperiodic specimens)*, in Hawkes, P. W. (Ed.), *Computer Processing of Electron Microscope Images*, Springer, Berlin, Heidelberg, New York, 1980; Frank, J., *Three-dimensional Electron Microscopy of Macromolecular Assemblies*, Academic Press, San Diego, 1996; Midgley, P. A. and Weyland, M., "3D Electron Microscopy in the Physical Sciences: the Development of Z-contrast and EFTEM tomography," *Ultramicroscopy*, 2003, 96, 413-431.

The process of this invention beneficially provides for practical operation at lower gold loading on the catalyst, as compared with prior art processes. Generally, the gold loading is greater than about 10 ppm, preferably, greater than about 50 ppm, and more preferably, greater than about 100 ppm, based on the total weight of the catalyst composition. Typically, the gold loading is less than about 20,000 ppm, preferably, less than about 5,000 ppm, more preferably, less than about 1,000 ppm, based on the total weight of the catalyst composition.

The "titanium-containing support" can be any solid wherein titanium is an integral component of the solid's framework structure, or wherein titanium is grafted or deposited onto a solid structure, or wherein a combination of framework and grafted or deposited titanium is present. The word "nanoporous" as it describes the titanium-containing support refers to the presence of channels, pores and/or cavities within the support's framework structure, of a width (or largest dimension) ranging from about 0.2 nm to about 50 nm. Such porous structures possess micropores, taken as pore widths not exceeding about 2 nm, and mesopores, taken as pore widths between about 2 nm and 50 nm. Larger void spaces, between particles or interior to a particle, of a width greater than 50 nm are not included in the term "nanoporous." As mentioned earlier, the distribution of the channels, pores, and/or cavities can be regular or irregular; and the pores and/or channels may be one, two, or three dimensional. The titanium-containing support can be crystalline, quasi-crystalline, or amorphous. In such supports, the titanium exists essentially as non-metallic titanium.

The distribution of pore widths in the titanium-containing support can be determined from adsorption isotherms using, for example, nitrogen gas at the temperature of the boiling point of nitrogen at ambient atmospheric pressure. The surface area of the support can be determined by the Brunauer-Emmett-Teller (BET) gas adsorption method. For a more complete discussion of these techniques, refer to American National Standard Testing Method, ASTM D 3663-78 and to IUPAC, K. S. W. Sing, et al., "Reporting Physisorption Data for Gas/Solid Systems—with special Reference to the Determination of Surface Area and Porosity," Pure & Applied Chemistry, Vol. 57, No. 4 (1985), pp. 603-619, incorporated herein by reference. Generally, the nanoporous titanium-containing support possesses a surface area greater than about 5 $m^2/g$, preferably, greater than about 50 $m^2/g$, more preferably, greater than about 150 $m^2/g$, as determined by the BET method.

Suitable supports include, without limitation, titanium-containing amorphous and crystalline silicas, such as silicalite or MCM-41, aluminas, metallosilicates, such as, aluminosilicates and preferably titanosilicates, promoter metal silicates, such as, the silicates of Groups 1 and 2 and the lanthanide and actinide elements, and other refractory oxides or conventional support materials.

Also suitable as the support may be stoichiometric or non-stoichiometric promoter metal titanates of a crystalline or amorphous nature, having a surface area greater than about 5 $m^2/g$, non-limiting examples of which include such titanates of Group 1, Group 2, and the lanthanide and actinide metals. Suitably, the promoter metal titanate is selected from the group consisting of magnesium titanate, calcium titanate, barium titanates, strontium titanate, sodium titanate, potassium titanate, lithium titanate, cesium titanate, rubidium titanate, and the titanates of erbium, lutetium, thorium, and uranium. As a further suitable support, an amorphous or crystalline titanium oxide, including anatase, rutile, and brookite phases of titanium dioxide, having a surface area greater than about 5 $m^2/g$ can be suitably employed.

Preferred titanium-containing supports are described in WO 98/00413, WO 98/00414, WO 98/00415, and U.S. Pat. No. 6,255,499, all references incorporated herein by reference.

In those instances wherein titanium is affixed onto or in the support, the titanium loading can be any that gives rise to an active catalyst in the process of this invention. Typically, the titanium loading is greater than about 0.02 weight percent, preferably, greater than about 0.1 weight percent, based on the weight of the support including any binder as noted hereinafter. Typically, the titanium loading is less than about 35 weight percent, and preferably, less than about 10 weight percent, based on the weight of the support including any binder. It is to be understood that in cases wherein titanium is a stoichiometric component of the support, such as in promoter metal titanates, the weight percentage of titanium in the support can be higher than 35 weight percent.

In a more preferred embodiment, the support comprises a nanoporous titanosilicate, even more preferably, a titanosilicate zeolite. An even more preferred titanium-containing support comprises a nanoporous titanosilicate selected from TS-1, TS-2, Ti-beta, Ti-MCM-41, Ti-MCM-48, Ti-SBA-15, and Ti-SBA-3. A most preferred titanosilicate comprises a quasi-crystalline titanosilicate having an MFI structure, which is orthorhombic at room temperature (21° C.), as determined by X-ray diffraction (XRD). Such a support and its method of preparation are disclosed in U.S. Pat. No. 6,255,499, incorporated herein by reference.

The silicon to titanium atomic ratio (Si:Ti) of the preferred titanosilicate support can be any ratio that provides for an active and selective hydro-oxidation catalyst in the process of this invention. A generally advantageous Si:Ti atomic ratio is equal to or greater than about 5:1, preferably, equal to or greater than about 50:1. A generally advantageous Si:Ti atomic ratio is equal to or less than about 1,000:1, preferably, equal to or less than about 300:1.

Any combination or mixture of titanium-containing supports described hereinabove can be employed in the catalyst of this invention.

The titanium-containing support may be shaped into any form suitable for catalyst particles, for example, beads, pellets, spheres, honeycombs, monoliths, extrudates, and films. Optionally, the titanium-containing support can be extruded with, bound to, or supported on a second support for the purpose of binding together the catalyst particles and/or improving the catalyst's strength or attrition resistance. For example, it may be desirable to prepare a thin film of the titanium-containing support on a secondary support which is shaped into a bead, pellet, or extrudate. Suitable secondary supports include carbon and any refractory oxide, such as, silica, titania, alumina, aluminosilicates, and magnesia; ceramics, including ceramic carbides and nitrides, as well as any metallic support. Generally, the quantity of second support ranges from about 0 to about 95 weight percent, based on the combined weight of the catalyst (gold and titanium-containing support) and secondary support, with the following proviso. When the binder or secondary support is titania, then typically, the total titania is present in an amount not greater than about 35 weight percent, based on the total weight of the catalyst including secondary support. Unless otherwise noted, any binder added to, physically mixed with, extruded with, or incorporated into the titanium-containing support shall be considered to be a component of the titanium-containing support.

The particles of the nanoporous titanium-containing support, excluding any binder, are preferably greater than about 50 nm and less than about 2 microns (μm) in diameter (or largest dimension). More preferably, the particles of the nanoporous titanium-containing support, including binder, are greater than about 50 nm and less than about 1 μm in diameter (or largest dimension).

At the present time, the hydro-oxidation catalyst of this invention is preferably prepared by a process comprising depositing a gold-ligand cluster complex onto the nanoporous titanium-containing support under conditions sufficient to prepare a catalyst precursor, and thereafter heating and/or chemically treating the catalyst precursor under conditions sufficient to form the hydro-oxidation catalyst composition of this invention. In preferred embodiments of this invention, a gold-ligand cluster complex is preferably employed which has a diameter (or largest dimension) greater than the pore size of the titanium-containing nanoporous support. Such a cluster complex essentially cannot access the pores, channels, or cavities of the support; and therefore in these preferred embodiments, the cluster complex binds substantially to the exterior surface of the support. Gold-ligand cluster complexes provide several advantages over prior art gold colloidal suspensions used in preparing hydro-oxidation catalysts. Firstly, gold-ligand cluster complexes tend to be isolable solids of a relatively pure and monodisperse form. Like other stable compounds, the gold-ligand cluster complexes can be handled without strenuous efforts to avoid contact with oxygen and/or water. We recommend, however, certain preferred handling methods hereinbelow.

Typical gold clusters found in the gold-ligand cluster complex contain 2, preferably, greater than about 4, and more preferably, greater than about 5 gold atoms. Typical clusters contain less than about 10,000, preferably, less than about 500 gold atoms. Gold-ligand cluster complexes containing the following number of gold atoms are particularly preferred for the gold-ligand cluster complex that is deposited onto the titanium-containing support: $Au_3$, $Au_4$, $Au_5$, $Au_6$, $Au_7$, $Au_8$, $Au_9$, $Au_{10}$, $Au_{11}$, $Au_{12}$, $Au_{13}$, $Au_{20}$, $Au_{55}$, and $Au_{101}$. At the current time, $Au_{55}$ is more preferred. As the number of gold atoms increases in the cluster, difficulty may be encountered in preparing precisely monodisperse clusters. Thus, some variation is expected in the number of gold atoms. For clusters of 20 or more gold atoms, a variation of +/−10 percent may be expected in the number of gold atoms; for example, $Au_{20}$, $Au_{55}$, and $Au_{101}$ are better defined as $Au_{(20+/-2)}$, $Au_{(55+/-5)}$, and $Au_{(101+/-10)}$.

Optionally, the gold-ligand cluster complex may comprise any number of other metal atoms as may be found in mixed gold-silver or gold-noble metal cluster complexes wherein the noble metal is selected from ruthenium, rhodium, palladium, osmium, iridium, and/or platinum; preferably, gold-silver, gold-palladium, and/or gold-platinum ligand cluster complexes. Although a noble metal may be present, it may contribute to increased hydrogenation of the olefin, for example, increased formation of propane from propylene. Accordingly, when a noble metal, like palladium or platinum, is present, silver is beneficially added to the catalyst (i.e., Au/Ag/noble metal) to reduce hydrogenation. In preferred embodiments of this invention, the gold-ligand cluster complex excludes a noble metal selected from ruthenium, rhodium, palladium, osmium, iridium, platinum, and mixtures thereof.

This invention is not limited to how the atoms in the gold cluster are bonded. Gold atoms may be bonded to each other directly through Au—Au bonds; or alternatively, one gold atom may be bonded to another gold atom through an intermediary atom, such as oxygen or sulfur, as in Au—O—Au; or a gold atom may be bonded to another metal atom, such as silver or noble metal, directly (e.g., Au—Ag or Au—Pd) or through an intermediary atom as noted above.

Non-limiting examples of ligands suitable for the gold-ligand cluster complex include organophosphorus ligands, such as organomonophosphine, organopolyphosphine, organomonophosphite, and organopolyphosphite ligands, as well as thiolates [e.g., $^-S(CH_2)_{11}(CH_3)$], thiols [$HS(CH_2)_{11}(CH_3)$], amines (e.g., primary and secondary amines and aminoalcohols), imines, amides (e.g., palmitoylamido), imides (e.g., maleimido, succinimido, phthalimido), carbon monoxide, and halides (F, Cl, Br, I), and mixtures thereof. A preferred ligand is an organophosphorus ligand, more preferred species of which include triorganophosphines, such as triarylphosphines, trialkylphosphines, alkyldiarylphosphines, and dialkylarylphosphines, more preferably, wherein each alkyl is a $C_{1-20}$ alkyl and wherein each aryl is a $C_{6-20}$ aryl. Non-limiting examples of suitable gold-ligand cluster complexes for use in this invention include:

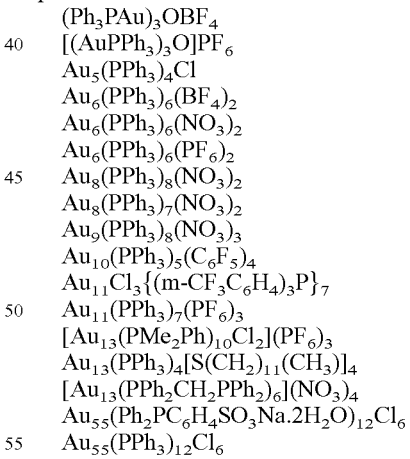

wherein "Ph" is phenyl and "Me" is methyl; as well as gold-ligand cluster compounds and complexes available commercially from companies including Strem Chemicals and Nanoprobes, Incorporated, including the gold-ligand cluster complexes identified as Nanoprobes Catalogue numbers 2010, 2022, 2023. Suitable non-limiting species of mixed gold-noble metal-ligand cluster complexes include:

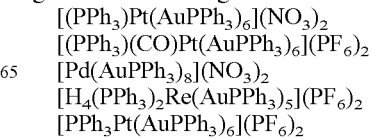

[H(PPh$_3$)Pt(AuPPh$_3$)$_7$](NO$_3$)
[Pt(AuPPh$_3$)$_7$(Ag)$_2$](NO$_3$)$_3$
[Pd(AuPPh$_3$)$_8$](PF$_6$)$_2$
[Pt(AuPPh$_3$)$_8$](NO$_3$)$_2$
[Pt(AuPPh$_3$)$_8$] (PF$_6$)$_2$
[(PPh$_3$)Pt(AuPPh$_3$)$_8$(Ag)](NO$_3$)$_2$
[Pt$_2$(AuPPh$_3$)$_{10}$(Ag)$_{13}$]Cl$_7$
[Pt(AuPPh$_3$)$_8$Ag](NO$_3$)$_3$ wherein "Ph" is phenyl. Mixtures of any of the aforementioned gold-ligand cluster complexes, including gold-only, gold-silver, gold-noble metal, and gold-noble metal-silver ligand cluster complexes, may also be suitably employed. Of course, the phosphine ligands in the aforementioned formulas can be replaced with any other equivalent triorganophosphine ligand, such as tri(tolyl)phosphine or bis(diphenylphosphino) methane. Moreover, any of the anions in the aforementioned preferred formulas can be replaced with an equivalent anion. A more preferred gold-ligand cluster complex is Nanogold® brand gold-ligand cluster complex having an average gold particle size of about 1.4 nm, which can be purchased from Nanoprobes, Incorporated.

Prior to deposition onto the support, the gold-ligand cluster complex can be analyzed, for example, by infrared spectroscopy and/or solution nuclear magnetic resonance (NMR) spectroscopy (e.g., $^1$H, $^{13}$C, or $^{31}$P NMR), for characterization of the ligand(s) and complex. The gold-ligand cluster complexes, including the mixed gold-noble metal-ligand cluster complexes, may be purchased from a commercial source or, alternatively, synthesized from methods described in the art. The following publications provide description of syntheses of gold-ligand cluster complexes and their characterization, all publications being incorporated herein by reference: Nesmeyanov, A. N., et al., *Journal of Organometallic Chemistry* 1980, 201, 343-349; Briant, C. E., et al., *J. Chem. Soc., Chem. Commun.* 1981, 201; Briant, C. E., et al., *Journal of Organometallic Chemistry* 1983, 254, C18-C20; Van der Velden, J. W. A., et al., *Inorganic Chemistry* 1983, 22, 1913-1918.; Schmid, G., et al., *Polyhedron* 1988, 7, 605-608; Ito, L. N., et al., *Inorg. Chem.* 1989, 28, 2026-2028; Ito, L. N., et al., *Inorg. Chem.* 1989, 28, 3696-3701; Schmid, G., *Inorganic Syntheses* 1990, 27, 214-18; Ramamoorthy, V., et. al., *J. Am. Chem. Soc.* 1992, 114, 1526-1527; Laguna, A., et al., *Organometallics* 1992, 11, 2759-2760; Rapoport, D. H., et al., *J. Phys. Chem. B.* 1997, 101, 4175-4183; Warner, M. G., et al., *Chem. Mater.* 2000, 12, 3316-3320; Nunokawa, K., et al. *Bulletin of the Chemical Society of Japan* 2003, 76, 1601-1602; Negishi, Y., et al., *J. Am. Chem. Soc.* 2004, 126, 6518-6519; and Shichibu, Y., et al., *J. Am. Chem. Soc.* 2005, 127, 13464-13465.

There is no limitation on the method of depositing the gold-ligand cluster complex onto the titanium-containing support, so long as the catalyst produced exhibits activity in the hydro-oxidation process of this invention. Non-limiting examples of suitable deposition methods include impregnation, deposition-precipitation, spray-drying, ion-exchange, solid-solid reaction, and freeze-drying. Impregnation is preferred, which involves wetting the support to a point of incipient wetness or to a point of lesser or greater wetness, as desired, with a solution, suspension, or colloid containing the gold-ligand cluster complex. The impregnation conditions may vary with the specific gold-ligand cluster complex, its concentration in the solution or suspension, and the particular support employed. The support may be treated with multiple impregnations, if desired.

Generally, the temperature of the deposition ranges from about sub-ambient (taken as about −100° C.) to about 300° C. Suitable solvents include, but are not limited to, water and organic solvents, the latter including alcohols (e.g., methanol, ethanol, isopropanol, butanol), esters, ketones (e.g., acetone), aliphatic and aromatic hydrocarbons and halocarbons (e.g., methylene chloride), and alkylene glycols, such as, ethylene glycol and diethylene glycol. Mixtures of water and organic solvents are also suitably employed. Typically, where a solution is used, the concentration of the gold-ligand cluster complex ranges from about 0.00001 M to the saturation point thereof, preferably, from about 0.0001 M to about 0.5 M. Optionally, the solution may contain cationic and/or anionic additives including, for example, promoter metal ions (for example, Li$^+$, Na$^+$, K$^+$, Rb$^+$, Cs$^+$, Mg$^{2+}$ Ca$^{2+}$, Sr$^{2+}$, Ba$^{2+}$, La$^{3+}$, and Sm$^{3+}$) as noted hereinafter, as well as anionic species, such as, halides, sulfates, phosphates, carbonates, borates, nitrates, and carboxylates, such as, acetates, lactates, citrates, maleates, cinnamates, and mixtures thereof. Generally, the deposition is conducted under air at ambient pressure. When the deposition is complete, the catalyst precursor composition can be isolated by conventional methods. The deposition solution can be filtered, centrifuged, or decanted to recover the catalyst precursor; or the solvent can be evaporated or distilled off to recover the catalyst precursor. The resulting catalyst precursor composition can be dried at room temperature, if desired, and stored for future use. Storage under air in a freezer is preferred in order to reduce exposure to moisture.

The catalyst precursor composition comprising the gold-ligand cluster complex deposited on particles of the nanoporous titanium-containing support can be characterized by any modern analytical method. Neutron activation analysis (NAA) or X-ray fluorescence (XRF), for example, can be used to identify the chemical composition of the catalyst precursor. STM can be used to visualize clusters with ligands still attached. XPS can be used to determine the oxidation state of the gold. High resolution electron energy loss spectroscopy (HREELS) may also be useful for the determination of gold or other metals at low concentrations.

The catalyst precursor is thereafter heated and/or chemically treated under conditions sufficient to form the catalyst of this invention. Heating in an inert atmosphere is one suitable method. Inert atmospheres include nitrogen, helium, neon, argon, and like noble gases, as well as diluents including methane, carbon dioxide, steam, and alkane hydrocarbons, such as propane. Alternatively, heating with simultaneous chemical treatment, such as calcining under an oxidizing agent or heating under a reducing agent, is also suitable and may be preferred, as described hereinafter. The heating temperature depends upon the particular ligand involved, but may range from greater than about 50° C., preferably, greater than about 100° C. to about 800° C., more preferably, from about 120° C. to about 500° C. For the preferred phosphine ligand cluster complexes, a preferred heating temperature ranges from about 120° C. to about 400° C.

Chemical treatment, with or without heating, is also suitably employed. Chemical treatment involves contacting the catalyst precursor composition with a reactive chemical, for example, a reducing agent or an oxidizing agent. Non-limiting examples of suitable oxidizing agents include essentially pure oxygen, air, ozone, nitrogen oxides, hydrogen peroxide, and mixtures thereof. Optionally, the oxidizing agent may be diluted with an inert gas, those being noted hereinbefore. The preferred oxidizing agent is air or a mixture of oxygen and inert gas(es), such as helium. Non-limiting examples of suitable reducing agents include hydrogen, alkenes (preferably, $C_{1-10}$ alkenes, such as, propylene), sodium borohydride, diborane, formaldehyde, sodium nitrite, oxalic acid, carbon monoxide, hydrogen peroxide, and mixtures thereof. We note that hydrogen peroxide may act as either an oxidizing agent or a reducing agent. A preferred reducing agent is hydrogen, optionally, diluted with an inert gas. If an inert gas diluent is used with the oxidizing or reducing agent, the concentration of oxidizing or reducing agent in the diluent may suitably range from about 1 percent to about 99 percent, by volume. As an optional procedure, the precursor composition can be washed with hydrogen peroxide or reacted in solution or suspension with sodium borohydride. Alternatively, the catalyst precursor can be converted into the catalyst of this invention by heating under hydrogen or oxygen in situ in the hydro-oxidation reactor prior to running the hydro-oxidation process. A more preferred treatment involves heating the catalyst in situ under hydrogen or hydrogen diluted with an inert gas, more preferably, at a temperature between about 200° C. and about 300° C.

The heating and/or chemical treatment is conducted for a time sufficient to form the hydro-oxidation catalyst of this invention. Typically, a period of from about 15 minutes to about 5 hours is sufficient. Depending upon the particular conditions of the heat and/or chemical treatment and the temperature thereof, the gold-ligand bond may or may not be broken. X-ray fluorescence (XRF) may be useful for confirming that the ligand has been removed from the precursor composition during the heating and/or chemical treatment; however, the removal of ligand is not a requirement for obtaining an active hydro-oxidation catalyst of this invention.

Optionally, the catalyst and catalyst precursor compositions of this invention can contain a promoter or a combination of promoters. Any elemental metal, metallic ion, or combination thereof that enhances the performance of the catalyst in the oxidation process of this invention can be employed as a promoter. Factors contributing to increased performance include, but are not limited to, increased conversion of the olefin, increased selectivity to the olefin oxide, decreased productivity to water, increased catalyst lifetime, and decreased molar ratio of water/olefin oxide, preferably, $H_2O$/PO. Typically, the valence of the promoter ion(s) ranges from +1 to +7; but metallic species (zerovalent) may also be present. Non-limiting examples of suitable promoters include the metals of Groups 1 through 12 of the Periodic Table of the Elements, as well as the rare earth lanthanides and actinides, as referenced in the CRC Handbook of Chemistry and Physics, 75$^{th}$ ed., CRC Press, 1994. Preferably, the promoter is selected from silver, Group 1 metals including lithium, sodium, potassium, rubidium, and cesium; Group 2 metals, including beryllium, magnesium, calcium, strontium, and barium; the lanthanide rare earth metals, including lanthanum, cerium, praseodymium, neodymium, promethium, samarium, europium, gadolinium, terbium, dysprosium, holmium, erbium, thulium, ytterbium, and lutetium; and the actinide metals, specifically, thorium and uranium. More preferably, the promoter is selected from silver, magnesium, calcium, strontium, barium, erbium, lutetium, lithium, sodium, potassium, rubidium, cesium, and combinations thereof.

If one or more promoters are used, then the total quantity of promoter(s) generally is greater than about 0.001 and, preferably, greater than about 0.005 weight percent, based on the total weight of the catalyst. The total quantity of promoter(s) is generally less than about 20 and, preferably, less than about 15 weight percent, based on the total weight of the catalyst.

The promoter(s) can be deposited onto the titanium-containing support simultaneously with the gold-ligand cluster complex, or alternatively, in a separate step either before or after the gold-ligand cluster complex is deposited. If the titanium-containing support is to be fabricated during catalyst preparation, then the promoter(s) can be deposited onto a non-Ti support material simultaneously with a source of titanium, or alternatively, in a separate step either before or after the source of titanium is deposited. Typically, the promoter(s) are deposited from an aqueous or organic solution or suspension containing one or more promoter metal salts and, optionally, other additives. Any salt of the promoter can be used; for example, the promoter halides, such as the fluorides, chlorides, and bromides; nitrates, borates, silicates, sulfates, phosphates, hydroxides, carbonates, bicarbonates, and carboxylates, particularly the acetates, oxylates, cinnamates, lactates, maleates, citrates. Mixtures of the aforementioned salts can be used. If an organic solvent is employed, it can be any of a variety of known organic solvents, including, for example, alcohols, esters, ketones, and aliphatic and aromatic hydrocarbons. Ordinarily, the support is contacted with the solution of the promoter salt under conditions that are similar to those used for contacting the support with the solution of the gold-ligand cluster complex. After the promoter(s) are deposited, washing is optional; and if done, the wash liquid preferably contains salts of the desired promoters. Afterwards, heating the promoter-impregnated support in an inert gas or heating and/or chemical treatment with a reducing agent or an oxidizing agent may be conducted in a manner similar to that described hereinbefore for post-deposition treatment of the gold-ligand cluster complex.

The process of this invention can be conducted in a reactor of any conventional design suitable for gas or liquid phase processes. These designs broadly include batch, fixed-bed, transport bed, fluidized bed, moving bed, trickle bed, and shell and tube reactors, as well as continuous and intermittent flow and swing reactor designs. The olefin, hydrogen, and oxygen can be contacted together. Alternatively, the process can be conducted step-wise wherein the catalyst is first contacted with oxygen and thereafter the oxygenated catalyst is contacted with a mixture of propylene and hydrogen. Preferably, the process is conducted in the gas phase, and the reactor is designed with heat transfer features for the removal of the heat produced. Preferred reactors designed for these purposes include fixed-bed, shell and tube, fluidized bed, and moving bed reactors, as well as swing reactors constructed from a plurality of catalyst beds connected in parallel and used in an alternating fashion.

The process conditions for the oxidation described herein can vary considerably over a nonflammable and flammable regime. It is beneficial, however, to recognize the conditions that distinguish between nonflammable and flammable mixtures of the olefin, hydrogen, and oxygen. Accordingly, a composition diagram can be constructed or consulted which for any given process temperature and pressure shows the flammable and non-flammable range of reactant compositions, including the diluent, if used. The more preferred reactant mixtures specified hereinabove are believed to lie outside the flammable regime when the process is operated at the more preferred temperatures and pressures specified hereinbelow. Nevertheless, operation within the flammable regime is possible, as designed by one skilled in the art.

Usually, the process is conducted at a temperature that is greater than about 160° C., preferably, greater than about 180° C. Usually, the process is conducted at a temperature less than about 300° C., preferably less than about 280° C. Usually, the pressure ranges from about atmospheric to about 500 psig (3,448 kPa), preferably, from about 100 psig (690 kPa) to about 300 psig (2,069 kPa).

In flow reactors, the residence time of the reactants and the molar ratio of reactants to catalyst are typically determined by the space velocity. For a gas phase process the gas hourly space velocity (GHSV) of the olefin can vary over a wide range, but typically is greater than about 10 ml olefin per ml catalyst per hour ($h^{-1}$), preferably greater than about 100 $h^{-1}$, and more preferably, greater than about 1,000 $h^{-1}$. Typically, the GHSV of the olefin is less than about 50,000 $h^{-1}$, preferably, less than about 35,000 $h^{-1}$, and more preferably, less than about 20,000 $h^{-1}$. Also, for a gas phase process the total gas hourly space velocity (GHSV) of the feedstream comprising olefin, oxygen, hydrogen, and optional diluent can vary over a wide range, but typically is greater than about 10 ml gas per ml catalyst per hour ($h^1$), preferably, greater than about 100 $h^{-1}$, and more preferably, greater than about 1,000 $h^{-1}$. Typically, the GHSV of the feedstream comprising olefin, oxygen, hydrogen, and optional diluent is less than about 50,000 $h^{-1}$, preferably, less than about 35,000 $h^{-1}$, and more preferably, less than about 20,000 $h^{-1}$ Likewise, for a liquid phase process the weight hourly space velocity (WHSV) of the olefin component can vary over a wide range, but typically is greater than about 0.01 g olefin per g catalyst per hour ($h^{-1}$), preferably, greater than about 0.05 $h^{-1}$, and more preferably, greater than about 0.1 $h^{-1}$. Typically, the WHSV of the olefin is less than about 100 $h^{-1}$, preferably, less than about 50 $h^{-1}$, and more preferably, less than about 20 $h^{-1}$. The gas and weight hourly space velocities of the oxygen, hydrogen, and diluent components can be determined from the space velocity of the olefin taking into account the relative molar ratios desired.

When an olefin having at least three carbon atoms is contacted with oxygen in the presence of hydrogen and the catalyst described hereinabove, the corresponding olefin oxide (epoxide) is produced in high selectivity and good productivity. A preferred olefin oxide is propylene oxide.

The conversion of olefin in the process of this invention can vary depending upon the specific process conditions employed, including the specific olefin, temperature, pressure, mole ratios of reactants, and form of the catalyst. For the purposes of this invention, the term "conversion" is defined as the mole percentage of olefin that reacts to form products. Typically, an olefin conversion of greater than about 1.0 mole percent is achieved. Preferably, the olefin conversion is greater than about 1.5 mole percent, more preferably, greater than about 2.0 mole percent The selectivity to olefin oxide can vary depending upon the specific process conditions employed. For the purposes of this invention, the term "selectivity" is defined as the mole percentage of reacted olefin that forms a particular product, desirably, the olefin oxide. In preferred embodiments wherein the gold-ligand cluster complex excludes a noble metal, the process of this invention produces olefin oxides in unexpectedly high selectivity. Typically the selectivity to olefin oxide is greater than about 80, preferably, greater than about 85, and more preferably, greater than about 90 mole percent.

The productivity of the catalyst, measured as grams of propylene oxide per kilogram catalyst per hour (g PO/kg cat-h) depends upon the specific catalyst used and process conditions, such as, temperature, pressure, and feedrate. The productivity is typically greater than about 200 g PO/kg cat-h, preferably, greater than about 250 g PO/kg cat-h, and more preferably, greater than about 300 g PO/kg cat-h.

The hydrogen efficiency is advantageously higher than prior art processes. Accordingly, the cumulative water/propylene oxide molar ratio in the product stream averaged over the total run time is low. More specifically, the cumulative water/olefin oxide molar ratio is typically greater than about 1:1, but less than about 8:1, and preferably, less than about 6:1.

The catalyst of this invention exhibits evidence of an improved lifetime. The term "lifetime" as used herein, refers to the time measured from the start of the oxidation process to the point at which the catalyst after one or more regenerations has lost sufficient activity so as to render the catalyst unacceptable, particularly, from a commercial point of view. As evidence of its long lifetime, the catalyst remains active for longer intervals with stabilized activity and little deactivation, as compared with prior art hydro-oxidation catalysts. Typically, a run time greater than about 25 days, preferably, greater than about 30 days, can be achieved in a fixed bed reactor. In more preferred embodiments, the catalyst of this invention has been run for up to about 40 days with little deactivation.

When its activity has decreased to an unacceptably low level, in preferred embodiments the catalyst of this invention can be regenerated. Any catalyst regeneration method generally known to those skilled in the art can be used with the catalyst of this invention, provided that the catalyst is reactivated for the hydro-oxidation process described herein. One suitable regeneration method comprises heating the deactivated catalyst at a temperature between about 150° C. and about 500° C. under an atmosphere of a regeneration gas containing oxygen, hydrogen, water, ozone, or a mixture thereof, and optionally an inert gas as identified hereinbefore. A preferred regeneration temperature ranges between about 200° C. and about 400° C. Preferably, the oxygen, hydrogen, or water comprises from about 2 to about 100 mole percent of the regeneration gas. The regeneration time depends upon the regenerant used; but typically can range from greater than about 2 minutes up to about 20 hours.

The invention will be further clarified by a consideration of the following examples, which are intended to be purely exemplary of the use of the invention. Other embodiments of the invention will be apparent to those skilled in the art from a consideration of this specification or practice of the invention as disclosed herein. Unless otherwise noted, all percentages are given on a mole percent basis.

The following analytical methods are employed to identify the catalyst precursor and catalyst compositions.

Elemental Analysis: Au, Ti, Si, and promoter metal concentrations are determined by neutron activation analysis (NAA), and P is determined by X-ray fluorescence (XRF).

TEM Specimen Preparation: Catalyst particles (14/30 U.S. mesh; 1410/595 μm) are crushed and dispersed onto Cu TEM grids with lacey-carbon support mesh purchased from T. Pella (e.g., catalog number 01883).

Instrumentation for Analytical TEM: A field emission gun TEM (JEOL 2010F Serial no. EM138714-25) is used for imaging metal nanoparticles on nanoporous supports in both conventional and dark field TEM modes. The TEM is operated at an accelerating voltage 200 keV.

Conventional TEM images are recorded using a Gatan multi-scan digital camera (Model MSC794). High angle annular dark field (HAADF) images are also captured using the Gatan Digiscan software with an image size of 512×512 or 1024×1024 pixels.

General Method of Synthesizing a Crystalline Titanosilicate Catalyst Support

Nanometer size crystals (~average 500 nm largest dimension) of a titanosilicate support are synthesized using tetraethylorthosilicate (TEOS), titanium n-butoxide, and tetrapropylammonium hydroxide (TPAOH), in an aqueous reaction mixture having the molar composition: 1.0 Si: 0.0067 Ti: 25 $H_2O$: 0.16 TPA. To a 50 L nitrogen purged carboy are added TEOS (20.11 kg). Separately, into a stirred container in a nitrogen-purged box are added TEOS (1.84 kg) and Ti-butoxide (239.5 g). The mixture in the container is then poured into the 50 L carboy containing the TEOS. The carboy is sealed and mixed vigorously by shaking. In a second 50 L carboy, deionized water (41.79 kg) is mixed with TPAOH (8.57 kg). The TPAOH/H$_2$O mixture is sealed and mixed vigorously. The resulting TPAOH/H$_2$O solution is placed in a refrigerator overnight and is kept cold by placing on ice until further use.

The Ti-butoxide/TEOS mixture is added via vacuum loading into a nitrogen purged reactor with a jacket set to a temperature of −5° C. The chilled TPAOH/H$_2$O solution is pumped into the reactor over an approximate 65 minute period while stirring at 150 rpm. After transfer is complete, the reactor is heated to 60-65° C. (over a period of about 20 minutes). This temperature is maintained for 4.5 hours. The temperature is increased to 160° C. at maximum heating rate (about 50 minutes) and maintained for 96 hours. The reactor is then cooled to 20° C. for recovery of titanosilicate crystals.

The titanosilicate crystals are recovered by flocculation. Using a 1.0 M HNO$_3$ solution, the product of the aforementioned synthesis solution is adjusted to a pH of 8.0 +/−0.2 by slow addition of the acid with vigorous agitation and simultaneous monitoring of the pH. Following pH adjustment, the slurry is centrifuged at about 300-600 rpm. The pH-adjusted slurry is filtered through a polyethylene centrifuge cloth filter bag to recover the crystals. The mother liquor is recycled and passed through the centrifuge bags multiple times until about 96 percent of the total solids are recovered. Fresh deionized water is then passed through the solid cake to rinse excess TPAOH and non-reacted precursor. The wet solid cake is dispersed in fresh deionized water. Once the crystals are dispersed, the suspension is agitated continuously at room temperature. The final solid is recovered by centrifuging as described above, followed by removing the wet solids and drying in an air atmosphere at 80° C. The resulting solids are crushed and sieved to isolate a 14/30 U.S. mesh fraction (1410/595 μm). The material is calcined in air in a muffle furnace as follows: ramp from room temperature to 550° C. at 2.5° C./minute, followed by holding at 550° C. for 10 hours, followed by self-cool to room temperature. This procedure is carried out in a static mode, i.e., no air flow is intentionally introduced to the furnace. The product comprises a nanoporous titanosilicate material of MFI structure, as determined by XRD. The titanosilicate product exhibits a bulk Si:Ti ratio of 150:1, as determined by NAA.

EXAMPLE 1

A sample of the nanoporous titanosilicate support prepared as described hereinabove is oven dried at 110° C. for 1 hour. An aqueous sodium acetate (NaOAc) solution is prepared by mixing water (75 g) and NaOAc (0.737 g). The NaOAc solution (70.01 g) is added drop-wise into a flask containing the titanosilicate support (100.00 g), with shaking during the addition. The flask is transferred to a vacuum oven and is placed under vacuum at room temperature for 30 minutes, followed by two cycles of shaking and applying vacuum at room temperature for 30 minutes. The sample is then heated under vacuum to 70° C. (±5° C., 25 minute ramp time) and held for 1 hour. The heat is turned off, the sample is cooled to room temperature, and is maintained under vacuum overnight. The vacuum oven is purged with nitrogen and the sample is removed. The material is re-sized to 14/30 U.S. mesh (1410/595 μm) and is bottled.

A portion of the NaOAc-impregnated titanosilicate support is oven dried at 110° C. for 1 hour. A gold-ligand cluster solution is prepared by mixing Au$_9$(PPh$_3$)$_8$(NO$_3$)$_3$ (0.0040 g) with acetone (2.873 g) and methanol (0.900 g). The gold-ligand cluster solution (0.738 g) is added to the NaOAc-impregnated titanosilicate support (1.10 g). The sample is covered and allowed to sit for 50 minutes, then transferred to a vacuum oven followed by heating under vacuum at 100° C. for 30 minutes. The sample is then cooled to room temperature and maintained under vacuum overnight to yield a catalyst precursor composition. Elemental Analysis: Au, 267 +/−5 ppm; Na, 1690 +/−90 ppm; Ti, 4770 +/−90 ppm; Si, 43 +/−1 percent; P, 31 +/−5 ppm.

The catalyst precursor composition is treated to form a catalyst of this invention, which is tested in the hydro-oxidation of propylene to propylene oxide as follows. The catalyst precursor composition (0.5 g) is loaded into a fixed-bed, continuous flow reactor and conditioned as follows to form a catalyst of this invention. A flow of 10 percent hydrogen (by volume) in helium is started. The reactor is heated from room temperature to 250° C. at a rate of 120° C./hour, held at 250° C. for 1 hour, and then cooled to 100° C. The reactor is then fed with helium, heated to 160° C., and held for 1 hour. Thereafter, the temperature is reduced to 140° C., and then a feed of propylene, oxygen, and hydrogen is introduced (30 percent propylene, 10 percent oxygen, 10 percent hydrogen, balance helium, 250 cc/min space velocity, 100 psig (690 kPa)). Catalyst evaluation is conducted while holding the temperature at 140° C. for 8 hours, increasing to 160° C. over a period of 8 hours, and then further increasing to temperatures up to about 240° C. Products are analyzed with an on-line gas chromatograph. Results are shown in Table 1 and graphed in FIGS. 1 and 2. Measurements of propylene conversion, propylene oxide selectivity, and cumulative water to propylene oxide molar ratio are taken approximately every hour over the entire run time. The measurements illustrated in the table and figure are the values recorded approximately every 12 and 24 hours (or twice daily) from start of the run.

TABLE 1

Hydro-Oxidation of Propylene With Au/Na/TS Catalyst[1,2]

| Time (days) | Temperature (° C.) | PP Conversion | PO Selectivity | Productivity (g PO/kg cat-h) | Cumulative H$_2$O/PO |
|---|---|---|---|---|---|
| 0.5 | 140 | 0.18 | 99.4 | 42 | 4.80 |
| 1.0 | 220 | 1.15 | 91.6 | 246 | 4.08 |
| 1.5 | 237 | 1.55 | 89.7 | 326 | 4.29 |
| 2.0 | 237 | 1.55 | 89.8 | 326 | 4.34 |
| 2.5 | 237 | 1.55 | 90.4 | 327 | 4.35 |
| 3.0 | 237 | 1.54 | 90.1 | 325 | 4.35 |
| 3.5 | 237 | 1.53 | 89.9 | 320 | 4.36 |
| 4.0 | 237 | 1.51 | 90.0 | 318 | 4.36 |
| 4.5 | 237 | 1.50 | 90.3 | 316 | 4.36 |
| 5.0 | 237 | 1.49 | 90.0 | 314 | 4.37 |
| 5.5 | 237 | 1.47 | 90.1 | 309 | 4.38 |
| 6.0 | 237 | 1.45 | 90.1 | 306 | 4.39 |
| 6.5 | 237 | 1.44 | 90.1 | 303 | 4.40 |
| 7.0 | 237 | 1.43 | 89.7 | 298 | 4.41 |
| 7.5 | 237 | 1.40 | 90.1 | 295 | 4.42 |
| 8.0 | 237 | 1.41 | 89.8 | 295 | 4.43 |
| 8.5 | 237 | 1.38 | 89.8 | 290 | 4.45 |
| 9.0 | 237 | 1.38 | 89.5 | 289 | 4.46 |
| 9.5 | 237 | 1.38 | 89.7 | 289 | 4.47 |
| 10.0 | 237 | 1.38 | 89.6 | 288 | 4.48 |
| 10.5 | 237 | 1.36 | 89.7 | 285 | 4.49 |
| 11.0 | 237 | 1.35 | 89.5 | 283 | 4.51 |
| 11.5 | 237 | 1.34 | 89.5 | 281 | 4.52 |
| 12.0 | 237 | 1.33 | 89.3 | 278 | 4.53 |
| 12.5 | 237 | 1.32 | 89.5 | 275 | 4.55 |
| 13.0 | 237 | 1.32 | 89.3 | 275 | 4.56 |
| 13.5 | 237 | 1.30 | 89.4 | 272 | 4.58 |
| 14.0 | 237 | 1.30 | 89.5 | 271 | 4.59 |
| 14.5 | 237 | 1.29 | 89.1 | 268 | 4.61 |
| 15.0 | 237 | 1.29 | 89.3 | 268 | 4.62 |
| 15.5 | 237 | 1.28 | 89.2 | 266 | 4.64 |
| 16.0 | 237 | 1.28 | 89.2 | 267 | 4.65 |
| 16.5 | 237 | 1.26 | 89.2 | 263 | 4.66 |

TABLE 1-continued

Hydro-Oxidation of Propylene With Au/Na/TS Catalyst[1,2]

| Time (days) | Temperature (°C.) | PP Conversion | PO Selectivity | Productivity (g PO/kg cat-h) | Cumulative $H_2O/PO$ |
|---|---|---|---|---|---|
| 17.0 | 237 | 1.27 | 88.9 | 263 | 4.68 |
| 17.5 | 237 | 1.26 | 89.2 | 262 | 4.69 |
| 18.0 | 237 | 1.25 | 89.2 | 260 | 4.71 |
| 18.5 | 237 | 1.25 | 89.0 | 259 | 4.72 |
| 19.0 | 237 | 1.24 | 89.2 | 258 | 4.73 |
| 19.5 | 237 | 1.24 | 89.0 | 258 | 4.75 |
| 20.0 | 237 | 1.24 | 88.9 | 258 | 4.76 |
| 20.5 | 237 | 1.23 | 89.0 | 255 | 4.78 |
| 21.0 | 237 | 1.22 | 88.9 | 254 | 4.79 |
| 21.5 | 237 | 1.21 | 89.0 | 252 | 4.80 |
| 22.0 | 237 | 1.21 | 88.8 | 252 | 4.81 |
| 22.5 | 237 | 1.21 | 89.0 | 251 | 4.83 |
| 23.0 | 237 | 1.21 | 88.6 | 250 | 4.84 |
| 23.5 | 237 | 1.20 | 88.8 | 249 | 4.85 |
| 24.0 | 237 | 1.20 | 88.7 | 249 | 4.86 |
| 24.5 | 237 | 1.19 | 88.6 | 247 | 4.88 |
| 25.0 | 237 | 1.18 | 88.8 | 245 | 4.89 |
| 25.5 | 237 | 1.18 | 88.7 | 244 | 4.90 |
| 26.0 | 237 | 1.17 | 88.8 | 243 | 4.91 |
| 26.5 | 237 | 1.17 | 88.7 | 243 | 4.92 |
| 27.0 | 237 | 1.16 | 88.7 | 240 | 4.93 |
| 27.5 | 237 | 1.16 | 88.5 | 240 | 4.94 |
| 28.0 | 237 | 1.16 | 88.4 | 240 | 4.96 |
| 28.5 | 237 | 1.16 | 88.3 | 240 | 4.97 |
| 29.0 | 237 | 1.16 | 88.6 | 240 | 4.97 |
| 29.5 | 237 | 1.15 | 88.5 | 237 | 4.98 |
| 30.0 | 237 | 1.14 | 88.6 | 236 | 4.99 |
| 30.5 | 237 | 1.14 | 88.6 | 235 | 4.99 |
| 31.0 | 237 | 1.14 | 88.4 | 235 | 5.00 |
| 31.5 | 237 | 1.14 | 88.5 | 235 | 5.01 |
| 32.0 | 237 | 1.13 | 88.5 | 233 | 5.02 |
| 32.5 | 237 | 1.12 | 88.6 | 232 | 5.03 |
| 33.0 | 237 | 1.12 | 88.4 | 231 | 5.04 |
| 33.5 | 237 | 1.11 | 88.5 | 229 | 5.05 |
| 34.0 | 237 | 1.11 | 88.5 | 230 | 5.06 |
| 34.5 | 237 | 1.11 | 88.3 | 230 | 5.07 |
| 35.0 | 237 | 1.11 | 88.3 | 229 | 5.08 |
| 35.5 | 237 | 1.11 | 88.3 | 228 | 5.09 |
| 36.0 | 237 | 1.10 | 88.1 | 226 | 5.10 |
| 36.5 | 237 | 1.09 | 88.4 | 225 | 5.10 |
| 37.0 | 237 | 1.09 | 88.3 | 224 | 5.11 |
| 37.5 | 237 | 1.09 | 88.1 | 224 | 5.12 |
| 38.0 | 237 | 1.08 | 88.1 | 222 | 5.13 |
| 38.5 | 237 | 1.08 | 87.8 | 222 | 5.14 |
| 39.0 | 237 | 1.08 | 88.1 | 221 | 5.15 |
| 39.5 | 237 | 1.07 | 88.2 | 220 | 5.16 |
| 40.0 | 237 | 1.07 | 88.1 | 220 | 5.16 |
| 40.5 | 237 | 1.07 | 88.0 | 219 | 5.17 |
| 41.0 | 237 | 1.06 | 87.8 | 217 | 5.18 |
| 41.5 | 237 | 1.06 | 87.8 | 217 | 5.19 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

An elemental analysis of the used catalyst reveals the following composition: Au, 230 +/−5 ppm; Na, 1670 +/−90 ppm; Ti, 4670 +/−90 ppm; Si, 42 +/−1 percent; P, 5 +/−2 ppm.

The results show a virtually flat propylene oxide selectivity of about 89 mole percent at an operating temperature over 230° C. and over a run time of about 41 days. The cumulative $H_2O/PO$ molar ratio slowly rises from only 4.3 to about 5.2 during the same 41 day period. Conversion shows an initial increase and peak, and then a steady but slow decline.

EXAMPLE 2

A portion of the titanosilicate support, prepared as described hereinabove, is oven dried at 110° C. for 1 hour. An aqueous cesium acetate (CsOAc) solution is prepared by mixing water (4.979 g) and CsOAc (0.052 g). The CsOAc solution (1.54 g) is added drop-wise to the titanosilicate support (2.20 g). The sample is transferred to a vacuum oven and is heated under vacuum to 70° C. and held for 1 hour. The heat is turned off; the sample is allowed to cool to room temperature and maintained under vacuum overnight. The vacuum oven is then purged with nitrogen and the sample is removed and bottled.

A portion of the CsOAc-impregnated titanosilicate support is oven dried at 110° C. for 1 hour. A gold-ligand cluster solution is prepared by mixing $Au_9(PPh_3)_8(NO_3)_3$ (0.0040 g) with acetone (2.873 g) and methanol (0.900 g). The resulting gold-ligand cluster solution (0.742 g) is added to the CsOAc/titanosilicate support (1.10 g). The sample is covered and held for 50 minutes. Then, the sample is transferred to a vacuum oven followed by heating under vacuum at 100° C. for 30 minutes. The sample is then cooled to room temperature and maintained under vacuum overnight to yield a catalyst precursor composition. Elemental analysis: Au, 233 +/−5 ppm; Cs, 4340 +/−90 ppm; Ti, 4720 +/−90 ppm; Si, 41 +/−1 percent; and P, 24 +/−3 ppm. The catalyst precursor composition is then conditioned in a propylene hydro-oxidation reactor to obtain a catalyst composition of this invention, which is tested in the hydro-oxidation of propylene; both the conditioning and the hydro-oxidation being conducted in the manner described in Example 1. Results are presented in Table 2 and graphed in FIGS. 3 and 4.

TABLE 2

Hydro-oxidation of Propylene with a Au/Cs/TS Catalyst[1,2]

| Time (days) | Temperature (°C.) | PP Conversion | PO Selectivity | Cumulative $H_2O/PO$ |
|---|---|---|---|---|
| 0.5 | 140 | 0.12 | 100.0 | 5.13 |
| 1.0 | 220 | 1.28 | 93.3 | 4.49 |
| 1.5 | 228 | 1.53 | 93.2 | 4.07 |
| 2.0 | 228 | 1.53 | 93.3 | 3.92 |
| 2.5 | 228 | 1.52 | 93.0 | 3.86 |
| 3.0 | 228 | 1.50 | 93.2 | 3.82 |
| 3.5 | 228 | 1.50 | 93.1 | 3.79 |
| 4.0 | 228 | 1.49 | 93.1 | 3.78 |
| 4.5 | 228 | 1.48 | 93.1 | 3.77 |
| 5.0 | 229 | 1.49 | 92.9 | 3.77 |
| 5.5 | 228 | 1.47 | 93.1 | 3.77 |
| 6.0 | 228 | 1.48 | 93.0 | 3.78 |
| 6.5 | 228 | 1.46 | 92.9 | 3.78 |
| 7.0 | 228 | 1.46 | 93.0 | 3.78 |
| 7.5 | 228 | 1.44 | 93.0 | 3.79 |
| 8.0 | 228 | 1.44 | 92.9 | 3.80 |
| 8.5 | 228 | 1.43 | 92.9 | 3.81 |
| 9.0 | 228 | 1.41 | 92.9 | 3.81 |
| 9.5 | 228 | 1.47 | 92.7 | 3.82 |
| 10.0 | 228 | 1.48 | 92.4 | 3.83 |
| 10.5 | 228 | 1.48 | 92.4 | 3.84 |
| 11.0 | 228 | 1.41 | 92.6 | 3.85 |
| 11.5 | 228 | 1.42 | 92.6 | 3.86 |
| 12.0 | 228 | 1.41 | 92.7 | 3.87 |
| 12.5 | 228 | 1.41 | 92.6 | 3.88 |
| 13.0 | 228 | 1.41 | 92.4 | 3.90 |
| 13.5 | 228 | 1.40 | 92.7 | 3.91 |
| 14.0 | 228 | 1.40 | 92.5 | 3.92 |
| 14.5 | 228 | 1.39 | 92.6 | 3.93 |
| 15.0 | 228 | 1.39 | 92.4 | 3.94 |
| 15.5 | 228 | 1.40 | 92.4 | 3.95 |
| 16.0 | 228 | 1.38 | 92.3 | 3.96 |
| 16.5 | 228 | 1.38 | 92.5 | 3.97 |
| 17.0 | 228 | 1.37 | 92.4 | 3.98 |
| 17.5 | 228 | 1.37 | 92.3 | 4.00 |
| 18.0 | 228 | 1.36 | 92.2 | 4.01 |
| 18.5 | 227 | 1.36 | 92.2 | 4.02 |
| 19.0 | 228 | 1.36 | 92.4 | 4.03 |
| 19.5 | 228 | 1.35 | 92.3 | 4.04 |
| 20.0 | 228 | 1.35 | 92.2 | 4.05 |
| 20.5 | 228 | 1.35 | 92.2 | 4.06 |
| 21.0 | 228 | 1.34 | 92.1 | 4.07 |

TABLE 2-continued

Hydro-oxidation of Propylene with a Au/Cs/TS Catalyst[1,2]

| Time (days) | Temperature (° C.) | PP Conversion | PO Selectivity | Cumulative H$_2$O/PO |
|---|---|---|---|---|
| 21.5 | 228 | 1.35 | 92.1 | 4.08 |
| 22.0 | 228 | 1.34 | 92.0 | 4.09 |
| 22.5 | 229 | 1.33 | 92.0 | 4.10 |
| 23.0 | 227 | 1.31 | 92.0 | 4.11 |
| 23.5 | 227 | 1.32 | 92.0 | 4.12 |
| 24.0 | 228 | 1.31 | 92.0 | 4.12 |
| 24.5 | 228 | 1.32 | 92.0 | 4.13 |
| 25.0 | 228 | 1.31 | 92.1 | 4.14 |
| 25.5 | 228 | 1.32 | 91.8 | 4.15 |
| 26.0 | 228 | 1.30 | 92.1 | 4.16 |
| 26.5 | 228 | 1.31 | 91.8 | 4.17 |
| 27.0 | 229 | 1.30 | 91.8 | 4.18 |
| 27.5 | 228 | 1.31 | 92.0 | 4.19 |
| 28.0 | 228 | 1.29 | 91.7 | 4.19 |
| 28.5 | 228 | 1.29 | 92.0 | 4.20 |
| 29.0 | 229 | 1.28 | 91.9 | 4.20 |
| 29.5 | 228 | 1.29 | 92.0 | 4.21 |
| 30.0 | 228 | 1.27 | 92.0 | 4.22 |
| 30.5 | 228 | 1.27 | 92.0 | 4.22 |
| 31.0 | 228 | 1.28 | 91.9 | 4.23 |
| 31.5 | 228 | 1.27 | 92.1 | 4.24 |
| 32.0 | 228 | 1.25 | 92.2 | 4.25 |
| 32.5 | 228 | 1.28 | 91.9 | 4.25 |
| 33.0 | 228 | 1.27 | 91.9 | 4.26 |
| 33.5 | 229 | 1.26 | 91.9 | 4.27 |
| 34.0 | 228 | 1.26 | 92.0 | 4.27 |
| 34.5 | 228 | 1.26 | 91.7 | 4.28 |
| 35.0 | 228 | 1.26 | 91.8 | 4.29 |
| 35.5 | 229 | 1.26 | 91.6 | 4.29 |
| 36.0 | 227 | 1.24 | 91.6 | 4.30 |
| 36.5 | 228 | 1.23 | 91.5 | 4.31 |
| 37.0 | 228 | 1.22 | 91.9 | 4.31 |
| 37.5 | 228 | 1.23 | 92.2 | 4.32 |
| 38.0 | 228 | 1.23 | 91.4 | 4.33 |
| 38.5 | 228 | 1.22 | 91.6 | 4.33 |
| 39.0 | 228 | 1.22 | 91.7 | 4.34 |
| 39.5 | 228 | 1.24 | 91.6 | 4.34 |
| 40.0 | 229 | 1.22 | 91.6 | 4.35 |
| 40.5 | 229 | 1.22 | 91.5 | 4.35 |
| 41.0 | 228 | 1.22 | 91.7 | 4.36 |
| 41.5 | 228 | 1.23 | 91.6 | 4.36 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

An elemental analysis of the used catalyst reveals the following composition: Au, 230 +/−5 ppm; Cs, 4220 +/−90 ppm; Ti, 4790 +/−90 ppm; Si, 41 +/−1 percent; P, not detectable. TEM of the used catalyst shows gold nanoparticles of a median size 4.4 nm.

The results show a virtually flat propylene oxide selectivity of about 91 mole percent at an operating temperature over 220° C. and over a run time of about 41 days. The cumulative H$_2$O/PO molar ratio rises only slightly from 3.8 to about 4.4 during the same 41 day period. Conversion shows an initial increase and peak, and then a steady but slow decline.

EXAMPLE 3

A portion of a CsOAc-impregnated titanosilicate support prepared as described in Example 2 is oven dried at 110° C. for 1 hour. A gold cluster solution is prepared by shaking Nanogold® brand Au-ligand cluster complex (30 nmol; 1.4 nm gold particles, Nanoprobes, Incorporated, Catalog no. 2010) with cold methanol (0.81 g). The solution is put into a freezer for 5 minutes, and then the entire volume of solution is added to the CsOAc/titanosilicate support (1.2 g). The sample is covered and held in a freezer for 1 hour. The sample is transferred to a vacuum oven, held at room temperature for 1 hour, heated to 105° C. over a period of about 30 minutes, held at 105° C. for 60 minutes, cooled to room temperature, and then maintained under vacuum overnight to yield a catalyst precursor composition of this invention. Elemental analysis: Au, 286 +/−5 ppm; Cs, 4380 +/−90 ppm; Ti, 4870 +/−90 ppm; Si, 42 +/−1 percent; and P, 15 +/−3 ppm. The catalyst precursor composition is then conditioned in the reactor to form a catalyst composition of this invention, which is tested in the hydro-oxidation of propylene; both the conditioning and the hydro-oxidation being conducted in the manner described in Example 1. Results are shown in Table 3 and FIGS. 5 and 6.

TABLE 3

Hydro-oxidation of Propylene Using Au/Cs/Ti Catalyst[1,2]

| Time (days) | Temperature (° C.) | PP Conversion | PO Selectivity | Cumulative H$_2$O/PO |
|---|---|---|---|---|
| 0.5 | 140 | 0.43 | 99.7 | 2.10 |
| 1.0 | 176 | 1.04 | 98.3 | 2.31 |
| 1.5 | 188 | 1.50 | 97.8 | 2.60 |
| 2.0 | 188 | 1.49 | 97.4 | 2.73 |
| 2.5 | 188 | 1.47 | 97.6 | 2.82 |
| 3.0 | 190 | 1.51 | 97.1 | 2.89 |
| 3.5 | 190 | 1.46 | 97.8 | 2.95 |
| 4.0 | 198 | 1.74 | 97.5 | 3.00 |
| 4.5 | 205 | 1.97 | 96.8 | 3.06 |
| 5.0 | 208 | 2.05 | 96.7 | 3.11 |
| 5.5 | 208 | 1.99 | 96.5 | 3.15 |
| 6.0 | 210 | 2.05 | 96.3 | 3.20 |
| 6.5 | 210 | 2.00 | 96.4 | 3.24 |
| 7.0 | 210 | 1.95 | 96.6 | 3.27 |
| 7.5 | 212 | 2.02 | 96.2 | 3.30 |
| 8.0 | 212 | 2.00 | 96.3 | 3.34 |
| 8.5 | 212 | 1.95 | 96.2 | 3.37 |
| 9.0 | 214 | 2.03 | 95.9 | 3.40 |
| 9.5 | 214 | 2.01 | 96.0 | 3.42 |
| 10.0 | 214 | 1.98 | 95.8 | 3.45 |
| 10.5 | 214 | 1.97 | 96.1 | 3.47 |
| 11.0 | 212 | 1.95 | 96.1 | 3.49 |
| 11.5 | 217 | 2.07 | 95.8 | 3.51 |
| 12.0 | 217 | 2.04 | 95.8 | 3.53 |
| 12.5 | 217 | 2.02 | 95.8 | 3.56 |
| 13.0 | 217 | 2.01 | 95.8 | 3.58 |
| 13.5 | 217 | 2.00 | 95.7 | 3.60 |
| 14.0 | 217 | 1.98 | 95.7 | 3.62 |
| 14.5 | 217 | 1.97 | 95.6 | 3.64 |
| 15.0 | 218 | 1.99 | 95.7 | 3.66 |
| 15.5 | 219 | 2.04 | 95.5 | 3.68 |
| 16.0 | 219 | 2.02 | 95.4 | 3.69 |
| 16.5 | 219 | 2.03 | 95.4 | 3.71 |
| 17.0 | 219 | 2.00 | 95.3 | 3.73 |
| 17.5 | 219 | 1.97 | 95.4 | 3.75 |
| 18.0 | 220 | 1.97 | 95.4 | 3.76 |
| 18.5 | 222 | 2.09 | 95.0 | 3.78 |
| 19.0 | 222 | 2.05 | 95.1 | 3.80 |
| 19.5 | 222 | 2.05 | 94.9 | 3.82 |
| 20.0 | 222 | 2.05 | 94.9 | 3.84 |
| 20.5 | 222 | 2.01 | 95.0 | 3.85 |
| 21.0 | 222 | 2.00 | 94.8 | 3.87 |
| 21.5 | 222 | 1.97 | 95.2 | 3.89 |
| 22.0 | 222 | 1.98 | 94.9 | 3.91 |
| 22.5 | 225 | 2.09 | 94.6 | 3.93 |
| 23.0 | 225 | 2.07 | 94.6 | 3.94 |
| 23.5 | 225 | 2.06 | 94.7 | 3.96 |
| 24.0 | 225 | 2.06 | 94.5 | 3.98 |
| 24.5 | 225 | 2.04 | 94.5 | 4.00 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

An elemental analysis of the used catalyst reveals the following composition: Au, 278 +/−5 ppm; Cs, 4250 +/−90 ppm; Ti, 4450 +/−90 ppm; Si, 40 +/−1 percent; P, 12 +/−3 ppm. TEM of the used catalyst shows gold nanoparticles of a median size 2.3 nm.

The results show a high propylene oxide selectivity of greater than or close to 95 mole percent at an operating temperature over 200° C. throughout a run time of about 25 days. After approximately an initial four days, the conversion is maintained at approximately 2 percent by adjustments in the reaction temperature. The cumulative water/PO molar ratio remains at less than 4 over a period of more than 20 days.

EXAMPLE 4

A gold-noble metal-ligand cluster complex $(PPh_3)Pt(AuPPh_3)_6(NO_3)_2$ is prepared via a published literature method as described in Mueting, A. M., et al., *Inorganic Syntheses* (1992), 29, 279-98. The cluster complex (5.0 mg) is dissolved in methylene dichloride (10 g) in a glass vial, into which a crystalline titanosilicate (1.00 g) containing sodium acetate (1.35 wt percent) is added. The crystalline titanosilicate is similar to the titanosilicate used in Example 1 hereinabove. The solid is manually swirled in the solution, during which time the cluster compound is adsorbed onto the titanosilicate. The excess methylene chloride solution is decanted off the solid, and a catalyst precursor composition is isolated onto a drying dish. The precursor composition is dried under air for 4 hrs followed by drying in a vacuum oven at 70° C. for 1 hour. The solid (0.50 g) is loaded into a tubular reactor (316 SS; 0.25 inch outer diameter) and dried under flowing He at 160° C. for 1 hr to form a catalyst of this invention. After cooling to 140° C. the catalyst is evaluated in the hydro-oxidation of propylene in a manner similar to Example 1 hereinabove, with the exception that the pressure is 94 psig (648 kPa) rather than 100 psig (690 kPa). Results are shown in Table 4 and FIG. 7.

TABLE 4

Hydro-oxidation of Propylene Using Pt/Au Cluster Complex[1,2]

| Time (hours) | Temperature (° C.) | PP Conversion | PO Selectivity | Productivity (g PO/kg cat-h) | Cumulative $H_2O$/PO |
|---|---|---|---|---|---|
| 0.0 | 152 | 28.00 | 0.00 | 0 | 0.00 |
| 1.3 | 151 | 18.18 | 0.00 | 0 | 0.00 |
| 2.7 | 74 | 19.23 | 0.00 | 0 | 0.00 |
| 4.0 | 111 | 0.00 | 0.00 | 0 | 0.00 |
| 5.4 | 122 | 0.36 | 0.00 | 0 | 0.00 |
| 6.7 | 122 | 0.36 | 0.00 | 0 | 0.00 |
| 8.1 | 121 | 0.48 | 0.00 | 0 | 0.00 |
| 9.4 | 121 | 5.45 | 2.38 | 30 | 4.75 |
| 10.7 | 121 | 8.22 | 3.97 | 76 | 5.93 |
| 12.1 | 121 | 8.78 | 4.28 | 88 | 6.29 |
| 13.4 | 121 | 9.01 | 4.49 | 95 | 6.49 |
| 14.8 | 121 | 8.99 | 4.40 | 92 | 6.65 |
| 16.1 | 120 | 9.05 | 4.19 | 89 | 6.83 |
| 17.5 | 122 | 9.08 | 4.31 | 91 | 6.93 |
| 18.8 | 125 | 9.25 | 4.65 | 101 | 7.01 |
| 20.2 | 129 | 9.37 | 5.13 | 112 | 7.06 |
| 21.5 | 132 | 9.43 | 5.60 | 123 | 7.12 |
| 22.8 | 135 | 9.44 | 6.30 | 139 | 7.12 |
| 24.2 | 139 | 9.40 | 6.98 | 153 | 7.18 |
| 25.5 | 142 | 9.38 | 7.59 | 166 | 7.21 |
| 26.9 | 146 | 9.44 | 8.15 | 180 | 7.20 |
| 28.2 | 149 | 9.30 | 8.98 | 195 | 7.19 |
| 29.6 | 152 | 9.50 | 9.37 | 208 | 7.18 |
| 30.9 | 156 | 9.29 | 10.16 | 220 | 7.16 |
| 32.2 | 159 | 9.25 | 10.76 | 232 | 7.14 |
| 33.6 | 160 | 9.27 | 10.64 | 231 | 7.12 |
| 34.9 | 160 | 9.42 | 10.09 | 222 | 7.11 |
| 36.3 | 160 | 9.38 | 9.80 | 215 | 7.09 |
| 37.6 | 160 | 9.39 | 9.52 | 209 | 7.07 |
| 39.0 | 160 | 9.46 | 9.33 | 206 | 7.06 |
| 40.3 | 160 | 9.46 | 9.15 | 202 | 7.04 |
| 41.6 | 160 | 9.50 | 8.99 | 200 | 7.03 |
| 43.0 | 160 | 9.60 | 8.66 | 194 | 7.03 |
| 44.3 | 160 | 9.49 | 8.71 | 193 | 7.02 |
| 45.7 | 160 | 9.58 | 8.58 | 192 | 7.01 |
| 47.0 | 160 | 9.56 | 8.46 | 189 | 7.01 |
| 48.4 | 160 | 9.57 | 8.38 | 187 | 7.01 |
| 49.7 | 160 | 9.63 | 8.29 | 187 | 7.00 |
| 51.0 | 160 | 9.61 | 8.22 | 185 | 7.00 |
| 52.4 | 160 | 9.73 | 7.99 | 182 | 7.00 |
| 53.7 | 160 | 9.72 | 8.07 | 183 | 7.00 |
| 55.1 | 160 | 9.61 | 7.98 | 179 | 7.00 |
| 56.4 | 160 | 9.62 | 7.95 | 179 | 6.99 |
| 57.8 | 160 | 9.59 | 7.92 | 177 | 7.00 |
| 59.1 | 160 | 9.63 | 7.84 | 176 | 7.00 |
| 60.5 | 160 | 9.69 | 7.73 | 175 | 7.00 |
| 61.8 | 160 | 9.61 | 7.76 | 174 | 7.00 |
| 63.1 | 160 | 9.59 | 7.76 | 174 | 7.00 |
| 64.5 | 160 | 9.70 | 7.67 | 174 | 7.00 |
| 65.8 | 160 | 9.61 | 7.74 | 174 | 7.00 |
| 67.2 | 160 | 9.62 | 7.70 | 173 | 7.00 |
| 68.5 | 160 | 9.58 | 7.73 | 173 | 7.00 |
| 69.9 | 160 | 9.59 | 7.76 | 174 | 7.00 |

[1]PP = propylene; PO = propylene oxide
[2]Feed: 30 percent propylene, 10 percent oxygen, 10 percent hydrogen, balance helium, 250 cc/min space velocity, 94 psig (648 kPa).

The data show that a catalyst prepared from a mixed Au—Pt-phosphine ligand cluster complex produces, after start-up, a propylene conversion of between 9 and about 10 percent through a run time of up to 69.9 hours. Selectivity to propylene oxide varies and does not exceed 10 percent; propane is the primary product. Significantly, after start-up, the cumulative $H_2O$/PO molar ratio remains steady between 6 and 7 through the run time of 69.9 hours.

EXAMPLE 5

A portion of a CsOAc-impregnated titanosilicate support prepared as described in Example 2 is oven dried at 136° C. for 1 hour. A gold cluster solution is prepared by mixing Positively Charged Nanogold® Au-ligand cluster complex (30 nmol; 1.4 nm gold particles containing several primary amine groups per molecule; Nanoprobes, Incorporated; Catalog no. 2022) with cold methanol (1.403 g). The solution (0.77 g) is then added to the CsOAc/titanosilicate support (1.10 g). The sample is covered and held at room temperature for 30 minutes. The sample is transferred to a vacuum oven, heated to 100° C., held at 100° C. for 60 minutes, cooled to room temperature, and then maintained under vacuum overnight to yield a catalyst precursor composition of this invention. The catalyst precursor composition is then conditioned in the reactor to form a catalyst composition of this invention, which is tested in the hydro-oxidation of propylene; both the conditioning and the hydro-oxidation being conducted in the manner described in Example 1. Results are shown in Table 5 and FIGS. 8 and 9.

TABLE 5

Hydro-oxidation of Propylene Using Au Cluster Complex[1,2]

| Time (days) | Temperature (° C.) | PP Conversion | PO Selectivity | Cumulative $H_2O$/PO |
|---|---|---|---|---|
| 0.5 | 146 | 0.20 | 97.4 | 3.79 |
| 1.0 | 209 | 1.00 | 91.3 | 3.92 |
| 1.5 | 209 | 0.99 | 90.8 | 4.15 |
| 2.0 | 242 | 1.71 | 87.2 | 4.38 |
| 2.5 | 240 | 1.60 | 86.6 | 4.63 |
| 3.0 | 241 | 1.55 | 86.3 | 4.82 |

TABLE 5-continued

Hydro-oxidation of Propylene Using Au Cluster Complex[1,2]

| Time (days) | Temperature (° C.) | PP Conversion | PO Selectivity | Cumulative $H_2O$/PO |
|---|---|---|---|---|
| 3.5 | 240 | 1.51 | 86.4 | 4.99 |
| 4.0 | 238 | 1.49 | 86.1 | 5.15 |
| 4.5 | 240 | 1.48 | 86.1 | 5.28 |
| 5.0 | 239 | 1.47 | 85.9 | 5.41 |
| 5.5 | 243 | 1.43 | 86.1 | 5.52 |
| 6.0 | 240 | 1.43 | 86.1 | 5.57 |
| 6.5 | 240 | 1.42 | 85.6 | 5.73 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLE 6

Example 5 is repeated, with the exception that Negatively Charged Nanogold® Au-ligand cluster complex (30 nmol; 1.4 nm gold particles that contain multiple carboxylic acid groups per molecule; Nanoprobes, Incorporated; Catalog no. 2023) is used in place of the Positively Charged Nanogold® Au-ligand cluster complex. Results are shown in Table 6 and FIGS. 10 and 11.

TABLE 6

Hydro-oxidation of Propylene Using Au Cluster Complex[1,2]

| Time (days) | Temperature (° C.) | PP Conversion | PO Selectivity | Cumulative $H_2O$/PO |
|---|---|---|---|---|
| 0.5 | 143 | 0.26 | 96.8 | 2.65 |
| 1.0 | 199 | 1.19 | 95.9 | 2.45 |
| 1.5 | 210 | 1.50 | 95.3 | 2.44 |
| 2.0 | 227 | 2.02 | 94.0 | 2.47 |
| 2.5 | 230 | 2.01 | 93.8 | 2.54 |
| 3.0 | 233 | 2.02 | 93.4 | 2.60 |
| 3.5 | 236 | 2.03 | 93.2 | 2.67 |
| 4.0 | 236 | 1.95 | 93.0 | 2.73 |
| 4.5 | 239 | 2.02 | 92.5 | 2.78 |
| 5.0 | 239 | 1.98 | 92.5 | 2.84 |
| 5.5 | 239 | 1.96 | 92.3 | 2.88 |
| 6.0 | 240 | 1.95 | 92.4 | 2.91 |
| 6.5 | 240 | 1.92 | 92.3 | 2.96 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLE 7

A portion of CsOAc-impregnated titanosilicate support prepared as described in Example 2 is oven dried at 136° C. for 1 hour. A gold cluster solution is prepared by mixing $Au_{55}[P(C_6H_5)_3]_{12}Cl_6$ (0.0040 g; Strem Chemicals, Incorporated) with chloroform (4.616 g). The solution (1.420 g) is then added to the CsOAc/titanosilicate support (1.20 g). The sample is covered and held at room temperature for about 50 minutes. The sample is transferred to a vacuum oven, heated to 100° C., held at 100° C. for 30 minutes, cooled to room temperature, and then maintained under vacuum overnight to yield a catalyst precursor composition of this invention. The catalyst precursor composition is conditioned in the reactor to form a catalyst composition of this invention, which is tested in the hydro-oxidation of propylene; both the conditioning and the hydro-oxidation being conducted in the manner described in Example 1. Results are shown in Table 7 and FIGS. 12 and 13.

TABLE 7

Hydro-oxidation of Propylene Using $Au_{55}$ Cluster Complex[1,2]

| Time (days) | Temperature (° C.) | PP Conversion | PO Selectivity | Cumulative $H_2O$/PO |
|---|---|---|---|---|
| 0.5 | 143 | 0.17 | 93.9 | 5.78 |
| 1.0 | 219 | 1.49 | 93.2 | 4.33 |
| 1.5 | 235 | 2.01 | 91.7 | 4.13 |
| 2.0 | 236 | 2.01 | 91.5 | 4.10 |
| 2.5 | 237 | 2.01 | 91.4 | 4.10 |
| 3.0 | 237 | 1.98 | 91.4 | 4.12 |
| 3.5 | 237 | 1.97 | 91.1 | 4.15 |
| 4.0 | 238 | 1.99 | 91.0 | 4.18 |
| 4.5 | 240 | 2.05 | 90.7 | 4.22 |
| 5.0 | 240 | 2.04 | 90.5 | 4.25 |
| 5.5 | 240 | 2.04 | 90.5 | 4.29 |
| 6.0 | 240 | 2.00 | 90.2 | 4.33 |
| 6.5 | 240 | 1.98 | 90.3 | 4.37 |
| 7.0 | 240 | 1.99 | 90.0 | 4.41 |
| 7.5 | 240 | 1.97 | 90.0 | 4.46 |
| 8.0 | 240 | 1.94 | 90.0 | 4.50 |
| 8.5 | 240 | 1.90 | 90.0 | 4.54 |
| 9.0 | 240 | 1.92 | 89.5 | 4.58 |
| 9.5 | 240 | 1.87 | 89.6 | 4.62 |
| 10.0 | 240 | 1.85 | 89.7 | 4.66 |
| 10.5 | 240 | 1.83 | 89.7 | 4.70 |
| 11.0 | 240 | 1.80 | 89.6 | 4.74 |
| 11.5 | 240 | 1.79 | 89.3 | 4.79 |
| 12.0 | 240 | 1.79 | 89.1 | 4.84 |
| 12.5 | 240 | 1.78 | 88.9 | 4.89 |
| 13.0 | 240 | 1.75 | 89.1 | 4.94 |
| 13.5 | 240 | 1.71 | 89.1 | 4.99 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLE 8

A portion of CsOAc-impregnated titanosilicate support prepared as described in Example 2 is oven dried at 136° C. for 1 hour. An aqueous barium acetate solution is prepared by mixing water (4.704 g) and barium acetate (0.0131 g). The barium acetate solution (0.387 g) is added to the CsOAc/titanosilicate support (0.55 g). The sample is transferred to a vacuum oven and is heated under vacuum to 70° C. and held for 1 hour. The heat is turned off and the sample is cooled to room temperature and maintained under vacuum overnight. A portion of CsOAc/barium acetate/titanosilicate support is oven dried at 136° C. for 1 hour. A gold cluster solution is prepared by mixing Nanogold® Au-ligand cluster complex (30 nmol; 1.4 nm gold particles; Nanoprobes, Incorporated; Catalog no. 2010) with cold methanol (2.185 g). The solution (0.375 g) is then added to the CsOAc/barium acetate/titanosilicate support (0.55 g). The sample is covered and held in a freezer for 50 minutes. The sample is transferred to a vacuum oven, heated to 100° C., held at 100° C. for 60 minutes, cooled to room temperature, and then maintained under vacuum overnight to yield a catalyst precursor composition of this invention. The catalyst precursor composition is then conditioned in the reactor to form a catalyst composition of this invention, which is tested in the hydro-oxidation of propylene; both the conditioning and the hydro-oxidation being conducted in the manner described in Example 1. Results are shown in Table 8 and FIGS. 14 and 15.

TABLE 8

Hydro-oxidation of Propylene Using Au Cluster Complex[1,2]

| Time (hrs) | Temperature (°C.) | PP Conversion | PO Selectivity | Cumulative H$_2$O/PO |
|---|---|---|---|---|
| 5 | 142 | 0.09 | 90.0 | 0.00 |
| 10 | 141 | 0.08 | 95.5 | 0.00 |
| 15 | 218 | 0.69 | 92.1 | 0.40 |
| 20 | 229 | 1.06 | 92.8 | 1.08 |
| 25 | 254 | 1.74 | 91.1 | 1.56 |
| 30 | 255 | 1.96 | 90.8 | 1.96 |
| 35 | 255 | 1.99 | 91.2 | 2.17 |
| 40 | 255 | 2.00 | 91.4 | 2.36 |
| 45 | 256 | 2.01 | 91.3 | 2.51 |
| 50 | 255 | 1.97 | 91.1 | 2.60 |
| 55 | 254 | 1.88 | 91.1 | 2.70 |
| 60 | 255 | 1.90 | 91.4 | 2.76 |
| 65 | 255 | 1.88 | 91.0 | 2.83 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLES 9 to 16

A series of catalysts is prepared as follows: A portion of the titanosilicate support prepared as described hereinabove is oven dried at 136° C. for 1 hour. An aqueous alkali metal salt solution is prepared by mixing water (5 g) and an alkali metal salt as follows: Example 9: lithium acetate, LiOAc, 0.018 g; Example 10: sodium acetate, NaOAc, 0.0224 g; Example 11: potassium acetate, KOAc, 0.0271 g; Example 12: rubidium acetate, RbOAc, 0.0390 g; Example 13: cesium carbonate, Cs$_2$CO$_3$, 0.0440 g; Example 14: cesium formate, CsOCH(O), 0.048 g; Example 15: cesium bicarbonate, CsHCO$_3$, 0.054 g; and Example 16: cesium oxalate, 0.048 g. The aqueous alkali metal salt solution is added to the titanosilicate support at 70 weight percent wetness impregnation. The sample is transferred to a vacuum oven and is held under vacuum at room temperature for 30 minutes, heated under vacuum to 70° C., and then held under vacuum at 70° C. for 1 hour. The heat is turned off and the sample is allowed to cool to room temperature and maintained under vacuum overnight. A portion of the alkali metal salt-impregnated titanosilicate support is oven dried at 136° C. for 1 hour. A gold cluster solution is prepared by mixing Nanogold® Au-ligand cluster complex (Nanoprobes, Incorporated; Catalog no. 2010; 1.4 nm gold particles; 60 nmol for Ex. 9-12; 30 nmol for Ex. 13-16) with cold methanol (2.173 g). The solution (0.36-0.39 g) is then added to the alkali metal salt-impregnated titanosilicate support (0.56 g). The sample is covered and held in a freezer for about 90 minutes. The sample is transferred to a vacuum oven, heated to 100° C., held at 100° C. for 30 minutes, cooled to room temperature, and then maintained under vacuum overnight to yield a catalyst precursor composition of this invention. The catalyst precursor composition is then conditioned in the reactor to form a catalyst composition of this invention, which is tested in the hydro-oxidation of propylene; both the conditioning and the hydro-oxidation being conducted in the manner described in Example 1. Results are shown for each catalyst in Tables 9 and 10.

TABLE 9

Hydro-oxidation of Propylene Using Au Cluster and Various Promoters[1,2]

| Example (Promoter) | Time (days) | Temperature (°C.) | PP Conversion | PO Selectivity | Cumulative H$_2$O/PO |
|---|---|---|---|---|---|
| 9 (LiOAc) | 0.5 | 144 | 0.25 | 98.2 | 2.04 |
| | 1.0 | 212 | 0.96 | 93.5 | 2.31 |
| | 2.0 | 240 | 1.84 | 86.3 | 3.06 |
| | 3.0 | 240 | 1.65 | 85.7 | 3.50 |
| | 4.0 | 240 | 1.55 | 85.5 | 3.75 |
| | 5.0 | 240 | 1.50 | 84.8 | 3.91 |
| | 6.0 | 240 | 1.42 | 84.8 | 4.03 |
| 10 (NaOAc) | 0.5 | 146 | 0.30 | 98.9 | 1.79 |
| | 1.0 | 210 | 1.51 | 93.3 | 1.99 |
| | 2.0 | 231 | 1.98 | 91.5 | 2.45 |
| | 3.0 | 240 | 1.99 | 90.0 | 2.77 |
| | 4.0 | 240 | 1.82 | 89.7 | 3.00 |
| | 5.0 | 240 | 1.71 | 89.1 | 3.16 |
| | 6.0 | 240 | 1.61 | 89.2 | 3.27 |
| 11 (KOAc) | 0.5 | 146 | 0.32 | 99.3 | 5.55 |
| | 1.0 | 210 | 1.64 | 93.2 | 3.76 |
| | 2.0 | 228 | 2.05 | 91.1 | 3.43 |
| | 3.0 | 235 | 2.01 | 90.8 | 3.50 |
| | 4.0 | 235 | 1.84 | 89.9 | 3.62 |
| | 5.0 | 235 | 1.74 | 89.9 | 3.71 |
| | 6.0 | 235 | 1.65 | 89.9 | 3.79 |
| 12 (RbOAc) | 0.5 | 143 | 0.29 | 99.2 | 2.16 |
| | 1.0 | 183 | 0.82 | 96.3 | 2.13 |
| | 2.0 | 225 | 2.05 | 92.6 | 2.62 |
| | 3.0 | 231 | 2.06 | 91.1 | 2.93 |
| | 4.0 | 231 | 1.86 | 91.2 | 3.15 |
| | 5.0 | 231 | 1.75 | 91.5 | 3.31 |
| | 6.0 | 231 | 1.64 | 91.3 | 3.43 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

TABLE 10

Hydro-oxidation of Propylene Using Au Cluster and Various Promoters[1,2]

| Example (Promoter) | Time (hours) | Temperature (°C.) | PP Conversion | PO Selectivity | Cumulative H$_2$O/PO |
|---|---|---|---|---|---|
| 13 (Cs$_2$CO$_3$) | 5 | 142 | 0.24 | 97.6 | 2.71 |
| | 10 | 140 | 0.19 | 99.4 | 2.78 |
| | 20 | 199 | 1.03 | 95.5 | 2.71 |
| | 30 | 229 | 1.95 | 93.9 | 2.65 |
| | 40 | 231 | 1.89 | 93.8 | 2.67 |
| | 50 | 237 | 1.97 | 92.8 | 2.71 |
| | 60 | 237 | 1.88 | 92.8 | 2.75 |
| | 70 | 240 | 1.90 | 92.5 | 2.79 |
| 14 (CsOCH(O)) | 5 | 144 | 0.02 | 40.9 | 39.33 |
| | 10 | 140 | 0.21 | 100.0 | 8.90 |
| | 20 | 199 | 1.08 | 95.7 | 5.12 |
| | 40 | 231 | 1.96 | 94.1 | 3.67 |
| | 60 | 237 | 1.99 | 93.4 | 3.36 |
| | 80 | 240 | 1.98 | 92.6 | 3.25 |
| | 100 | 240 | 1.86 | 92.7 | 3.20 |
| | 110 | 240 | 1.78 | 92.9 | 3.19 |
| 15 (CsHCO$_3$) | 5 | 142 | 0.25 | 92.8 | 6.15 |
| | 10 | 140 | 0.20 | 98.3 | 4.07 |
| | 20 | 198 | 1.01 | 95.4 | 3.28 |
| | 40 | 231 | 1.82 | 93.9 | 2.92 |
| | 60 | 237 | 1.86 | 92.9 | 2.92 |
| | 80 | 240 | 1.81 | 92.4 | 2.96 |
| | 100 | 240 | 1.71 | 92.1 | 3.01 |
| | 110 | 240 | 1.64 | 92.1 | 3.02 |
| 16 (Cs oxalate) | 5 | 142 | 0.24 | 96.6 | 4.18 |
| | 10 | 141 | 0.20 | 97.2 | 3.38 |
| | 20 | 199 | 1.02 | 96.6 | 2.94 |
| | 40 | 231 | 1.87 | 94.3 | 2.72 |
| | 60 | 237 | 1.90 | 93.3 | 2.74 |
| | 80 | 240 | 1.86 | 92.9 | 2.81 |

TABLE 10-continued

Hydro-oxidation of Propylene Using
Au Cluster and Various Promoters[1,2]

| Example (Promoter) | Time (hours) | Temperature (° C.) | PP Conversion | PO Selectivity | Cumulative H₂O/PO |
|---|---|---|---|---|---|
| | 100 | 240 | 1.76 | 92.9 | 2.85 |
| | 110 | 240 | 1.69 | 92.9 | 2.87 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLE 17

A portion of the titanosilicate support, prepared as described in hereinabove, is oven dried at 136° C. for 1 hour. An aqueous cesium chloride (CsCl) solution is prepared by mixing water (5.022 g) and CsCl (0.0454 g). The CsCl solution (1.053 g) is added to the titanosilicate support (1.50 g). The sample is transferred to a vacuum oven, held under vacuum at room temperature for 30 minutes, heated under vacuum to 70° C., and then held under vacuum at 70° C. for 1 hour. The heat is turned off and the sample is allowed to cool to room temperature and maintained under vacuum overnight. A portion of the CsCl/titanosilicate support is oven dried at 136° C. for 1 hour. A gold cluster solution is prepared by mixing Nanogold® Au-ligand cluster complex (30 nmol; 1.4 nm gold particles; Nanoprobes, Incorporated; Catalog no. 2010) with cold methanol (2.155 g). The solution (0.373 g) is then added to the CsCl/titanosilicate support (0.55 g). The sample is covered and held in a freezer for about 60 minutes. The sample is transferred to a vacuum oven, heated to 100° C., held at 100° C. for 30 minutes, cooled to room temperature, and then maintained under vacuum overnight to yield a catalyst precursor composition of this invention. The catalyst precursor composition is then conditioned in the reactor to form a catalyst composition of this invention, which is tested in the hydro-oxidation of propylene; both the conditioning and the hydro-oxidation being conducted in the manner described in Example 1 hereinabove with the results shown in Table 11.

TABLE 11

Hydro-oxidation of Propylene Using
Au Cluster and Various Promoters[1,2]

| Example (Promoter) | Time (hours) | Temperature (° C.) | PP Conversion | PO Selectivity | Cumulative H₂O/PO |
|---|---|---|---|---|---|
| 17 (CsCl) | 5 | 141 | 0.12 | 90.9 | 6.35 |
| | 10 | 140 | 0.10 | 98.8 | 5.33 |
| | 20 | 224 | 1.07 | 93.0 | 4.37 |
| | 30 | 255 | 2.02 | 90.1 | 3.83 |
| | 40 | 256 | 2.00 | 89.9 | 3.69 |
| | 50 | 258 | 2.02 | 89.9 | 3.63 |
| | 60 | 258 | 1.95 | 90.1 | 3.61 |
| | 70 | 259 | 1.98 | 89.9 | 3.61 |
| | 80 | 259 | 1.96 | 89.8 | 3.61 |
| 18 (CsCl) + (CsOAc) | 5 | 140 | 0.15 | 94.2 | 6.25 |
| | 10 | 140 | 0.12 | 97.1 | 4.88 |
| | 20 | 224 | 1.20 | 93.5 | 4.06 |
| | 30 | 244 | 1.96 | 92.5 | 3.52 |
| | 40 | 246 | 1.96 | 92.5 | 3.36 |
| | 50 | 249 | 1.99 | 92.1 | 3.28 |
| | 60 | 249 | 1.95 | 92.2 | 3.24 |
| | 70 | 251 | 2.00 | 91.7 | 3.22 |
| | 80 | 251 | 1.97 | 91.8 | 3.22 |
| 19 (CsTFA) | 5 | 215 | 2.07 | 94.7 | 1.49 |
| | 10 | 213 | 2.01 | 94.9 | 1.75 |
| | 20 | 215 | 1.86 | 94.9 | 2.01 |
| | 30 | 215 | 1.78 | 95.0 | 2.17 |
| | 40 | 224 | 2.10 | 93.9 | 2.30 |
| | 50 | 225 | 1.98 | 94.1 | 2.41 |
| | 60 | 229 | 2.03 | 93.8 | 2.50 |
| | 70 | 228 | 1.97 | 94.1 | 2.57 |
| 20 (CsTFA) + (CsOAc) | 5 | 214 | 2.10 | 94.8 | 1.42 |
| | 10 | 214 | 2.03 | 94.9 | 1.68 |
| | 20 | 215 | 1.89 | 95.4 | 1.95 |
| | 30 | 214 | 1.81 | 95.1 | 2.11 |
| | 40 | 225 | 2.12 | 94.3 | 2.24 |
| | 50 | 225 | 1.99 | 94.3 | 2.36 |
| | 60 | 227 | 2.05 | 93.8 | 2.45 |
| | 70 | 229 | 1.99 | 94.1 | 2.52 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

EXAMPLE 18

Example 17 is repeated, with the exception that cesium chloride (0.0228 g) and cesium acetate (0.0261 g) are mixed with water (5.001 g) and a portion of the resulting aqueous CsCl/CsOAc solution (1.047 g) is impregnated onto the titanosilicate support, in place of the cesium chloride solution of Example 17. Results are shown in Table 11.

EXAMPLE 19

Example 17 is repeated, with the exception that a solution is prepared by mixing water (35.013 g) and cesium trifluoroacetate (Fluka, 6 M, 0.304 mL), and the resulting cesium trifluoroacetate solution (1.395 g) is impregnated onto the titanosilicate support (2.00 g), in place of the cesium chloride solution of Example 17. Results are shown in Table 11.

EXAMPLE 20

Example 17 is repeated, with the exception that a solution containing cesium acetate and cesium trifluoroacetate is prepared and deposited onto the titanosilicate in place of the cesium chloride solution, the procedure as follows. An aqueous cesium trifluoroacetate solution is prepared by mixing water (35.013 g) and cesium trifluoroacetate (Fluka, 6 M, 0.304 mL). An aqueous cesium acetate solution is prepared by mixing water (17.500 g) and cesium acetate (0.1830 g). A combined cesium acetate and cesium trifluoroacetate solution is prepared by mixing 2.5 mL of the cesium trifluoroacetate solution with 2.5 mL of the cesium acetate solution. Then the combined solution (1.397 g) is deposited onto the titanosilicate (2.00 g), and the procedure of Example 17 is continued essentially without change. Results are shown in Table 11.

EXAMPLE 21

A portion of CsOAc-impregnated titanosilicate support prepared as described in Example 2 is calcined at 500° C. for 1 hour. A gold cluster solution is prepared by mixing $Au_{55}[P(C_6H_5)_3]_{12}Cl_6$ (0.0040 g; Strem Chemicals, Incorporated) with chloroform (4.616 g). The solution (1.442 g) is then added to the calcined support (1.20 g). The sample is covered and held at room temperature for about 50 minutes. The sample is transferred to a vacuum oven, heated to 100° C., held at 100° C. for 30 minutes, cooled to room temperature, and then maintained under vacuum overnight to yield a catalyst precursor composition of this invention. The catalyst precursor composition is then conditioned in the reactor to form a catalyst composition of this invention, which is tested in the hydro-oxidation of propylene; both the conditioning and the hydro-oxidation being conducted in the manner described in Example 1. Results are shown in Table 12.

TABLE 12

Hydro-oxidation of Propylene Using $Au_{55}$ Cluster[1,2]

| Time (days) | Temperature (° C.) | PP Conversion | PO Selectivity | Cumulative $H_2O/PO$ |
|---|---|---|---|---|
| 0.5 | 143 | 0.20 | 94.8 | 7.70 |
| 1.0 | 219 | 1.61 | 91.8 | 5.31 |
| 2.0 | 233 | 2.01 | 90.4 | 4.94 |
| 3.0 | 234 | 1.99 | 90.3 | 4.92 |
| 4.0 | 235 | 2.01 | 90.1 | 4.94 |
| 5.0 | 237 | 2.04 | 89.4 | 4.99 |
| 6.0 | 237 | 1.99 | 89.5 | 5.05 |
| 7.0 | 237 | 1.99 | 89.1 | 5.12 |
| 8.0 | 237 | 1.95 | 89.0 | 5.19 |
| 9.0 | 237 | 1.90 | 89.1 | 5.27 |
| 10.0 | 237 | 1.86 | 88.7 | 5.34 |
| 11.0 | 237 | 1.86 | 88.6 | 5.42 |
| 12.0 | 237 | 1.85 | 88.2 | 5.53 |
| 13.0 | 237 | 1.80 | 88.1 | 5.63 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

Comparative Experiment 1

A hydro-oxidation catalyst of the prior art is prepared from chloroauric acid and evaluated in the hydro-oxidation of propylene with oxygen in the presence of hydrogen under isothermal process conditions. A portion of the titanosilicate support, prepared as described in Example 1 hereinabove, is oven dried at 110° C. for 1 hour. An aqueous solution is prepared by mixing water (5.01 g), sodium acetate (0.098 g), and hydrogen tetrachloroaurate(III) trihydrate ($HAuCl_4 \cdot 3H_2O$, 0.022 g). The gold solution (0.772 g) is added to the titanosilicate support (1.10 g). The sample is transferred to a vacuum oven, heated to 70° C., and then held under vacuum at 70° C. for 1 hour. The heat is turned off and the sample is allowed to cool to room temperature and maintained under vacuum overnight. The sample is then tested in the hydro-oxidation of propylene in the manner described in Example 1 hereinabove. The reactor temperature is increased to 160° C. and held there for the duration of the run. Results are shown in Table 13 and in FIGS. 16 and 17.

TABLE 13

Hydro-oxidation of Propylene Using Chloroauric Acid[1,2]

| Time (days) | Temperature (° C.) | PP Conversion | PO Selectivity | Cumulative $H_2O/PO$ |
|---|---|---|---|---|
| 1 | 160 | 2.05 | 98.0 | 2.59 |
| 5 | 160 | 1.72 | 96.7 | 3.98 |
| 10 | 160 | 1.37 | 95.7 | 5.01 |
| 15 | 160 | 1.12 | 95.2 | 5.71 |
| 20 | 160 | 0.95 | 94.7 | 6.22 |
| 25 | 160 | 0.82 | 94.2 | 6.61 |
| 30 | 160 | 0.74 | 93.3 | 6.90 |
| 35 | 160 | 0.68 | 92.8 | 7.15 |
| 40 | 160 | 0.61 | 93.0 | 7.39 |

[1]PP = propylene; PO = propylene oxide

TABLE 13-continued

Hydro-oxidation of Propylene Using Chloroauric Acid[1,2]

| Time (days) | Temperature (° C.) | PP Conversion | PO Selectivity | Cumulative $H_2O/PO$ |
|---|---|---|---|---|

[2]Feed: 30 percent propylene, 10 percent oxygen, 10 percent hydrogen, balance helium, 250 cc/min space velocity, 100 psig (690 kPa).

When Table 13 and FIGS. 16 and 17 are compared with the previous Tables and Figures representative of this invention, it is seen that activity of the prior art catalyst degrades more quickly and the cumulative water/PO ratio increases more quickly as compared with the catalysts of the invention.

Comparative Experiment 2

A hydro-oxidation catalyst of the prior art is prepared from chloroauric acid and evaluated in the hydro-oxidation of propylene with oxygen in the presence of hydrogen using temperature adjustments for operation under essentially constant conversion of propylene. A portion of the titanosilicate support prepared as in Example 1 hereinabove is oven dried at 110° C. for 1 hour. An aqueous solution is prepared by mixing water (5.00 g), sodium acetate (0.098 g), and hydrogen tetrachloroaurate(III) trihydrate (0.022 g). The solution (1.40 g) is added to the titanosilicate support (2.00 g). The sample is transferred to a vacuum oven, heated to 70° C., and then held under vacuum at 70° C. for 1 hour. The heat is turned off and the sample is allowed to cool to room temperature and maintained under vacuum overnight. The sample is then tested in the hydro-oxidation of propylene in the manner described in Example 1 hereinabove. The reactor temperature is increased at various intervals to maintain propylene conversions between approximately 1.5-2.1 percent. Results are shown in Table 14 and in FIGS. 18 and 19.

TABLE 14

Hydro-oxidation of Propylene Using Chloroauric Acid[1,2]

| Time (days) | Temperature (° C.) | PP Conversion | PO Selectivity | Cumulative $H_2O/PO$ |
|---|---|---|---|---|
| 1 | 153 | 1.66 | 98.8 | 2.46 |
| 2 | 152 | 1.55 | 99.1 | 2.78 |
| 3 | 152 | 1.53 | 98.8 | 3.04 |
| 4 | 159 | 1.71 | 98.6 | 3.29 |
| 5 | 163 | 1.95 | 97.7 | 3.56 |
| 6 | 166 | 1.98 | 97.6 | 3.84 |
| 7 | 170 | 2.03 | 97.1 | 4.13 |
| 8 | 175 | 2.09 | 96.6 | 4.42 |
| 9 | 178 | 2.00 | 96.0 | 4.72 |
| 10 | 178 | 1.80 | 95.9 | 5.02 |
| 11 | 178 | 1.67 | 96.0 | 5.30 |
| 12 | 192 | 2.00 | 94.2 | 5.61 |
| 13 | 199 | 2.01 | 92.7 | 5.95 |
| 14 | 207 | 2.05 | 90.2 | 6.33 |
| 15 | 214 | 2.10 | 86.5 | 6.75 |
| 16 | 214 | 1.91 | 87.4 | 7.21 |
| 17 | 214 | 1.84 | 87.6 | 7.62 |
| 18 | 220 | 1.90 | 85.7 | 7.99 |
| 19 | 227 | 1.98 | 81.6 | 8.39 |
| 20 | 232 | 1.94 | 78.6 | 8.84 |
| 21 | 235 | 1.85 | 76.9 | 9.32 |
| 22 | 237 | 1.71 | 77.1 | 9.78 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

When Table 14 and FIGS. 18 and 19 are compared with the previous Tables and Figures representative of this invention, it is seen that activity of the prior art catalyst degrades more quickly and the cumulative water/PO ratio increases more quickly as compared with the catalysts of the invention.

EXAMPLES 22 to 24

Three mixed metal cluster catalysts are prepared as follows. A cluster complex solution is prepared by mixing methylene chloride (15 mL) with a mixed metal cluster complex: Example 22—$Pt(AuPPh_3)_8(NO_3)_2$, 16 mg; Example 23—$Pt(AuPPh_3)_8Ag$—$(NO_3)_3$, 15 mg; Example 24—$Pt(AuPPh_3)_7Ag_2(NO_3)_3$, 14 mg. A portion of the NaOAc-impregnated titanosilicate support prepared as described in Example 4 (2.00 g) is added to the cluster complex solution with vigorous shaking, and the excess liquid is decanted off. The sample is dried in a hood for 1 hour, followed by vacuum drying at 70° C. for 1 hour. The catalyst precursor is tested in the hydro-oxidation of propylene as described in Example 1 with the results shown in Table 15.

TABLE 15

Hydro-oxidation of Propylene Using Au-Mixed Metal Clusters[1,2]

| Example (Cluster) | Time (days) | Temperature (° C.) | PP Conversion | PO Selectivity | Cumulative $H_2O/PO$ |
|---|---|---|---|---|---|
| 22 | 1 | 147 | 8.26 | 12.8 | 7.58 |
| $(Pt(AuPPh_3)_8(NO_3)_2)$ | 2 | 160 | 10.6 | 12.6 | 6.38 |
|  | 3 | 160 | 11.3 | 11.6 | 6.09 |
|  | 4 | 160 | 11.7 | 10.7 | 5.98 |
| 23 | 1 | 145 | 5.41 | 15.2 | 7.50 |
| $(Pt(AuPPh_3)_8Ag(NO_3)_3)$ | 2 | 160 | 6.16 | 18.0 | 7.07 |
|  | 3 | 160 | 6.31 | 17.3 | 7.02 |
|  | 4 | 160 | 6.51 | 16.1 | 7.04 |
| 24 | 1 | 145 | 3.33 | 23.3 | 6.25 |
| $(Pt(AuPPh_3)_7Ag_2(NO_3)_3)$ | 2 | 160 | 3.94 | 25.6 | 6.34 |
|  | 3 | 160 | 3.85 | 24.7 | 6.48 |
|  | 4 | 160 | 3.84 | 23.8 | 6.62 |

[1]PP = propylene; PO = propylene oxide
[2]Feed: 30 percent propylene, 10 percent oxygen, 10 percent hydrogen, balance helium, 250 cc/min space velocity, 100 psig (690 kPa).

The invention claimed is:

1. A catalyst composition comprising gold nanoparticles deposited on particles of a nanoporous titanosilicate support, the catalyst being prepared by a process comprising depositing a gold-ligand cluster complex onto a nanoporous titanosilicate support under conditions sufficient to form a catalyst precursor, and then heating and/or chemically treating the catalyst precursor under conditions sufficient to form the catalyst.

2. The composition of claim 1 wherein the gold nanoparticles have a median particle size ranging from 0.8 nm to less than 8 nm.

3. The composition of claim 1 wherein the gold is loaded onto the support in an amount greater than 10 ppm and less than 20,000 ppm, based on the total weight of the catalyst.

4. The composition of claim 1 wherein the support is a nanoporous titanosilicate selected from the group consisting of TS-1, TS-2, Ti-beta, Ti-MCM-41, Ti-MCM-48, Ti-SBA-15, and Ti-SBA-3.

5. The composition of claim 4 wherein the nanoporous titanosilicate has an MFI crystalline structure and a Si:Ti atomic ratio of greater than 5:1 and less than 1,000:1.

6. The composition of claim 1 wherein the ligand is selected from organophosphorus compounds, thiolates, thiols, amines, imines, amides, imides, carbon monoxide, halides and mixtures thereof.

7. The composition of claim 1 wherein the gold in the gold-ligand cluster complex is selected from the group consisting $Au_3$, $Au_4$, $Au_5$, $Au_6$, $Au_7$, $Au_8$, $Au_9$, $Au_{10}$, $Au_{11}$, $Au_{12}$, $Au_{13}$, $Au_{(20+/-2)}$, $Au_{(55+/-5)}$, $Au_{(101+/-10)}$, and mixtures thereof; and optionally, wherein the cluster further comprises silver.

8. The composition of claim 7 wherein the gold-ligand cluster complex is selected from $(Ph_3Pau)_3OBF_4$, $[(AuPPh_3)_3O]PF_6$, $Au_5(PPh_3)_4Cl$, $Au_6(PPh_3)_6(BF_4)_2$, $Au_6(PPh_3)_6(NO_3)_2$, $Au_6(PPh_3)_6(PF_6)_2$, $Au_8(PPh_3)_8(NO_3)_2$, $Au_8(PPh_3)_7(NO_3)_2$, $Au_9(PPh_3)_8(NO_3)_3$, $Au_{10}(PPh_3)_5(C_6F_5)_4$, $Au_{11}Cl_3\{(m-CF_3C_6H_4)_3P\}_7$, $Au_{11}(PPh_3)_7(PF_6)_3$, $Au_{13}(Pme_2Ph)_{10}Cl_2](PF_6)_3$, $Au_{13}(PPh_3)_4[S(CH_2)_{11}(CH_3)]_4$, $[Au_{13}(PPh_2CH_2PPh_2)_6](NO_3)_4$, $Au_{55}(Ph_2PC_6H_4SO_3Na.2H_2O)_{12}Cl_6$, $Au_{55}(PPh_3)_{12}Cl_6$, gold-ligand cluster complexes having an average gold particle size of about 1.4 nm, and mixtures thereof; wherein in the aforementioned complexes, Ph is phenyl and Me is methyl.

9. The composition of claim 1 wherein the gold-ligand cluster complex further comprises a noble metal selected from the group consisting of ruthenium, rhodium, palladium, osmium, iridium, and platinum, and mixtures thereof, and optionally, wherein the gold-ligand cluster complex further comprises silver.

10. The composition of claim 9 wherein the gold-ligand cluster complex is selected from $[(PPh_3)(CO)Pt(AuPPh_3)_6](PF_6)_2$, $[(PPh_3)Pt(AuPPh_3)_6](NO_3)_2$, $[Pd(AuPPh_3)_8](NO_3)_2$, $[H_4(PPh_3)_2Re(AuPPh_3)_5](PF_6)_2$, $[PPh_3Pt(AuPPh_3)_6](PF_6)_2$, $[H(PPh_3)Pt(AuPPh_3)_7](NO_3)$, $[Pt(AuPPh_3)_7(Ag)_2](NO_3)_3$, $[Pd(AuPPh_3)_8](PF_6)_2$, $[Pt(AuPPh_3)_8](NO_3)_2$, $[Pt(AuPPh_3)_8](PF_6)_2$, $[(PPh_3)Pt(AuPPh_3)_8(Ag)](NO_3)_2$, and $[Pt_2(AuPPh_3)_{10}(Ag)_{13}]Cl_7$, and mixtures thereof; wherein in the aforementioned complexes, Ph is phenyl and Me is methyl.

11. The composition of claim 1 wherein greater than 90 percent of the gold nanoparticles are present on the exterior surface of the particles of the nanoporous titanosilicate support wherein the support has a pore size ranging from 0.2 nm to 1 nm.

12. The catalyst composition of claim 1 wherein greater than 80 weight percent of the gold is metallic gold.

13. The composition of claim 11 wherein the nanoporous titanosilicate support has a surface area greater than 50 $m^2/g$.

14. A process of preparing an olefin oxide comprising contacting an olefin having at least three carbon atoms with oxygen in the presence of hydrogen and in the presence of a catalyst having the composition of claim 1, the contacting being conducted under reaction conditions sufficient to form the olefin oxide.

15. The process of claim 14 wherein the olefin is selected from a $C_{3-12}$ monoolefin or diolefin propylene, butadiene, cyclopentadiene, dicyclopentadiene, styrene, α-methylstyrene, divinylbenzene, allyl alcohol, diallyl ether, allyl ethyl ether, allyl butyrate, allyl acetate, allyl benzene, allyl phenyl ether, allyl propyl ether, allyl anisole, and mixtures thereof.

16. The process of claim 14 wherein when the process is conducted in a gas phase, a diluent is employed selected from the group consisting of helium, nitrogen, argon, methane, carbon dioxide, steam, and mixtures thereof; or wherein when the process is conducted in a liquid phase, a diluent is employed selected from $C_{6-15}$ aromatic hydrocarbons, chlorinated $C_{1-10}$ hydrocarbons, $C_{1-10}$ aliphatic alcohols, chlorinated $C_{1-10}$ alkanols, $C_{2-20}$ ethers, and liquid polyethers, polyalcohols, and polyesters.

17. The process of claim 14 wherein a diluent is used in a gas phase in a quantity greater than 0 and less than 90 mole percent, based on the total moles of olefin, oxygen, hydrogen, and diluent; or wherein a liquid diluent (or solvent) is used in a liquid phase in a quantity greater than 5 and less than 95 weight percent, based on the combined weight of the olefin and the diluent.

18. The process of claim 14 wherein the hydro-oxidation process is conducted at a temperature greater than 160° C. and less than 300° C. and a pressure between atmospheric and 500 psig (3,448 kPa).

19. A catalyst precursor composition comprising a gold-ligand cluster complex deposited on particles of a nanoporous titanosilicate support.

20. The catalyst precursor composition of claim 19 wherein the gold-ligand cluster complex has a diameter (or largest dimension) greater than 0.54 nm+/−0.04 nm.

* * * * *